(12) United States Patent
Amano et al.

(10) Patent No.: US 9,464,983 B2
(45) Date of Patent: Oct. 11, 2016

(54) CONCENTRATION DETERMINATION APPARATUS, PROBE, CONCENTRATION DETERMINATION METHOD, AND PROGRAM

(75) Inventors: Kazuhiko Amano, Tokyo (JP); Koichi Shimizu, Sapporo (JP)

(73) Assignees: SEIKO EPSON CORPORATION, Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 751 days.

(21) Appl. No.: 13/176,422

(22) Filed: Jul. 5, 2011

(65) Prior Publication Data

US 2012/0010477 A1 Jan. 12, 2012

(30) Foreign Application Priority Data

| Jul. 12, 2010 | (JP) | 2010-158097 |
| Jul. 12, 2010 | (JP) | 2010-158098 |
| Jul. 12, 2010 | (JP) | 2010-158099 |
| Jul. 12, 2010 | (JP) | 2010-158100 |

(51) Int. Cl.
| A61B 5/1455 | (2006.01) |
| G01N 21/359 | (2014.01) |
| A61B 5/00 | (2006.01) |
(Continued)

(52) U.S. Cl.
CPC ........... *G01N 21/359* (2013.01); *A61B 5/0075* (2013.01); *A61B 5/1455* (2013.01); *A61B 5/14532* (2013.01); *G01N 21/49* (2013.01); *A61B 5/01* (2013.01); *A61B 5/024* (2013.01); *A61B 5/0402* (2013.01); *A61B 5/6824* (2013.01); *A61B 5/721* (2013.01); *A61B 5/7221* (2013.01); *A61B 5/7257* (2013.01); *A61B 5/7278* (2013.01); *A61B 2560/0252* (2013.01); *G01N 2201/1211* (2013.01)

(58) Field of Classification Search
USPC .................................................. 600/310–344
See application file for complete search history.

(56) References Cited

U.S. PATENT DOCUMENTS

| 5,313,941 A | 5/1994 | Braig et al. |
| 5,370,114 A | 12/1994 | Wong et al. |
(Continued)

FOREIGN PATENT DOCUMENTS

| JP | A-52-63397 | 5/1977 |
| JP | A-07-120384 | 5/1995 |
(Continued)

OTHER PUBLICATIONS

Uichi, "Introduction to Medical Laser," 1st Edition, Ohmsha, Ltd., Jun. 25, 1985, p. 70 (with translation).
(Continued)

*Primary Examiner* — Tse Chen
*Assistant Examiner* — Marjan Fardanesh
(74) *Attorney, Agent, or Firm* — Oliff PLC

(57) ABSTRACT

A concentration determination apparatus may determine a concentration of a target component in an arbitrary layer of an observed object including a plurality of light scattering medium layers. The concentration determination apparatus may include an irradiation unit, light scattering medium layer selection unit, a light receiving unit, a light intensity acquisition unit, an optical absorption coefficient calculation unit, and a concentration calculation unit.

8 Claims, 42 Drawing Sheets

(51) Int. Cl.
*A61B 5/145* (2006.01)
*G01N 21/49* (2006.01)
*A61B 5/01* (2006.01)
*A61B 5/024* (2006.01)
*A61B 5/0402* (2006.01)

(56) References Cited

U.S. PATENT DOCUMENTS

| | | |
|---|---|---|
| 5,515,847 A | 5/1996 | Braig et al. |
| 5,529,755 A | 6/1996 | Higashio et al. |
| 5,615,672 A | 4/1997 | Braig et al. |
| 5,678,556 A | 10/1997 | Maki et al. |
| 5,957,841 A | 9/1999 | Maruo et al. |
| 6,030,342 A | 2/2000 | Amano et al. |
| 6,287,262 B1 | 9/2001 | Amano et al. |
| 6,353,226 B1 | 3/2002 | Khalil et al. |
| 6,414,779 B1 | 7/2002 | Mandella et al. |
| 6,615,061 B1 | 9/2003 | Khalil et al. |
| 6,995,844 B2 | 2/2006 | Hafeman et al. |
| 7,333,841 B2 | 2/2008 | Maruo et al. |
| 2002/0084417 A1 | 7/2002 | Khalil et al. |
| 2004/0142402 A1 | 7/2004 | Maruo et al. |
| 2010/0256920 A1* | 10/2010 | Amano et al. ............. 702/23 |
| 2012/0010477 A1 | 1/2012 | Amano et al. |

FOREIGN PATENT DOCUMENTS

| | | |
|---|---|---|
| JP | A-07-284490 | 10/1995 |
| JP | A-08-029329 | 2/1996 |
| JP | A-08-289882 | 11/1996 |
| JP | A-10-155776 | 6/1998 |
| JP | A-10-510180 | 10/1998 |
| JP | A-2000-074829 | 3/2000 |
| JP | A-2003-50200 | 2/2003 |
| JP | A-2003-144421 | 5/2003 |
| JP | A-2003-202287 | 7/2003 |
| JP | A-2003-531357 | 10/2003 |
| JP | A-2004-321368 | 11/2004 |
| JP | A-2006-198321 | 8/2006 |
| JP | B2-3931638 | 3/2007 |
| JP | B2-3903147 | 4/2007 |
| JP | B2-3931638 | 6/2007 |
| JP | A-2007-259967 | 10/2007 |
| JP | A-2008-237775 | 10/2008 |
| JP | B2-4325179 | 6/2009 |
| JP | B2-4329360 | 6/2009 |
| JP | B2-4362936 | 8/2009 |
| JP | B2-4325179 | 9/2009 |
| JP | B2-4329360 | 9/2009 |
| JP | A-2009-233284 | 10/2009 |
| JP | B2-4362936 | 11/2009 |
| JP | B2-4470939 | 3/2010 |
| JP | B2-4472794 | 3/2010 |
| JP | B2-4470939 | 6/2010 |
| JP | B2-4472794 | 6/2010 |
| JP | A-2012-21811 | 2/2012 |
| WO | WO 97/47239 A1 | 12/1997 |

OTHER PUBLICATIONS

U.S. Appl. No. 13/614,566, filed Sep. 13, 2012.
Sep. 14, 2015 Office Action issued in U.S. Appl. No. 13/614,566.
Apr. 30, 2015 Office Action issued in U.S. Appl. No. 13/614,566.
Jul. 1, 2016 Office Action issued in U.S. Appl. No. 13/614,566.

* cited by examiner

CONCENTRATION DETERMINATION APPARATUS, PROBE, CONCENTRATION DETERMINATION METHOD, AND PROGRAM

BACKGROUND

1. Technical Field

The present invention relates to a concentration determination apparatus, a probe, a concentration determination method, and a program for non-invasively determining a concentration of a target component in an observed object in any of a plurality of light scattering medium layers in a living body.

Priority is claimed on Japanese Patent Application Nos. 2010-158097, 2010-158098, 2010-158099 and 2010-158100 filed on July 12, 2010, the contents of which are incorporated herein by reference 2. Related Art In recent years, diabetics in an age of gluttony continue to increase each year in Japan. Therefore, diabetics with nephritis also continue to increase each year. Patients suffering from chronic renal insufficiency also continue to increase by ten thousand each year and currently number over 280 thousand.

Meanwhile, with the advent of an aging society, a demand for preventive medicine and the importance of personal metabolism management are rapidly increasing. In particular, blood sugar value measurement is important. Glucose metabolism in an early stage of diabetes can be evaluated by blood sugar value measurement. The blood sugar value measurement enables early treatment based on early diagnosis of the diabetes.

Traditionally, the blood sugar value measurement is performed by taking a blood sample from a vein of, for example, an arm or a fingertip and measuring enzyme activity for glucose in the blood. This method of measuring a blood sugar value has various problems, such as that taking a blood sample is complicated and painful, and poses a risk of infection. Further, a measurement tip for adhering blood is required. Thereby, there is a need for a non-invasive blood sugar value measurement method that does not require that a blood sample be taken.

As a method of continuously measuring a blood sugar value, equipment for continuously determining glucose corresponding to a blood sugar value in a state in which an injection needle is pushed into a vein has been developed in USA and is currently in clinical trials. However, since the injection needle is pushed into the vein, there are risks of the needle being left or infection during measurement of the blood sugar value.

There is a need for a blood sugar value measurement apparatus capable of frequently measuring a blood sugar value without taking a blood sample and having no risk of infection. Further, there is a need for a miniaturized blood sugar value measurement apparatus capable of being mounted simply and at any time.

A method of irradiating near-infrared light to skin and obtaining a glucose concentration from a light absorption amount is disclosed in Japanese Patent No. 3931638, for example. In this method, an apparatus irradiates near-infrared continuous light to the skin and calculates a glucose concentration from the light absorption amount. Specifically, a calibration curve representing a relationship among a glucose concentration, a wavelength of irradiated near-infrared light, and a light absorption amount is created in advance. Near-infrared continuous light is irradiated to the skin, and light returned from the skin is scanned in any wavelength band using, for example, a monochromator. A light absorption amount for each wavelength in the wavelength band is obtained, and the light absorption amount in each wavelength is compared with the calibration curve. Accordingly, a glucose concentration, i.e., a blood sugar value, in the blood is calculated.

In general, when near-infrared spectroscopy analysis of a solution or a sample having high moisture content is performed, a spectrum of the sample is greatly shifted due to a temperature change, similar to a spectrum of water. Accordingly, when quantitative analysis is performed using near-infrared spectroscopy, effects of the temperature of the solution or the sample cannot be ignored.

An apparatus for stabilizing a temperature of a contact portion between a measuring surface of a probe tip of a near-infrared light transmitting and receiving optical fiber bundle and tissue near a surface of a living body using a heater and a surface temperature detection means when a glucose concentration of the tissue near the surface of the living body is measured using absorption of light in a near-infrared region is disclosed in Japanese Unexamined Patent Application, First Publication No. 2001-299727.

However, in a conventional method of measuring a glucose concentration in blood or tissue near a surface of a living body from an absorption amount of near-infrared light, a temperature change rate of an absorption coefficient of water contained in the blood or the living body, for the near-infrared light, is great. Thus, it is difficult to accurately measure the glucose concentration in the blood or in the living body.

For example, when a temperature of a contact portion between a measuring surface of a probe tip of a near-infrared light transmitting and receiving optical fiber bundle and tissue near a surface of a living body is stabilized by a heater and a surface temperature detection means, the temperature of the contact portion is reliably stabilized. However, when temperature of the living body is changed, temperature of the tissue near the surface of the living body is also changed and an absorption coefficient for the near-infrared light is changed. It is difficult to accurately measure the glucose concentration in the living body.

Further, in a conventional noninvasive blood sugar value measurement method, a near-infrared absorption spectrum of the dermis is measured by determining a distance between an input and an output of light. For this, the measured absorption spectrum includes an absorption spectrum of an epidermis or a subcutaneous tissue layer as well as the absorption spectrum of the dermis. Noise due to the epidermis or the subcutaneous tissue layer is involved in a change of the observed absorption coefficient.

Further, a conventional glucose concentration measurement apparatus has the following problems.

First, in an apparatus in which a contact portion between a measuring surface of a probe tip of a near-infrared light receiving and emitting optical fiber bundle and tissue near a surface of a living body is heated by a heater, energy for heating the measuring surface in contact with the surface of the living body needs to be supplied, a control means for stabilizing the temperature of the contact portion with the tissue near the surface of the living body is necessary, and the apparatus is expensive and difficult to miniaturize.

Second, the control means for stabilizing the temperature of the contact portion with the tissue near the surface of the living body performs measurement when a near-infrared light receiving and emitting unit are brought into contact with the tissue near the surface, or performs the measurement after the receiving and emitting unit is brought into contact with the tissue near the surface, irradiation of the near-infrared light is initiated and then a given time has elapsed. In addition, the given time is determined based on a target temperature, an ambient temperature, and a living body temperature at a time when the near-infrared light receiving and emitting unit is brought into contact with the tissue near the surface of the living body. Hence, it is necessary to obtain a sufficient thermal equilibrium state until the living body temperature is obtained after the receiving and emitting unit is brought into contact with the tissue near the surface, the irradiation of the near-infrared light is initiated and then the given time has elapsed, after the ambient temperature is obtained when the receiving and emitting unit is brought into contact with the tissue near the surface. Normally, 60 seconds to 120 seconds are needed to obtain thermal equilibrium state.

Thus, it is impossible to miniaturize a conventional glucose concentration measurement apparatus and greatly shorten a measurement time while securing determination accuracy for glucose concentration in a living body.

SUMMARY

The present invention provides a concentration determination apparatus, a concentration determination method, and a program capable of accurately measuring a concentration of a target component included in an observed object, which is a measured object such as skin, in a non-invasive manner by reducing a temperature change rate of an absorption coefficient for \ near-infrared light of water contained in the observed object even when temperature of the observed object is changed.

The present invention provides a concentration determination apparatus, a concentration determination method, and a program that reduce effects of a noise due to layers other than a target layer.

The present invention provides a concentration determination apparatus, a concentration determination method, and a program capable of accurately measuring a concentration of a target component included in an observed object, which is a measured object such as skin, in a non-invasive manner by correcting a temperature change of the observed object based on a temperature change rate of an absorption coefficient for near-infrared light of water contained in the observed object even when a temperature of the observed object is changed.

The present invention provides a concentration determination apparatus, a probe, a concentration determination method, and a program capable of being miniaturized and greatly shortening a measurement time while securing determination accuracy of a glucose concentration in an observed object of a living body by accurately recognizing each state such as a stable state or an active state of the living body and considering a physical status or a mental status of the living body or a periodic change of a pulse rate.

A concentration determination apparatus of the present invention for determining a concentration of a target component in any layer of an observed object including a plurality of light scattering medium layers, may include an irradiation unit for irradiating, to the observed object, light having a specific wavelength at which a temperature change of an absorption coefficient of water in the layer is small; a light scattering medium layer selection unit for selecting backscattered light radiated from the layer from among plural types of backscattered light radiated from the observed object by irradiating the light; a light receiving unit for receiving the backscattered light radiated from the layer; a light intensity acquisition unit for acquiring intensity of the light received by the light receiving unit; an optical absorption coefficient calculation unit for calculating an optical absorption coefficient of the layer based on the light intensity acquired by the light intensity acquisition unit; and a concentration calculation unit for calculating the concentration of the target component in the layer based on the optical absorption coefficient calculated by the optical absorption coefficient calculation unit.

The light having a specific wavelength at which a temperature change of an absorption coefficient of water in the layer is small is irradiated to the observed object by the irradiation unit, the backscattered light radiated from the layer is selected by the light scattering medium layer selection unit from among plural types of backscattered light radiated from the observed object by irradiating the light, and the backscattered light radiated from the layer is received by the light receiving unit. Thus, it is possible to reduce effects of the water in the backscattered light radiated from any layer and reduce effects of the water even in the concentration of a target component in any layer of the observed object calculated based on the backscattered light by using the light having a specific wavelength at which a temperature change of the absorption coefficient of the water is small, as the light irradiated to the observed object. Accordingly, it is possible to reduce the effects of water in the concentration of the target component and accurately measure the concentration of the target component in a non-invasive manner.

The concentration determination apparatus of the present invention may use short pulsed light as the light, and may further include an optical path length distribution storage unit for storing a model of an optical propagation path length distribution in each of the plurality of light scattering medium layers, of the short pulsed light irradiated to the observed object; a time-resolved waveform storage unit for storing a model of a time-resolved waveform of the short pulsed light irradiated to the observed object; an optical path length acquisition unit for acquiring an optical path length of each of the plurality of light scattering medium layers, at the given time, of the model of the optical propagation path length distribution, from the optical path length distribution storage unit; and a light intensity model acquisition unit for acquiring the intensity of the light, at the given time, of the model of the time-resolved waveform of the short pulsed light, from the time-resolved waveform storage unit, and the light intensity acquisition unit may acquire light intensity, at a plurality of times $t_1$ to $t_m$, of the layer, and the optical absorption coefficient calculation unit may calculate the optical absorption coefficient of the layer using the following equation (1):

$$\begin{cases} N(t_1)\ln\left(\frac{N(t_1)}{I(t_1)}\right) = \sum_{i=1}^{n} \mu_i L_i(t_1) \\ \vdots \\ N(t_m)\ln\left(\frac{N(t_m)}{I(t_m)}\right) = \sum_{i=1}^{n} \mu_i L_i(t_m) \end{cases} \quad (1)$$

(where, I(t) denotes the intensity of the light received by the light receiving unit at time t, N(t) denotes the light intensity, at time t, of the model of the time-resolved waveform of the short pulsed light, Li(t) denotes an optical path length of an i-th layer, at time t, of the model of the optical propagation path length distribution in each of the plurality of light scattering medium layers, and $\mu_i$ denotes an optical absorption coefficient of the i-th layer)

The light intensity acquisition unit acquires the light intensity, at a plurality of times $t_1$ to $t_m$, of any layer, and the optical absorption coefficient calculation unit calculates the optical absorption coefficient of the layer using Equation (1). Thus, it is possible to reduce the backscattered light from layers other than any layer as noise and reduce the effects of water in the concentration of the target component by performing time-resolved measurement on the backscattered light. Accordingly, it is also possible to accurately measure the concentration of the target component.

In the concentration determination apparatus, a plurality of times when the light intensity acquisition unit acquires the light intensity may include a peak time of the optical propagation path length distribution of each of the plurality of light scattering medium layers.

It is possible to efficiently select any layer from among the plurality of layers of the observed object the plurality of times when the light intensity acquisition unit acquires the light intensity including the peak time of the optical propagation path length distribution of each of the plurality of light scattering medium layers. Accordingly, it is also possible to accurately measure the concentration of the target component in any layer.

A concentration determination apparatus of the present invention may use short pulsed light as the light and may further include an optical path length distribution storage unit for storing a model of an optical propagation path length distribution in each of the plurality of light scattering medium layers, of the short pulsed light irradiated to the observed object; a time-resolved waveform storage unit for storing a model of a time-resolved waveform of the short pulsed light irradiated to the observed object; an optical path length acquisition unit for acquiring an optical path length of each of the plurality of light scattering medium layers, at the given time, of the model of the optical propagation path length distribution, from the optical path length distribution storage unit; and a light intensity model acquisition unit for acquiring the intensity of the light, at the given time, of the model of the time-resolved waveform of the short pulsed light, from the time-resolved waveform storage unit, and the light intensity acquisition unit may acquire a time change of the light intensity between a given time and at least a given time $\tau$, and the optical absorption coefficient calculation unit may calculate an optical absorption coefficient of the layer using the following equation (2):

$$\begin{cases} \int_0^\tau \ln\left(\frac{N(t)}{I(t)}\right) L_1(t) dt = \sum_{i=1}^n \mu_i \int_0^\tau L_1(t) L_i(t_1) \, dt \\ \vdots \\ \int_0^\tau \ln\left(\frac{N(t)}{I(t)}\right) L_n(t) dt = \sum_{i=1}^n \mu_i \int_0^\tau L_n(t) L_i(t_1) \, dt \end{cases} \quad (2)$$

(where, I(t) denotes the intensity of the light received by the light receiving unit at time t, N(t) denotes the light intensity, at time t, of the model of the time-resolved waveform of the short pulsed light, Li(t) denotes an optical path length of an i-th layer, at time t, of the model of the optical propagation path length distribution in each of the plurality of light scattering medium layers, n denotes the number of layers that are observed objects, and $\mu_i$ denotes an optical absorption coefficient of the i-th layer).

The light intensity acquisition unit acquires a time change of the light intensity between a given time and at least a given time ; and the optical absorption coefficient calculation unit calculates an optical absorption coefficient of any layer using Equation (2). Thus, it is possible to reduce the backscattered light from layers other than any layer as noise and the effects of water in the concentration of the target component by performing time-resolved measurement on the backscattered light. Accordingly, it is also possible to accurately measure a concentration of a target component.

In the concentration determination apparatus of the present invention, the concentration calculation unit may calculate the concentration of the target component in the layer using the following equation (3):

$$\begin{cases} \mu_{a(1)} - \mu_{a(2)} = \sum_{j=1}^p g_j(\varepsilon_{j(1)} - \varepsilon_{j(2)}) \\ \vdots \\ \mu_{a(q-1)} - \mu_{a(q)} = \sum_{j=1}^p g_j(\varepsilon_{j(q-1)} - \varepsilon_{j(q)}) \end{cases} \quad (3)$$

(where, $\mu_a$ denotes an optical absorption coefficient in an a-th layer that is the layer, $g_j$ denotes a molar concentration of a j-th component constituting the observed object, $\varepsilon_j$ denotes an optical absorption coefficient of the j-th component, p denotes the number of main components constituting the observed object, and q denotes the number of types of the specific wavelength).

The concentration calculation unit calculates the concentration of a target component in any layer using Equation (3). Thus, it is possible to reduce effects of water in the concentration of the target component by calculating the concentration of the target component in any layer using backscattered light subjected to time-resolved measurement. Accordingly, it is also possible to accurately measure the concentration of the target component.

A concentration determination method of the present invention for determining a concentration of a target component in any layer of an observed object including a plurality of light scattering medium layers may include irradiating, by an irradiation unit, to the observed object, light having a specific wavelength at which a temperature change of an absorption coefficient of water in the layer is small; selecting, by a light scattering medium layer selection unit, backscattered light radiated from the layer from among plural types of backscattered light radiated from the observed object by irradiating the light; receiving, by a light receiving unit, the backscattered light radiated from the layer; acquiring, by a light intensity acquisition unit, intensity of the light received by the light receiving unit; calculating, by an optical absorption coefficient calculation unit, an optical absorption coefficient of the layer based on the light intensity acquired by the light intensity acquisition unit; and calculating, by a concentration calculation unit, the concentration of the target component in the layer based on the optical absorption coefficient calculated by the optical absorption coefficient calculation unit.

The light having a specific wavelength at which a temperature change of an absorption coefficient of water in the layer is small is irradiated to the observed object by the irradiation unit, the backscattered light radiated from the layer is selected from among the plural types of backscattered light radiated from the observed object by irradiating the light by the light scattering medium layer selection unit, and then the backscattered light radiated from the layer is received by the light receiving unit. Thus, it is possible to reduce effects of the water in the backscattered light radiated from any layer and reduce effects of the water even in the concentration of a target component in any layer of the observed object calculated based on the backscattered light using the light having a specific wavelength at which a temperature change of the absorption coefficient of the water in any layer is small, as the light irradiated to the observed object. Accordingly, it is possible to reduce the effects of water in the concentration of the target component and accurately and efficiently measure the concentration of the target component in a non-invasive manner.

A program of the present invention may cause a computer of a concentration determination apparatus for determining a concentration of a target component in any layer of an observed object including a plurality of light scattering medium layers to execute an irradiation process of irradiating, to the observed object, light having a specific wavelength at which a temperature change of an absorption coefficient of water in the layer is small; a light scattering medium layer selection process of selecting backscattered light radiated from the layer from among plural types of backscattered light radiated from the observed object by irradiating the light; a light receiving process of receiving the backscattered light radiated from the layer; a light intensity acquisition process of acquiring intensity of the light received in the light receiving process; an optical absorption coefficient calculation process of calculating an optical absorption coefficient of the layer based on the light intensity acquired in the light intensity acquisition process; and a concentration calculation process of calculating the concentration of the target component in the layer based on the optical absorption coefficient calculated in the optical absorption coefficient calculation process.

The computer of the concentration determination apparatus is caused to execute the irradiation process of irradiating, to the observed object, light having a specific wavelength at which a temperature change of an absorption coefficient of water in the layer is small; the light scattering medium layer selection process of selecting backscattered light radiated from the layer from among plural types of backscattered light radiated from the observed object by irradiating the light; and the light receiving process of receiving the backscattered light radiated from the layer. Thus, it is possible to reduce effects of the water in the backscattered light radiated from any layer and reduce effects of the water even in the concentration of a target component in any layer of the observed object calculated based on the backscattered light by executing the irradiation process of irradiating, to the observed object, light having a specific wavelength at which a temperature change of an absorption coefficient of water in the layer is small. Accordingly, it is possible to reduce the effects of water in the concentration of the target component and accurately and efficiently measure the concentration of the target component in a non-invasive manner.

A concentration determination apparatus of the present invention for determining a concentration of a target component in any layer of an observed object formed of a plurality of light scattering medium layers may include an irradiation unit for irradiating short pulsed light to the observed object; a light receiving unit having a plurality of light receiving units for receiving light obtained as the short pulsed light is backscattered by the observed object; a selection unit for selecting a specific light receiving unit for receiving the light obtained as the short pulsed light is backscattered by the layer, from among the plurality of light receiving units; a light intensity acquisition unit for acquiring intensity of the light received by the specific light receiving unit at a given time since a time when the irradiation unit has irradiated the short pulsed light; an optical path length distribution storage unit for storing a model of an optical propagation path length distribution in each layer of the plurality of light scattering medium layers arranged on a light propagation path from the irradiation unit to the specific light receiving unit, of the short pulsed light irradiated to the observed object; a time-resolved waveform storage unit for storing a model of a time-resolved waveform of the short pulsed light irradiated to the observed object and received by the specific light receiving unit; an optical path length acquisition unit for acquiring an optical path length of each of the plurality of light scattering medium layers, at the given time, of the model of the optical propagation path length distribution, from the optical path length distribution storage unit; a light intensity model acquisition unit for acquiring the intensity of the light, at the given time, of the model of the time-resolved waveform of the short pulsed light, from the time-resolved waveform storage unit; an optical absorption coefficient calculation unit for calculating an optical absorption coefficient of the layer based on the light intensity acquired by the light intensity acquisition unit, the optical path length of each of the plurality of light scattering medium layers acquired by the optical path length acquisition unit, and the light intensity model acquired by the light intensity model acquisition unit; and a concentration calculation unit for calculating the concentration of the target component in the layer based on the optical absorption coefficient calculated by the optical absorption coefficient calculation unit.

Accordingly, a light absorption coefficient of any layer can be selectively calculated from the time-resolved waveform of the received light. Thereby, it is possible to reduce effects of noise due to another layer by calculating the concentration of the target component based on the calculated light absorption coefficient and determine accurate concentration. Here, the short pulsed light refers to pulsed light having a pulse width of about 10 psec or less. Pulsed light having a pulse width in a range of 0.1 psec to 10 psec may be used as the short pulsed light.

In the concentration determination apparatus of the present invention, the light intensity acquisition unit may acquire light intensity at a plurality of times $t_1$ to $t_m$, the number of the plurality of times being equal to or greater than the number of the layers of the observed object, and the optical absorption coefficient calculation unit may calculate the optical absorption coefficient of any layer based on ln denoting a natural logarithm, I(t) denoting the intensity of the light received by the light receiving unit at time t, N(t) denoting the light intensity of the model of the time-resolved waveform of the short pulsed light at time t, $L_i(t)$ denoting the optical path length of an i-th layer, at time t, of the model of the optical propagation path length distribution, and $\mu_i$ denoting an optical absorption coefficient of the i-th layer, using:

$$\begin{cases} N(t_1)\ln\left(\frac{N(t_1)}{I(t_1)}\right) = \sum_{i=1}^{n} \mu_i L_i(t_1) \\ \vdots \\ N(t_m)\ln\left(\frac{N(t_m)}{I(t_m)}\right) = \sum_{i=1}^{n} \mu_i L_i(t_m) \end{cases} \quad (1)$$

In the concentration determination apparatus of the present invention, the irradiation unit may irradiate light having a plurality of wavelengths 1 to q, the optical absorption coefficient calculation unit may calculate the optical absorption coefficient in the layer for each of the plurality of wavelengths irradiated by the irradiation unit, and the concentration calculation unit may calculate the concentration of the target component in the layer, using the following equation (3):

$$\begin{cases} \mu_{a(1)} - \mu_{a(2)} = \sum_{j=1}^{p} g_j(\varepsilon_{j(1)} - \varepsilon_{j(2)}) \\ \vdots \\ \mu_{a(q-1)} - \mu_{a(q)} = \sum_{j=1}^{p} g_j(\varepsilon_{j(q-1)} - \varepsilon_{j(q)}) \end{cases} \quad (3)$$

Here, $\mu_{a(i)}$ denotes the optical absorption coefficient of a wavelength i in the a-th layer that is the layer, $g_j$ denotes a molar concentration of a j-th component forming the observed object, $\varepsilon_{j(i)}$ denotes an optical absorption coefficient for the wavelength i of the j-th component, p denotes the number of main components forming the observed object, and q denotes the number of types of the wavelengths irradiated by the irradiation unit.

In the concentration determination apparatus of the present invention, when a position to which the short pulsed light is irradiated from the irradiation unit to the observed object is defined as an irradiation position, a position to which the light obtained as the short pulsed light is backscattered by the observed object is output from the observed object to the light receiving unit is defined as a light receiving position, and an interval between the irradiation position and the light receiving position is defined as an irradiation light reception interval, the light receiving unit may include a plurality of light receiving units having different irradiation light reception intervals, and the selection unit may select a light receiving unit having an irradiation light reception interval at which the short pulsed light is capable of being propagated to the layer based on a depth of arrival of the short pulsed light into the observed object determined according to the irradiation light reception interval.

In the concentration determination apparatus of the present invention, the irradiation unit may include an irradiation optical fiber for transferring the short pulsed light to a surface of the observed object, the light receiving unit may include a light receiving optical fiber for transferring light backscattered by the observed object, the irradiation optical fiber and the light receiving optical fiber may be mounted to a probe apparatus for fixing the irradiation optical fiber and the light receiving optical fiber with centers of optical fiber cores of the irradiation optical fiber and the light receiving optical fiber being separate by a given irradiation light reception interval, and a leading end portion of the irradiation optical fiber and a leading end portion of the light receiving optical fiber exposed to a leading end portion of the probe apparatus may be brought into contact with a surface of the observed object so that a process of irradiating the short pulse light to the observed object and a process of receiving the light obtained as the short pulsed light is backscattered by the observed object are performed.

In the concentration determination apparatus of the present invention, the light receiving unit may include a plurality of light receiving optical fibers arranged at the same irradiation light reception interval.

In the concentration determination apparatus of the present invention, the light receiving unit may include a focusing element for focusing light transferred by the plurality of light receiving optical fibers arranged at the same irradiation light reception interval, on the same light receiving surface.

In the concentration determination apparatus of the present invention, the irradiation optical fiber and the light receiving optical fiber may be dispersion-compensation-type single-mode optical fibers for compensating for a wavelength dispersion of the light having the plurality of wavelengths 1 to q irradiated by the irradiation unit.

Further, in some aspects of the present invention, for the irradiation optical fiber and the light receiving optical fiber, a group delay time difference due to the wavelength dispersion of the light having the plurality of wavelengths 1 to q irradiated by the irradiation unit may be shorter than a propagation time corresponding to a peak of an optical propagation path length distribution of a layer closest to a surface among the plurality of light scattering medium layers.

A concentration determination method of the present invention using a concentration determination apparatus for determining a concentration of a target component in any layer of an observed object formed of a plurality of light scattering medium layers, the apparatus comprising an irradiation unit for irradiating short pulsed light to the observed object; a light receiving unit having a plurality of light receiving units for receiving light obtained as the short pulsed light is backscattered by the observed object; a selection unit for selecting a specific light receiving unit for receiving the light obtained as the short pulsed light is backscattered by the layer, from among the plurality of light receiving units; and an optical path length distribution storage unit for storing a model of an optical propagation path length distribution in each layer of the plurality of light scattering medium layers arranged on a light propagation path from the irradiation unit to the specific light receiving unit, of the short pulsed light irradiated to the observed object; and a time-resolved waveform storage unit for storing a model of a time-resolved waveform of the short pulsed light irradiated to the observed object and received by the specific light receiving unit, and a light intensity acquisition unit may acquire intensity of the light received by the specific light receiving unit at a given time since a time when the irradiation unit has irradiated the short pulsed light, an optical path length acquisition unit may acquire an optical path length of each of the plurality of light scattering medium layers, at the given time, of the model of the optical propagation path length distribution, from the optical path length distribution storage unit, a light intensity model acquisition unit may acquire the intensity of the light, at the given time, of the model of the time-resolved waveform of the short pulsed light, from the time-resolved waveform storage unit, an optical absorption coefficient calculation unit may calculate an optical absorption coefficient of the layer based on the light intensity acquired by the light intensity acquisition unit, the optical path length of each of the plurality of light scattering medium layers acquired by the optical path length acquisition unit, and the light intensity model acquired by the light intensity model acquisition unit, and a concentration calculation unit may calculate the concentration of the target component in the layer based on the optical absorption coefficient calculated by the optical absorption coefficient calculation unit.

A program of the present invention may cause a concentration determination apparatus for determining a concentration of a target component in any layer of an observed object formed of a plurality of light scattering medium layers, the apparatus comprising an irradiation unit for irradiating short pulsed light to the observed object; a light receiving unit having a plurality of light receiving units for receiving light obtained as the short pulsed light is backscattered by the observed object; a selection unit for selecting a specific light receiving unit for receiving the light obtained as the short pulsed light is backscattered by the layer, from among the plurality of light receiving units; an optical path length distribution storage unit for storing a model of an optical propagation path length distribution in each layer of the plurality of light scattering medium layers arranged on a light propagation path from the irradiation unit to the specific light receiving unit, of the short pulsed light irradiated to the observed object; and a time-resolved waveform storage unit for storing a model of a time-resolved waveform of the short pulsed light irradiated to the observed object and received by the specific light receiving unit, to operate as a light intensity acquisition unit for acquiring intensity of the light received by the specific light receiving unit at a given time since a time when the irradiation unit has irradiated the short pulsed light, an optical path length acquisition unit for acquiring an optical path length of each of the plurality of light scattering medium layers, at the given time, of the model of the optical propagation path length distribution, from the optical path length distribution storage unit, a light intensity model acquisition unit for acquiring the intensity of the light, at the given time, of the model of the time-resolved waveform of the short pulsed light, from the time-resolved waveform storage unit, an optical absorption coefficient calculation unit for calculating an optical absorption coefficient of the layer based on the light intensity acquired by the light intensity acquisition unit, the optical path length of each of the plurality of light scattering medium layers acquired by the optical path length acquisition unit and the light intensity model acquired by the light intensity model acquisition unit, and a concentration calculation unit for calculating the concentration of the target component in the layer based on the optical absorption coefficient calculated by the optical absorption coefficient calculation unit.

A concentration determination apparatus of the present invention for determining a concentration of a target component in any layer of an observed object including a plurality of light scattering medium layers may include an irradiation unit for irradiating light to the observed object; a light scattering medium layer selection unit for selecting backscattered light radiated from the layer from among plural types of backscattered light radiated from the observed object by irradiating the light; a light receiving unit for receiving the backscattered light radiated from the layer; a temperature measurement unit for measuring a temperature of the layer of the observed object; a light intensity acquisition unit for acquiring intensity of the backscattered light radiated from the layer received by the light receiving unit; an optical absorption coefficient calculation unit for calculating an optical absorption coefficient of the layer based on the light intensity acquired by the light intensity acquisition unit; a concentration calculation unit for calculating the concentration of the target component in the layer based on the optical absorption coefficient calculated by the optical absorption coefficient calculation unit; and a concentration correction unit for correcting the concentration of the target component calculated by the concentration calculation unit based on the temperature measured by the temperature measurement unit.

When the backscattered light radiated from any layer is received by the light receiving unit, a temperature of the layer is measured by the temperature measurement unit. Further, the concentration of a target component in any layer calculated by the concentration calculation unit is corrected by the concentration correction unit based on the temperature measured by the temperature measurement unit. Thus, it is possible to reduce effects of the temperature on the concentration of the target component in any layer of the observed object calculated based on the backscattered light by correcting the concentration of the target component calculated by the concentration calculation unit based on the temperature of the layer measured by the temperature measurement unit. Accordingly, it is possible to reduce effects of the temperature of any layer in the concentration of the target component and accurately measure the concentration of the target component in a non-invasive manner.

The concentration determination apparatus may use short pulsed light as the light, and may further include an optical path length distribution storage unit for storing a model of an optical propagation path length distribution in each of the plurality of light scattering medium layers, of the short pulsed light irradiated to the observed object; a time-resolved waveform storage unit for storing a model of a time-resolved waveform of the short pulsed light irradiated to the observed object; an optical path length acquisition unit for acquiring an optical path length of each of the plurality of light scattering medium layers, at the given time, of the model of the optical propagation path length distribution, from the optical path length distribution storage unit; and a light intensity model acquisition unit for acquiring the intensity of the light, at the given time, of the model of the time-resolved waveform of the short pulsed light, from the time-resolved waveform storage unit, and the light intensity acquisition unit may acquire light intensity, at a plurality of times $t_1$ to $t_m$, of the layer, and the optical absorption coefficient calculation unit may calculate an optical absorption coefficient of the layer using the following equation (1):

$$\begin{cases} N(t_1)\ln\left(\dfrac{N(t_1)}{I(t_1)}\right) = \sum_{i=1}^{n} \mu_i L_i(t_1) \\ \vdots \\ N(t_m)\ln\left(\dfrac{N(t_m)}{I(t_m)}\right) = \sum_{i=1}^{n} \mu_i L_i(t_m) \end{cases} \quad (1)$$

(where, I(t) denotes the intensity of the light received by the light receiving unit at time t, N(t) denotes the light intensity, at time t, of a non-absorption model of the time-resolved waveform of the short pulsed light, Li(t) denotes an optical path length of an i-th layer, at time t, of the model of the optical propagation path length distribution in each of the plurality of light scattering medium layers, and µi denotes an optical absorption coefficient of the i-th layer).

The light intensity acquisition unit acquires the light intensity, at a plurality of times $t_1$ to $t_m$ of the layer, and the optical absorption coefficient calculation unit calculates the optical absorption coefficient of the layer using Equation (1). Thus, it is possible to reduce the backscattered light from layers other than any layer as noise by performing time-resolved measurement on the backscattered light and reduce effects of the temperature in the concentration of the target component. Accordingly, it is also possible to accurately measure the concentration of the target component.

The concentration determination apparatus of the present invention may use short pulsed light as the light and may further include an optical path length distribution storage unit for storing a model of an optical propagation path length distribution in each of the plurality of light scattering medium layers, of the short pulsed light irradiated to the observed object; a time-resolved waveform storage unit for storing a model of a time-resolved waveform of the short pulsed light irradiated to the observed object; an optical path length acquisition unit for acquiring an optical path length of each of the plurality of light scattering medium layers, at the given time, of the model of the optical propagation path length distribution, from the optical path length distribution storage unit; and a light intensity model acquisition unit for acquiring the intensity of the light, at the given time, of the model of the time-resolved waveform of the short pulsed light, from the time-resolved waveform storage unit, and the light intensity acquisition unit may acquire light intensity between a given time and at least a given time t, and the optical absorption coefficient calculation unit may calculate an optical absorption coefficient of the layer using the following equation (2):

$$\begin{cases} \int_0^\tau \ln\left(\frac{N(t)}{I(t)}\right) L_1(t) dt = \sum_{i=1}^n \mu_i \int_0^\tau L_1(t) L_i(t_1) \, dt \\ \quad\quad\quad\quad\quad\quad \vdots \\ \int_0^\tau \ln\left(\frac{N(t)}{I(t)}\right) L_n(t) dt = \sum_{i=1}^n \mu_i \int_0^\tau L_n(t) L_i(t_1) \, dt \end{cases} \quad (2)$$

(where, I(t) denotes the intensity of the light received by the light receiving unit at time t, N(t) denotes the light intensity, at time t, of a non-absorption model of the time-resolved waveform of the short pulsed light, Li(t) denotes an optical path length of an i-th layer, at time t, of the model of the optical propagation path length distribution in each of the plurality of light scattering medium layers, n denotes the number of layers that are observed objects, and μi denotes an optical absorption coefficient of the i-th layer).

The light intensity acquisition unit acquires the light intensity between a given time and at least a given time τ, and the optical absorption coefficient calculation unit calculates the optical absorption coefficient of the layer using Equation (2). Thus, it is possible to reduce the backscattered light from layers other than any layer as noise by performing time-resolved measurement on the backscattered light and reduce effects of the temperature in the concentration of the target component. Accordingly, it is also possible to accurately measure the concentration of the target component.

In the concentration determination apparatus of the present invention, the concentration calculation unit may calculate the concentration of the target component in the layer using the following equation (3):

$$\begin{cases} \mu_{a(1)} - \mu_{a(2)} = \sum_{j=1}^p g_j(\varepsilon_{j(1)} - \varepsilon_{j(2)}) \\ \quad\quad\quad\quad\quad \vdots \\ \mu_{a(q-1)} - \mu_{a(q)} = \sum_{j=1}^p g_j(\varepsilon_{j(q-1)} - \varepsilon_{j(q)}) \end{cases} \quad (3)$$

(where, $\mu_a$ denotes an optical absorption coefficient in an a-th layer that is the layer, $g_j$ denotes a molar concentration of a j-th component constituting the observed object, $\varepsilon_j$ denotes an optical absorption coefficient of the j-th component, p denotes the number of main components constituting the observed object, and q denotes the number of types of the short pulsed light).

The concentration calculation unit calculates the concentration of the target component in the layer using Equation (3). Thus, it is possible to reduce effects of the temperature in the concentration of the target component by calculating the concentration of the target component in any layer using the backscattered light subjected to time-resolved measurement. Accordingly, it is also possible to accurately measure the concentration of the target component.

In the concentration determination apparatus of the present invention, the temperature measurement unit may include a surface temperature measurement unit for measuring a temperature of the vicinity of a surface of the observed object and an internal temperature measurement unit for measuring a temperature of the vicinity of the surface temperature measurement unit, and the concentration correction unit may correct the concentration of the target component calculated by the concentration calculation unit based on a difference between the temperature of the vicinity of the surface of the observed object measured by the surface temperature measurement unit and the temperature of the vicinity of the surface temperature measurement unit measured by the internal temperature measurement unit.

The temperature of the vicinity of a surface of the observed object is measured by the surface temperature measurement unit and the temperature of the vicinity of the surface temperature measurement unit measured by the internal temperature measurement unit. The concentration of the target component calculated by the concentration calculation unit is corrected by the concentration correction unit based on the difference between the temperature of the vicinity of the surface of the observed object measured by the surface temperature measurement unit and the temperature of the vicinity of the surface temperature measurement unit measured by the internal temperature measurement unit. Thus, it is possible to greatly reduce effects of the temperature on the concentration of a target component in any layer of the observed object calculated based on the backscattered light by correcting the concentration of the target component calculated by the concentration calculation unit by the concentration correction unit based on the difference between the temperature of the vicinity of the surface of the observed object measured by the surface temperature measurement unit and the temperature of the vicinity of the surface temperature measurement unit measured by the internal temperature measurement unit. Accordingly, it is possible to greatly reduce effects of the temperature of any layer in the concentration of the target component and accurately measure the concentration of the target component in a non-invasive manner.

In the concentration determination apparatus of the present invention, the temperature measurement unit may include a surface and internal temperature change rate calculation unit for calculating the difference between the temperature of the vicinity of the surface of the observed object measured by the surface temperature measurement unit and the temperature of the vicinity of the surface temperature measurement unit measured by the internal temperature measurement unit, as a temperature change rate per unit time.

The difference between the temperature of the vicinity of the surface of the observed object measured by the surface temperature measurement unit and the temperature of the vicinity of the surface temperature measurement unit measured by the internal temperature measurement unit is calculated as a temperature change rate per unit time by the surface and internal temperature change rate calculation unit. Thus, it is possible to greatly reduce effects of the temperature on the concentration of the target component in any layer of the observed object calculated based on the backscattered light by correcting the concentration of the target component calculated by the concentration calculation unit based on the temperature change rate per unit time calculated from the difference between the temperature of the vicinity of the surface of the observed object measured by the surface temperature measurement unit and the temperature of the vicinity of the surface temperature measurement unit measured by the internal temperature measurement unit. Accordingly, it is possible to accurately measure the concentration of the target component in a non-invasive manner.

In the concentration determination apparatus of the present invention, the temperature measurement unit may include a temperature adjustment means.

The temperature measurement unit is adjusted and held to a given temperature, for example, 36.0° C. by the temperature adjustment means. Accordingly, the temperature is not changed in the temperature measurement unit and the measurement accuracy of the temperature measurement unit is improved.

The concentration determination method of the present invention for determining a concentration of a target component in any layer of an observed object including a plurality of light scattering medium layers may include irradiating, by an irradiation unit, light to the observed object; measuring, by a temperature measurement unit, a temperature of the layer of the observed object; selecting, by a light scattering medium layer selection unit, backscattered light radiated from the layer from among plural types of backscattered light radiated from the observed object by irradiating the light; receiving, by a light receiving unit, the backscattered light radiated from the layer; acquiring, by a light intensity acquisition unit, intensity of the backscattered light radiated from the layer received by the light receiving unit; calculating, by an optical absorption coefficient calculation unit, an optical absorption coefficient of the layer based on the light intensity acquired by the light intensity acquisition unit; calculating, by a concentration calculation unit, the concentration of the target component in the layer based on the optical absorption coefficient calculated by the optical absorption coefficient calculation unit; and correcting, by a concentration correction unit, the concentration of the target component calculated by the concentration calculation unit based on the temperature measured by the temperature measurement unit.

The temperature of the layer of the observed object is measured by a temperature measurement unit and the concentration of the target component in the layer is calculated by the concentration calculation unit based on the optical absorption coefficient calculated by the optical absorption coefficient calculation unit, and the concentration of the target component calculated by the concentration calculation unit is corrected by the concentration correction unit based on the temperature measured by the temperature measurement unit. It is possible to reduce effects of the temperature of any layer even in the concentration of the target component in any layer of the observed object by correcting, by the concentration correction unit, the concentration of the target component calculated by the concentration calculation unit based on the temperature measured by the temperature measurement unit. Accordingly, it is possible to reduce effects of the temperature of any layer in the concentration of the target component and accurately and efficiently the concentration of the target component in a non-invasive manner.

A program of the present invention may cause a computer of a concentration determination apparatus for determining a concentration of a target component in any layer of an observed object including a plurality of light scattering medium layers to execute an irradiation process of irradiating light to the observed object; a temperature measurement process of measuring a temperature of the layer of the observed object; a light scattering medium layer selection process of selecting backscattered light radiated from the layer from among plural types of backscattered light radiated from the observed object by irradiating the light; a light receiving process of receiving the backscattered light radiated from the layer; a light intensity acquisition process of acquiring intensity of the backscattered light radiated from the layer obtained in the light receiving process; an optical absorption coefficient calculation process of calculating an optical absorption coefficient of the layer based on the light intensity acquired in the light intensity acquisition process; a concentration calculation process of calculating the concentration of the target component in the layer based on the optical absorption coefficient calculated in the optical absorption coefficient calculation process; and a concentration correction process of correcting the concentration of the target component calculated in the concentration calculation process based on the temperature obtained in the temperature measurement process.

The computer of the concentration determination apparatus is caused to execute the temperature measurement process of measuring the temperature of the layer of the observed object and the concentration correction process of correcting the concentration of the target component calculated in the concentration calculation process based on the temperature obtained in the temperature measurement process. Thus, it is possible to reduce effects of the temperature in the backscattered light radiated from any layer by executing the temperature measurement process of measuring the temperature of the layer of the observed object and the concentration correction process of correcting the concentration of the target component calculated in the concentration calculation process based on the temperature obtained in the temperature measurement process, and it is possible to reduce effects of the temperature of any layer even in the concentration of a target component in any layer of the observed object calculated based on the backscattered light. Accordingly, it is possible to reduce effects of the temperature of any layer in the concentration of the target component and accurately and efficiently the concentration of the target component in a non-invasive manner.

A concentration determination apparatus for determining a concentration of a target component in any layer of an observed object including a plurality of light scattering medium layers in a living body may include a pulse wave detection unit for detecting, over a given area, pulse pressure of the vicinity of a portion having a beat in the living body; a temperature measurement unit provided near the pulse wave detection unit for measuring a temperature over the given area; a body temperature specifying unit for specifying a temperature of a portion from which a maximum pulse pressure among the pulse pressures detected over the given area is detected, as the body temperature of the living body; an irradiation unit for irradiating light to the observed object; a light scattering medium layer selection unit for selecting backscattered light radiated from the layer from among plural types of backscattered light radiated from the observed object by irradiating the light; a light receiving unit for receiving the backscattered light radiated from the layer; a light intensity acquisition unit for acquiring intensity of the backscattered light radiated from the layer received by the light receiving unit; an optical absorption coefficient calculation unit for calculating an optical absorption coefficient of the layer based on the light intensity acquired by the light intensity acquisition unit; a concentration calculation unit for calculating the concentration of the target component in the layer based on the optical absorption coefficient calculated by the optical absorption coefficient calculation unit; and a concentration correction unit for correcting the concentration of the target component calculated by the concentration calculation unit based on the body temperature specified by the body temperature specifying unit.

The pulse pressure of the vicinity of a portion having a beat in the living body is detected over a given area by the pulse wave detection unit, the temperature is measured over the given area by the temperature measurement unit, and the temperature of a portion from which a maximum pulse pressure among the pulse pressures detected over the given area is detected is specified as the body temperature of the living body by the body temperature specifying unit. Further, the concentration of the target component calculated by the concentration calculation unit is corrected by the concentration correction unit based on the body temperature specified by the body temperature specifying unit. Thus, it is possible to accurately detect the concentration of a target component in any layer of the observed object calculated based on the backscattered light according to the active state of the living body by specifying the body temperature similar to the deep-portion temperature of the living body and correcting the calculated concentration of the target component based on the pulse wave detection unit, the temperature measurement unit and the body temperature specifying unit. Accordingly, it is possible to accurately measure the concentration of the target component in any layer of the observed object according to the active state of the living body in a non-invasive manner and in a short time.

A concentration determination apparatus of the present invention for determining a concentration of a target component in any layer of an observed object including a plurality of light scattering medium layers in a living body may include a pulse wave detection unit for detecting, over a given area, pulse pressure of the vicinity of a portion having a beat in the living body; a temperature measurement unit including a surface temperature measurement unit for measuring a temperature of the vicinity of a surface of the observed object and a sensor internal temperature measurement unit for measuring a temperature of the vicinity of the surface temperature measurement unit; an irradiation unit for irradiating light to the observed object; a light scattering medium layer selection unit for selecting backscattered light radiated from the layer from among plural types of backscattered light radiated from the observed object by irradiating the light; a light receiving unit for receiving the backscattered light radiated from the layer; a light intensity acquisition unit for acquiring intensity of the backscattered light radiated from the layer received by the light receiving unit; an optical absorption coefficient calculation unit for calculating an optical absorption coefficient of the layer based on the light intensity acquired by the light intensity acquisition unit; a concentration calculation unit for calculating the concentration of the target component in the layer based on the optical absorption coefficient calculated by the optical absorption coefficient calculation unit; and a concentration correction unit for correcting the concentration of the target component calculated by the concentration calculation unit based on a difference between the temperature of the vicinity of the surface of the observed object measured by the surface temperature measurement unit and the temperature of the vicinity of the surface temperature measurement unit measured by the sensor internal temperature measurement unit.

In the concentration determination apparatus of the present invention, the pulse pressure of the vicinity of a portion having a beat in the living body is detected over a given area by the pulse wave detection unit, the temperature of the vicinity of the surface of the observed object is measured by the surface temperature measurement unit, and the temperature of the vicinity of the surface temperature measurement unit is detected by the sensor internal temperature measurement unit. Further, the concentration of the target component calculated by the concentration calculation unit is corrected by the concentration correction unit based on the difference between the temperature of the vicinity of the surface of the observed object measured by the surface temperature measurement unit and the temperature of the vicinity of the surface temperature measurement unit measured by the sensor internal temperature measurement unit. It is possible to accurately detect the concentration of the target component in any layer of the observed object calculated based on the backscattered light by performing the above correction. Accordingly, it is possible to accurately measure the concentration of the target component in any layer of the observed object in a non-invasive manner and in a short time.

The concentration determination apparatus may use short pulsed light as the light, and may include an optical path length distribution storage unit for storing a model of an optical propagation path length distribution in each of the plurality of light scattering medium layers, of the short pulsed light irradiated to the observed object; a time-resolved waveform storage unit for storing a model of a time-resolved waveform of the short pulsed light irradiated to the observed object; an optical path length acquisition unit for acquiring an optical path length of each of the plurality of light scattering medium layers, at the given time, of the model of the optical propagation path length distribution, from the optical path length distribution storage unit; and a light intensity model acquisition unit for acquiring the intensity of the light, at the given time, of the model of the time-resolved waveform of the short pulsed light, from the time-resolved waveform storage unit, and the light intensity acquisition unit may acquire light intensity, at a plurality of times $t_1$ to $t_m$, of the layer, and the optical absorption coefficient calculation unit may calculate the optical absorption coefficient of the layer using the following equation (1):

$$\begin{cases} N(t_1)\ln\left(\dfrac{N(t_1)}{I(t_1)}\right) = \sum_{i=1}^{n} \mu_i L_i(t_1) \\ \vdots \\ N(t_m)\ln\left(\dfrac{N(t_m)}{I(t_m)}\right) = \sum_{i=1}^{n} \mu_i L_i(t_m) \end{cases} \quad (1)$$

(where, I(t) denotes the intensity of the light received by the light receiving unit at time t, N(t) denotes the light intensity, at time t, of the model of the time-resolved waveform of the short pulsed light, Li(t) denotes an optical path length of an i-th layer, at time t, of the model of the optical propagation path length distribution in each of the plurality of light scattering medium layers, and μi denotes an optical absorption coefficient of the i-th layer).

In the concentration determination apparatus of the present invention, the light intensity acquisition unit acquires the light intensity, at a plurality of times $t_1$ to $t_m$, of the layer, and the optical absorption coefficient calculation unit calculates the optical absorption coefficient of the layer using Equation (1). Thus, by performing time-resolved measurement on the backscattered light, it is possible to reduce the backscattered light from layers other than any layer as noise and reduce effects of the temperature of each layer on the concentration of the target component. Accordingly, it is also possible to accurately measure the concentration of the target component.

The concentration determination apparatus may use short pulsed light as the light, and may include an optical path length distribution storage unit for storing a model of an optical propagation path length distribution in each of the plurality of light scattering medium layers, of the short pulsed light irradiated to the observed object; a time-resolved waveform storage unit for storing a model of a time-resolved waveform of the short pulsed light irradiated to the observed object; an optical path length acquisition unit for acquiring an optical path length of each of the plurality of light scattering medium layers, at the given time, of the model of the optical propagation path length distribution, from the optical path length distribution storage unit; and a light intensity model acquisition unit for acquiring the intensity of the light, at the given time, of the model of the time-resolved waveform of the short pulsed light, from the time-resolved waveform storage unit, and the light intensity acquisition unit may acquire light intensity between a given time and at least a given time τ, and the optical absorption coefficient calculation unit may calculate the optical absorption coefficient of the layer using the following equation (2):

$$\begin{cases} \int_0^\tau \ln\left(\frac{N(t)}{I(t)}\right) L_1(t) dt = \sum_{i=1}^n \mu_i \int_0^\tau L_1(t) L_i(t_1) dt \\ \vdots \\ \int_0^\tau \ln\left(\frac{N(t)}{I(t)}\right) L_n(t) dt = \sum_{i=1}^n \mu_i \int_0^\tau L_n(t) L_i(t_1) dt \end{cases} \quad (2)$$

(where, I(t) denotes the intensity of the light received by the light receiving unit at time t, N(t) denotes the light intensity, at time t, of the model of the time-resolved waveform of the short pulsed light, Li(t) denotes an optical path length of an i-th layer, at time t, of the model of the optical propagation path length distribution in each of the plurality of light scattering medium layers, n denotes the number of layers that are observed objects, and pi denotes an optical absorption coefficient of the i-th layer).

In the concentration determination apparatus of the present invention, the light intensity acquisition unit acquires the light intensity between a given time and at least a given time τ, and the optical absorption coefficient calculation unit calculates the optical absorption coefficient of the layer using Equation (2). Thus, it is possible to reduce the backscattered light from layers other than any layer as noise and reduce effects of the temperature of each layer on the concentration of the target component by performing time-resolved measurement on the backscattered light. Accordingly, it is also possible to accurately measure the concentration of the target component.

In the concentration determination apparatus of the present invention, the concentration calculation unit may calculate the concentration of the target component in the layer using the following equation (3):

$$\begin{cases} \mu_{a(1)} - \mu_{a(2)} = \sum_{j=1}^p g_j(\varepsilon_{j(1)} - \varepsilon_{j(2)}) \\ \vdots \\ \mu_{a(q-1)} - \mu_{a(q)} = \sum_{j=1}^p g_j(\varepsilon_{j(q-1)} - \varepsilon_{j(q)}) \end{cases} \quad (3)$$

(where, $\mu_a$ denotes an optical absorption coefficient in an a-th layer that is the layer, $g_j$ denotes a molar concentration of a j-th component constituting the observed object, $\varepsilon_j$ denotes an optical absorption coefficient of the j-th component, p denotes the number of main components constituting the observed object, and q denotes the number of types of the short pulsed light).

In the concentration determination apparatus of the present invention, the concentration calculation unit calculates the concentration of the target component in the layer using Equation (3). Thus, it is possible to reduce the effects of the temperature of each layer on the concentration of the target component by calculating the concentration of the target component in any layer using the backscattered light subjected to time-resolved measurement. Accordingly, it is also possible to accurately measure the concentration of the target component.

The concentration determination apparatus of the present invention may include a plurality of sets of pulse wave detection units and temperature measurement units, and the body temperature specifying unit may specify, as the body temperature, a temperature measured by the temperature measurement unit near the pulse wave detection unit corresponding to a portion from which a maximum pulse pressure is detected among the plurality of pulse wave detection units.

The temperature measured by the temperature measurement unit near the pulse wave detection unit corresponding to the portion from which the maximum pulse pressure is detected among the plurality of pulse wave detection units is specified as the body temperature. Thus, it is possible to measure the body temperature of a portion that is an observed object of the living body in a short time through minimal manipulation by using the plurality of sets of pulse wave detection units and temperature measurement units.

In the concentration determination apparatus of the present invention, the temperature measurement unit may include a surface and internal temperature change rate calculation unit for calculating the difference between the temperature of the vicinity of the surface of the observed object measured by the surface temperature measurement unit and the temperature of the vicinity of the surface temperature measurement unit measured by the sensor internal temperature measurement unit, as a temperature change rate per unit time.

The difference between the temperature of the vicinity of the surface of the observed object measured by the surface temperature measurement unit and the temperature of the vicinity of the surface temperature measurement unit measured by the internal temperature measurement unit is calculated as the temperature change rate per unit time by the surface and internal temperature change rate calculation unit. Thus, it is possible to greatly reduce effects of the temperature on the concentration of the target component in any layer of the observed object calculated based on the backscattered light by correcting the concentration of a target component calculated by the concentration calculation unit based on the temperature change rate per unit time calculated from the difference between the temperature of the vicinity of the surface of the observed object measured by the surface temperature measurement unit and the temperature of the vicinity of the surface temperature measurement unit measured by the sensor internal temperature measurement unit. Thus, it is possible to accurately measure the concentration of the target component in a non-invasive manner.

In the concentration determination apparatus, the pulse wave detection unit may include a beat judgment unit for judging whether the pulse wave detection unit is detecting a pulse pressure.

It is possible to reliably recognize whether the pulse wave detection unit is detecting the pulse pressure and prevent misunderstanding of the detection of the pulse pressure by providing the pulse wave detection unit with the beat judgment unit for judging whether the pulse wave detection unit is detecting a pulse pressure.

The concentration determination apparatus may include a body motion detection unit for detecting a body motion of the living body; and a body motion judgment means for judging whether the body motion of the living body detected by the body motion detection unit is within a given range.

When the body motion detection unit detects the body motion of the living body and the body motion judgment means judges whether the body motion of the living body detected by the body motion detection unit is within the given range, the body temperature of the living body is specified, thereby accurately recognizing the stable state of the living body. Accordingly, it is possible to accurately detect the concentration of the target component in any layer of the observed object in the stable state of the living body.

A probe of the present invention may include a pulse wave detection unit for detecting, over a given area, pulse pressure of the vicinity of a portion having a beat in the living body; a temperature measurement unit provided near the pulse wave detection unit for measuring a temperature over the given area; an irradiation unit for irradiating light to the observed object; a light scattering medium layer selection unit for selecting backscattered light radiated from any layer from among plural types of backscattered light radiated from the observed object by irradiating the light; and a light receiving unit for receiving the backscattered light radiated from the layer.

The pulse pressure of the vicinity of a portion having a beat in the living body is detected over a given area by the pulse wave detection unit, the temperature is measured over the given area by the temperature measurement unit, light is irradiated to the observed object by the irradiation unit, selecting backscattered light radiated from the layer is selected from among plural types of backscattered light radiated from the observed object by irradiating the light by the light scattering medium layer selection unit, and the backscattered light radiated from the layer is received by the light receiving unit. Thus, it is possible to efficiently and easily obtain the body temperature of the observed object of the living body and the backscattered light radiated from any layer of the observed object.

A concentration determination method of the present invention for determining a concentration of a target component in any layer of an observed object including a plurality of light scattering medium layers in a living body may include detecting, by a pulse wave detection unit, over a given area, pulse pressure of the vicinity of a portion having a beat in the living body and measuring, by a temperature measurement unit, a temperature over the given area; specifying, by a body temperature specifying unit, a temperature of a portion from which a maximum pulse pressure among the pulse pressures detected over the given area is detected, as a body temperature of the living body; irradiating, by an irradiation unit, light to the observed object; selecting, by a light scattering medium layer selection unit, backscattered light radiated from the layer from among plural types of backscattered light radiated from the observed object by irradiating the light; receiving, by a light receiving unit, the backscattered light radiated from the layer; acquiring, by a light intensity acquisition unit, intensity of the backscattered light radiated from the layer received by the light receiving unit; calculating, by an optical absorption coefficient calculation unit, an optical absorption coefficient of the layer based on the light intensity acquired by the light intensity acquisition unit; calculating, by a concentration calculation unit, the concentration of the target component in the layer based on the optical absorption coefficient calculated by the optical absorption coefficient calculation unit; and correcting, by a concentration correction unit, the concentration of the target component calculated by the concentration calculation unit based on the body temperature specified by the body temperature specifying unit.

The pulse pressure of the vicinity of a portion having a beat in the living body is detected over a given area by the pulse wave detection unit, the temperature is measured over the given area by the temperature measurement unit, and the temperature of a portion from which a maximum pulse pressure among the pulse pressures detected over the given area is detected is specified as the body temperature of the living body by the body temperature specifying unit. Thus, it is possible to accurately detect a concentration of a target component in any layer of the observed object according to the active state of the living body by specifying the body temperature similar to the deep-portion temperature of the living body and correcting the calculated concentration of the target component based on the body temperature. Accordingly, it is possible to accurately measure a concentration of a target component in any layer of the observed object according to the active state of the living body in a non-invasive manner and in a short time.

A program of the present invention may cause a computer of a concentration determination apparatus for determining a concentration of a target component in any layer of an observed object including a plurality of light scattering medium layers in a living body to execute a pulse wave detection process of detecting, over a given area, pulse pressure of the vicinity of a portion having a beat in the living body; a temperature measurement process of measuring a temperature over the given area; a body temperature specifying process of specifying a temperature of a portion from which a maximum pulse pressure among the pulse pressures detected over the given area is detected, as a body temperature of the living body; an irradiation process of irradiating light to the observed object; a light scattering medium layer selection process of selecting backscattered light radiated from the layer from among plural types of backscattered light radiated from the observed object by irradiating the light; a light receiving process of receiving the backscattered light radiated from the layer; a light intensity acquisition process of acquiring intensity of the backscattered light radiated from the layer received in the light receiving process; an optical absorption coefficient calculation process of calculating an optical absorption coefficient of the layer based on the light intensity acquired in the light intensity acquisition process; a concentration calculation process of calculating the concentration of the target component in the layer based on the optical absorption coefficient calculated in the optical absorption coefficient calculation process; and a concentration correction process of correcting the concentration of the target component calculated in the concentration calculation process based on the body temperature specified in the body temperature specifying process.

The computer of the concentration determination apparatus is caused to execute the pulse wave detection process of detecting, over a given area, pulse pressure of the vicinity of a portion having a beat in the living body, the temperature measurement process of measuring the temperature over a given area, and the body temperature specifying process of specifying a temperature of a portion from which a maximum pulse pressure among the pulse pressures detected over the given area is detected, as the body temperature of the living body. Thus, the body temperature similar to the deep-portion temperature of the living body can be specified by executing the pulse wave detection process, the temperature measurement process and body the temperature specifying process, and then the concentration of the target component can be accurately corrected based on the specified body temperature. Accordingly, it is possible to accurately measure the concentration of the target component in any layer of the observed object according to the active state of the living body in a non-invasive manner and in a short time.

DESCRIPTION OF EXEMPLARY EMBODIMENTS

Modes for embodying a concentration determination apparatus, a concentration determination method, and a program of the present invention will be described.

In the present invention, a description will be given in which a blood sugar value measurement apparatus is used as a concentration determination apparatus, skin of a person's palm is used as an observed object, glucose is used as a target component, and short pulsed light having a specific wavelength is used as light having a specific wavelength.
(First Embodiment)

Figure 1:
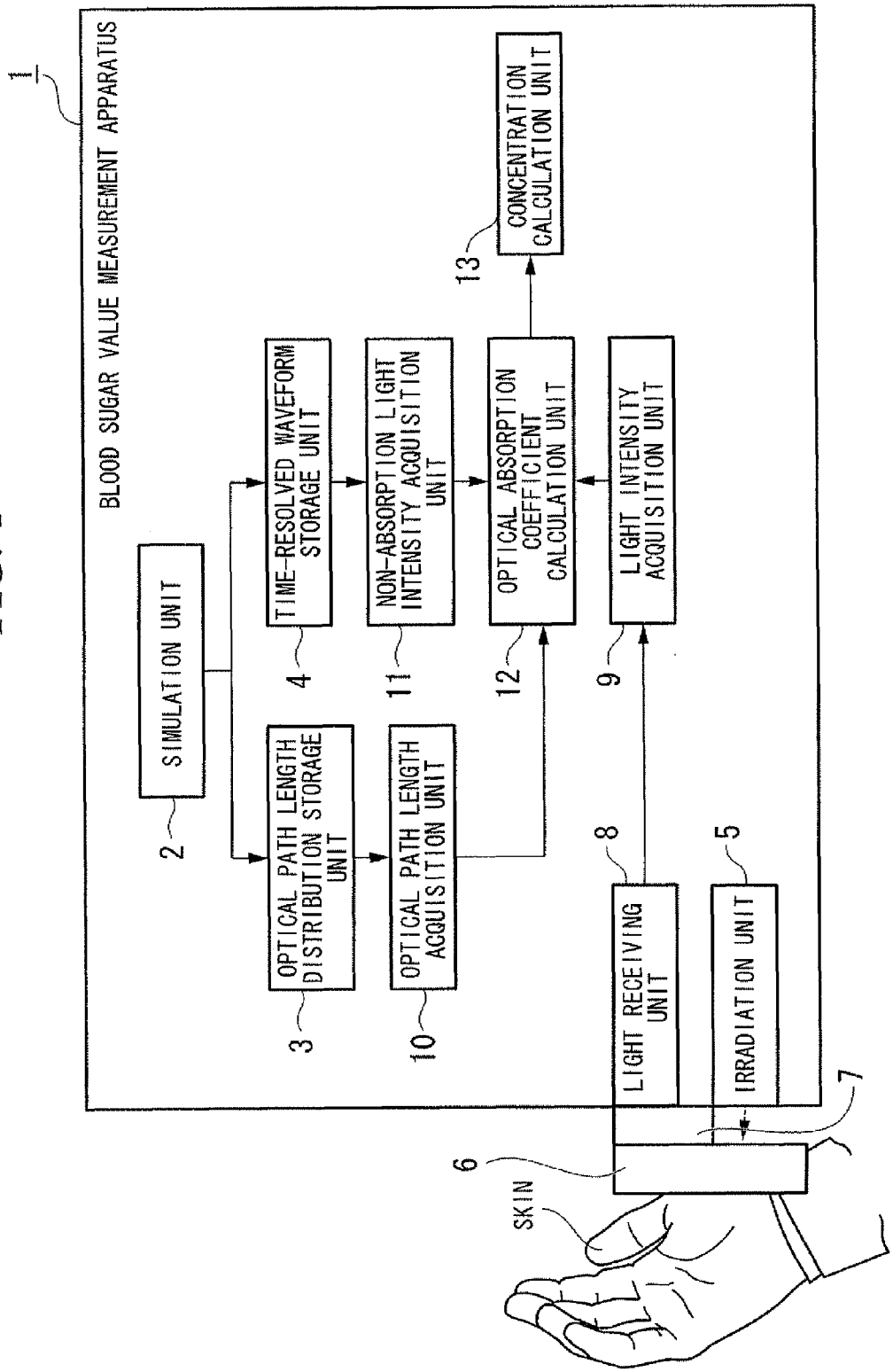
FIG. 1 is a schematic block diagram showing a configuration of a blood sugar value measurement apparatus of a first embodiment of the present invention.

FIG. 1 is a schematic block diagram showing a configuration of a blood sugar value measurement apparatus of a first embodiment of the present invention.

The blood sugar value measurement apparatus 1 noninvasively determines a concentration of glucose (a target component) contained in a dermis (any layer) among a plurality of layers constituting skin (an observed object) of, for example, a palm. The blood sugar value measurement apparatus 1 includes a simulation unit 2, an optical path length distribution storage unit 3, a time-resolved waveform storage unit 4, an irradiation unit 5, a light guide unit 6, a light scattering medium layer selection unit 7, a light receiving unit 8, a light intensity acquisition unit 9, an optical path length acquisition unit 10, a non-absorption light intensity acquisition unit (light intensity model acquisition unit) 11, an optical absorption coefficient calculation unit 12, and a concentration calculation unit 13.

The simulation unit 2 performs simulation for irradiating light to a skin model having an optical absorption coefficient of 0.

The optical path length distribution storage unit 3 stores a model of an optical propagation path length distribution in each layer constituting the skin, of short pulsed light irradiated to the skin. Here, the optical path length distribution storage unit 3 stores the optical propagation path length distribution of the skin model having an optical absorption coefficient of 0.

The time-resolved waveform storage unit 4 stores a model of a time-resolved waveform of the short pulsed light irradiated to the skin. Here, the time-resolved waveform storage unit 4 stores the time-resolved waveform of the skin model having the optical absorption coefficient of 0.

The irradiation unit 5 irradiates, to the skin, short pulsed light having a specific wavelength $\lambda_k(\lambda_1, \lambda_2 \ldots)$ at which a temperature change of the absorption coefficient of water in the dermis constituting the skin is small. Here, the short pulsed light refers to pulsed light having a pulse width of about 100 psec or less. Alternatively, pulsed light having a pulse width in a range of 0.1 psec to a few psec may be used as the short pulsed light.

The light guide unit 6 focuses plural types of backscattered light radiated from the skin by irradiating the short pulsed light having the specific wavelength $\lambda_k$ to the skin and guides the light to the light scattering medium layer selection unit 7.

The light scattering medium layer selection unit 7 selects backscattered light radiated by the dermis from among the plural types of backscattered light radiated from the skin, which have been focused and guided by the light guide unit 6, based on a relationship between a distance between an input and an output and an arrival distance in a depth direction in a living body.

The light receiving unit 8 receives light obtained as the short pulsed light is backscattered by the skin.

The light intensity acquisition unit 9 acquires light reception intensities at a plurality of different times, of the backscattered light radiated from the dermis, which has been received by the light receiving unit 8. Here, the plurality of times preferably include a peak time of the optical propagation path length distribution of each layer constituting the skin (the observed object). Thus, the inclusion of the peak time of the optical propagation path length distribution of each layer enables any layer from the plurality of layers of the skin, for example, the dermis, to be efficiently selected.

The optical path length acquisition unit 10 acquires an optical path length of each layer of the skin at a given time, of a model of the optical propagation path length distribution from the optical path length distribution storage unit 3. Here, the optical path length acquisition unit 10 acquires the optical path length at any time from the optical path length distribution storage unit 3.

The non-absorption light intensity acquisition unit 11 acquires light intensity, at a given time, of the model of the time-resolved waveform of the short pulsed light from the time-resolved waveform storage unit 4. Here, the non-absorption light intensity acquisition unit 11 acquires light intensity at any time from the time-resolved waveform storage unit 4.

The optical absorption coefficient calculation unit 12 calculates the optical absorption coefficient in the dermis of the skin, to which the short pulsed light having the specific wavelength $\lambda_k$ has been irradiated.

The optical absorption coefficient calculation unit 12 calculates an optical absorption coefficient of any layer in the skin using the following equation (4)

$$\begin{cases} N(t_1)\ln\left(\dfrac{N(t_1)}{I(t_1)}\right) = \sum_{i=1}^{n} \mu_i L_i(t_1) \\ \quad\vdots \\ N(t_m)\ln\left(\dfrac{N(t_m)}{I(t_m)}\right) = \sum_{i=1}^{n} \mu_i L_i(t_m) \end{cases} \quad (4)$$

(where I(t) denotes the light intensity of light received by the light receiving unit 8 at time t, N(t) denotes the light intensity, at time t, of the model of the time-resolved waveform of the short pulsed light having the specific wavelength $\lambda_k$, Li(t) denotes an optical path length of an i-th layer, at time t, of the model of the optical propagation path length distribution in each layer of the skin, and $\mu_i$ denotes an optical absorption coefficient of the i-th layer).

Here, the first layer is an epidermis, the second layer is a dermis, the third layer is subcutaneous tissue, $\mu_1$ denotes an optical absorption coefficient of the epidermis, $\mu_2$ denotes an optical absorption coefficient of the dermis, and $\mu_3$ denotes an optical absorption coefficient of the subcutaneous tissue.

The concentration calculation unit 13 calculates a concentration of the glucose contained in the dermis from the optical absorption coefficient in the dermis.

The concentration calculation unit 13 calculates the glucose concentration in any layer of the skin using the following equation (5):

$$\begin{cases} \mu_{a(1)} - \mu_{a(2)} = \sum_{j=1}^{p} g_j(\varepsilon_{j(1)} - \varepsilon_{j(2)}) \\ \quad\vdots \\ \mu_{a(q-1)} - \mu_{a(q)} = \sum_{j=1}^{p} g_j(\varepsilon_{j(q-1)} - \varepsilon_{j(q)}) \end{cases} \quad (5)$$

(where $\mu_a$ denotes an optical absorption coefficient in an a-th layer that is the layer of the skin, $g_j$ denotes a molar concentration of a-th component constituting the skin, $\varepsilon_j$ denotes an optical absorption coefficient of the j-th component, p denotes the number of main components constituting the skin and q denotes the number of types of a specific wavelength $\lambda_k$).

Here, the first layer is an epidermis, the second layer is a dermis, the third layer is subcutaneous tissue, $\mu_1$ denotes an optical absorption coefficient of the epidermis, $\mu_2$ denotes an optical absorption coefficient of the dermis, and $\mu_3$ denotes an optical absorption coefficient of the subcutaneous tissue.

In the blood sugar value measurement apparatus 1, the irradiation unit 5 irradiates, to the skin 21, short pulsed light having a specific wavelength $\lambda_k$ at which a temperature change of the absorption coefficient of the water in the dermis 230 constituting the skin 21 is small, such as $\lambda_1$=1445 nm or $\lambda_2$=1782 nm.

The light guide unit 6 focuses plural types of backscattered light radiated from the skin 21. The light scattering medium layer selection unit 7 selects backscattered light radiated by the dermis 230 from among the plural types of backscattered light radiated from the skin 21 based on a relationship between a distance between an input and an output and an arrival distance in a depth direction in a living body.

The light receiving unit 8 receives a signal light including more backscattered light radiated from the dermis 230.

The light intensity acquisition unit 9 acquires light intensity of the backscattered light radiated from the dermis 230, which has been received by the light receiving unit 8 at time t.

The optical path length acquisition unit 10 acquires an optical path length of each layer of the skin, at time t, of the optical propagation path length distribution in the skin model from the optical path length distribution storage unit 3.

The non-absorption light intensity acquisition unit 11 acquires light intensity, at time t, of a time-resolved waveform of the short pulsed light in the skin model from the time-resolved waveform storage unit 4.

The optical absorption coefficient calculation unit 12 calculates an optical absorption coefficient of the dermis of the skin based on the light intensity acquired from the light intensity acquisition unit 9, the optical path length of each layer of the skin acquired by the optical path length acquisition unit 10, and the light intensity acquired by the non-absorption light intensity acquisition unit 11.

The concentration calculation unit 13 calculates concentration of the glucose contained in the dermis 230 based on the optical absorption coefficient calculated by the optical absorption coefficient calculation unit 12 based on Equation (5).

Accordingly, it is possible to reduce effects of noise due to layers other than the dermis and calculate the concentration of the glucose contained in the dermis.

Thus, it is possible to reduce effects of the water in the backscattered light radiated from the dermis 230 and also to reduce effects of the water in the concentration of the glucose contained in the dermis 230 calculated based on the backscattered light. Accordingly, it is possible to reduce the effects of the water in the glucose concentration and to accurately measure the concentration of the glucose contained in the dermis 230 in a non-invasive manner.

Next, operation of the blood sugar value measurement apparatus 1 will be described.

The blood sugar value measurement apparatus 1 should calculate the optical propagation path length distribution and the time-resolved waveform in each layer of the skin model in advance before measuring the blood sugar value.

Figure 2:
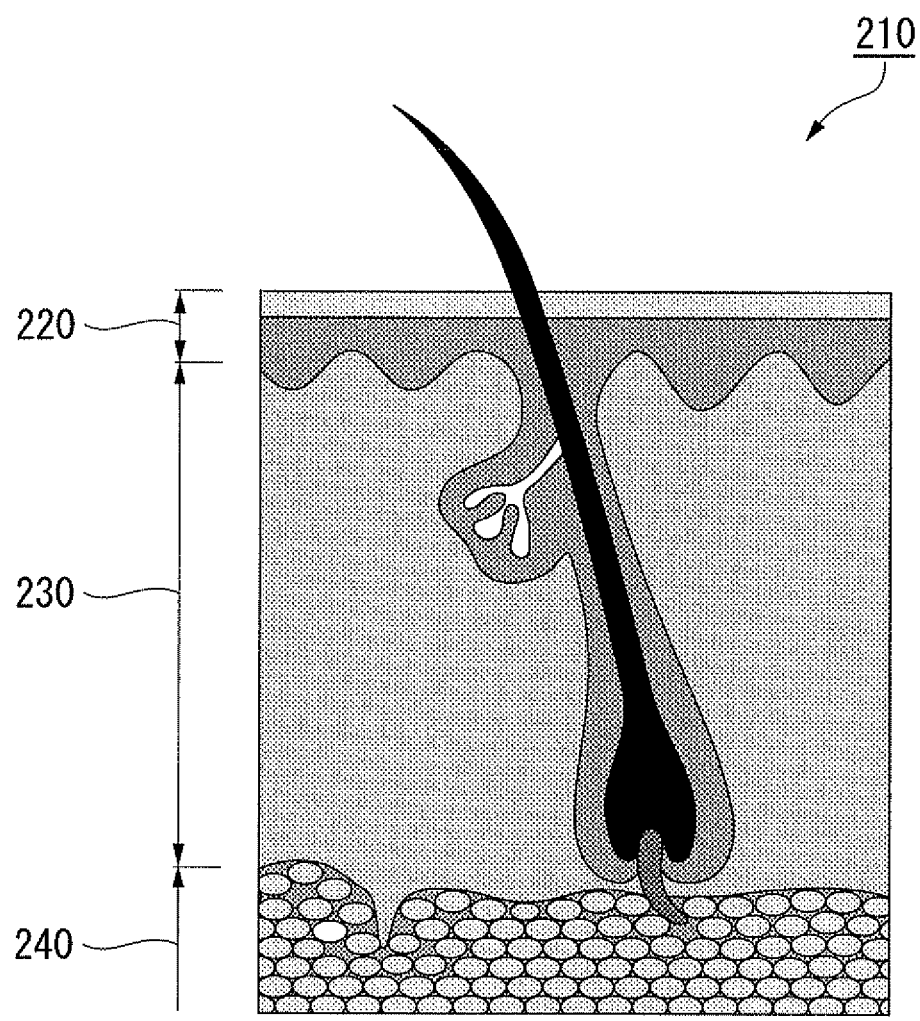
FIG. 2 is a schematic diagram showing a cross-sectional structure of skin.

FIG. 2 is a schematic diagram showing a cross-section of skin tissue of a human. Skin 210 includes an epidermis 220 having a thickness of about 0.3 mm, which is substantially 20% water and a remaining portion of which is protein, a dermis (any layer) 230 having a thickness of about 1.2 mm, which is formed beneath the epidermis 220 and contains substantially 60% water, protein, lipid and glucose, and a subcutaneous tissue 240 having a thickness of about 3.0 mm, which is formed beneath the dermis 230 and contains substantially 90% or more lipid of and water as a remaining portion Here, a method of calculating the optical propagation path length distribution and the time-resolved waveform of the skin model will be described.

Initially, the simulation unit 2 generates a skin model. The skin model generation is performed by determining a light scattering coefficient, an optical absorption coefficient and a thickness of each layer of the skin. Here, the scattering coefficient and the thickness of each layer of the skin may be determined by taking a sample in advance since a difference from entity to entity is small.

Further, the optical absorption coefficient of the skin model used herein is 0. This is because a light absorption amount is calculated using the skin model.

When the simulation unit 2 generates a skin model, a simulation is performed for irradiating light to the skin model. In this case, it is necessary to determine a distance between a position of the irradiation unit 5 and a position of the light receiving unit 8. The simulation may be performed using a Monte Carlo method. For example, the simulation using the Monte Carlo method is performed as follows.

First, the simulation unit 2 performs calculation using photons (beams) as a model of an irradiation light and irradiates the photons to the skin model. The photons irradiated to the skin model move into the skin model. In this case, for the photons, a distance L and a direction θ to a point to which the photons go next are determined by a random number R. The simulation unit 2 calculates a distance L to a point to which the photons go next, using Equation (6):

$$L = \ln(R/\mu_s) \quad (6)$$

where $\mu_s$ denotes a scattering coefficient of the s-th layer (any one of the epidermis, the dermis, and the subcutaneous tissue layer) of the skin model.

Further, the simulation unit 2 calculates the direction θ to a point to which the photons go next using Equation (7):

$$\theta = \cos^{-1}\left[\frac{1}{2g}\left\{1 + g^2 - \left(\frac{1-g^2}{1+g-2gR}\right)^2\right\}\right] \quad (7)$$

where g denotes an anisotropy parameter that is an average of a cosine (cos) of a scattering angle and the anisotropy parameter of the skin is about 0.9.

The simulation unit 2 may calculate a photon movement path from the irradiation unit 5 to the light receiving unit 8 by iteratively performing the calculations of Equations (6) and (7) per unit time. The simulation unit 2 performs calculation of the movement distance on a plurality of photons. For example, the simulation unit 2 calculates movement distance of $10^8$ photons.

Figure 3:
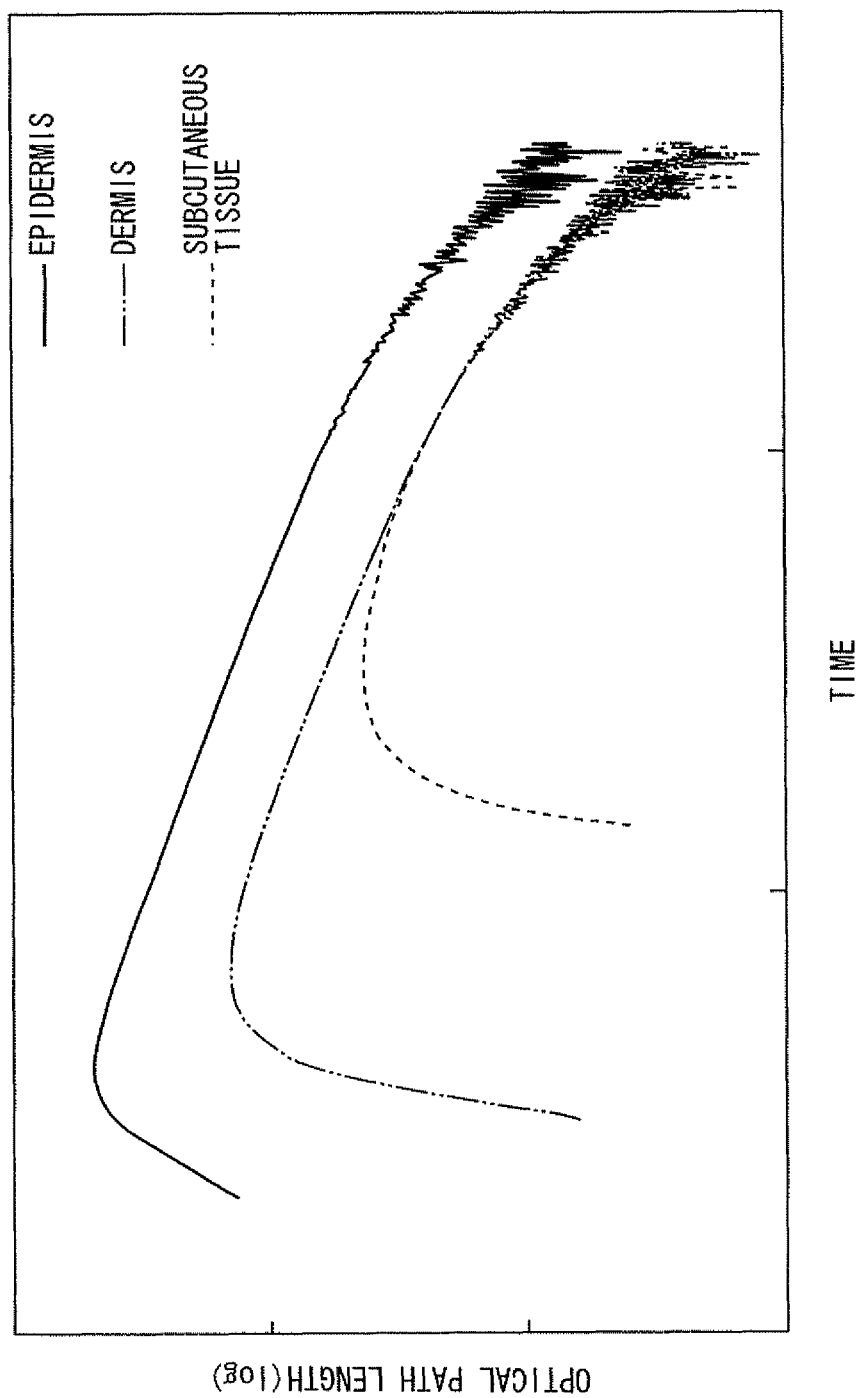
FIG. 3 is a diagram showing an optical propagation path length distribution of each layer calculated by a simulation unit.

FIG. 3 is a diagram showing the optical propagation path length distribution of each layer calculated by the simulation unit.

In FIG. 3, a horizontal axis denotes an elapsed time from photon irradiation and a vertical axis denotes a logarithm of the optical path length.

The simulation unit 2 classifies each movement path of photons reaching the light receiving unit 8 for each layer through which the movement path passes. The simulation unit 2 calculates the optical propagation path length distribution of each layer of the skin as shown in FIG. 3 by calculating an average length of a movement path of photons arriving per unit time, for each classified layer.

Figure 4:
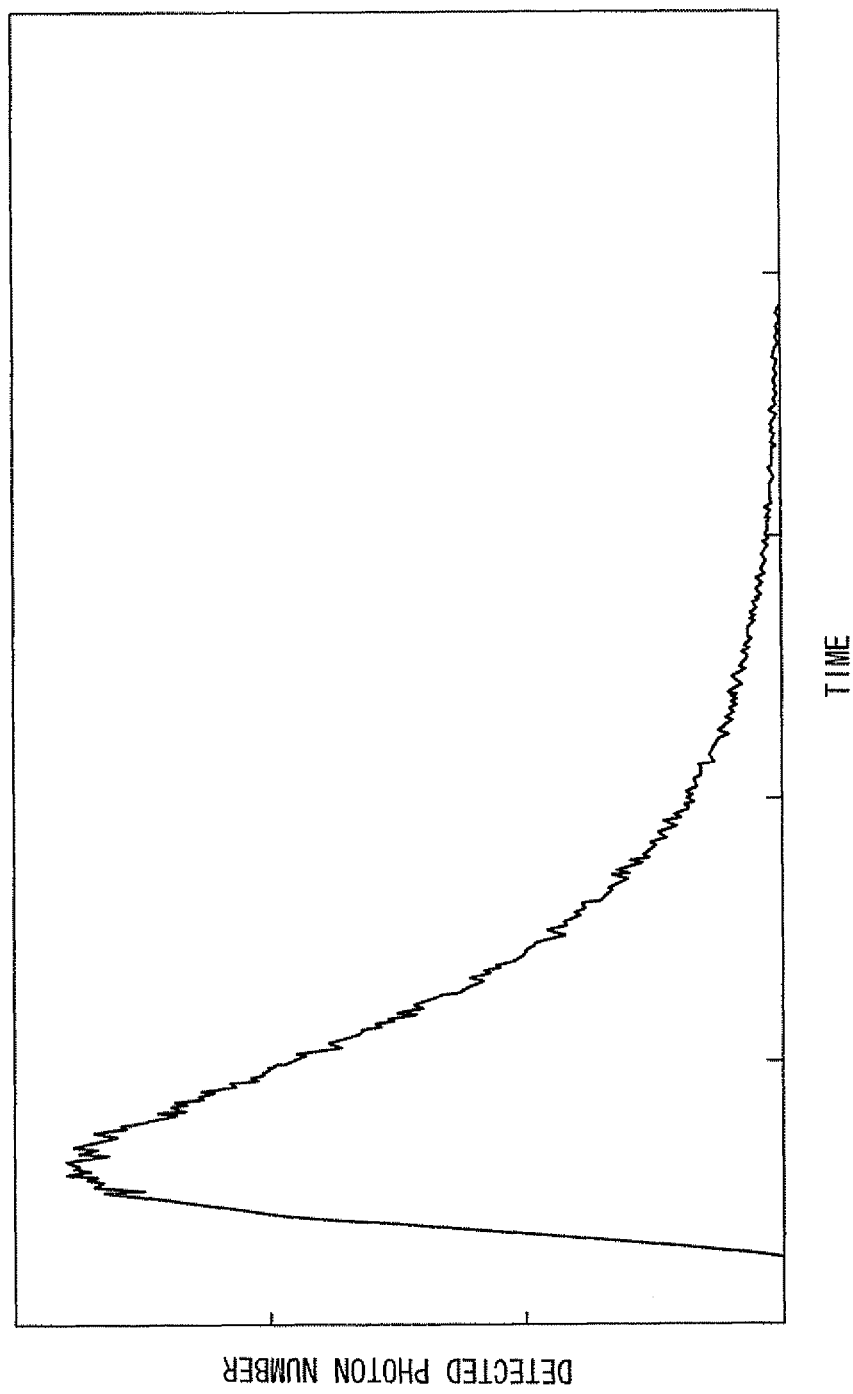
FIG. 4 is a diagram showing a time-resolved waveform calculated by the simulation unit.

FIG. 4 is a diagram showing the time-resolved waveform calculated by the simulation unit.

In FIG. 4, a horizontal axis indicates an elapsed time from photon irradiation and a vertical axis indicates a number of photons detected by the light receiving unit 8.

The simulation unit 2 calculates the time-resolved waveform of the skin model as shown in FIG. 4 by calculating the number of photons reaching the light receiving unit 8 per unit time.

Through the process described above, the simulation unit 2 calculates the optical propagation path length distribution and the time-resolved waveform of the skin model for a plurality of wavelengths. In this case, the simulation unit 2 may calculate the optical propagation path length distribution and the time-resolved waveform for a wavelength at which a difference between absorption spectra of the main components of the skin (e.g., water, protein, lipid, and glucose) is great.

Figure 5:
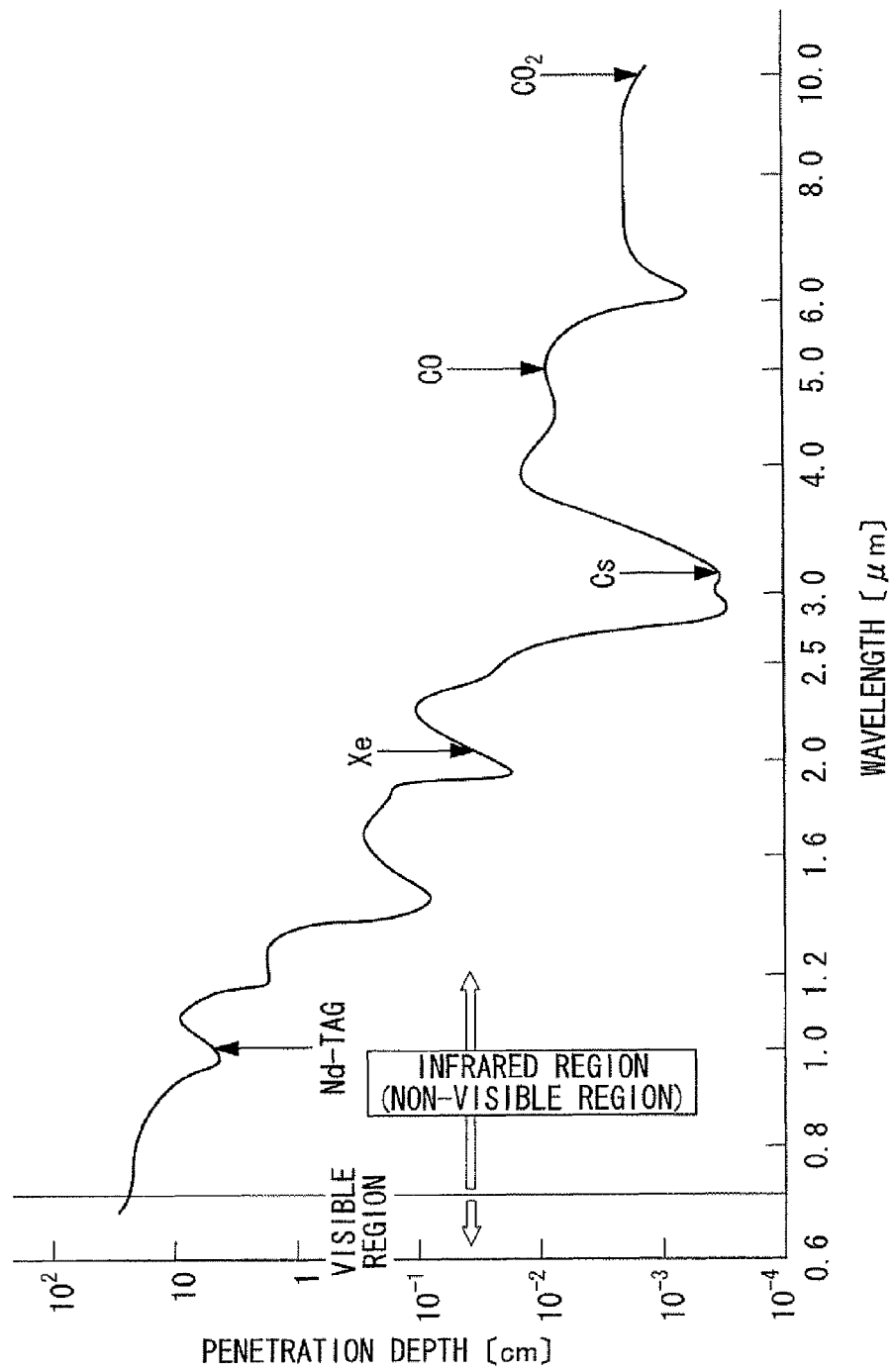
FIG. 5 is a diagram showing a light absorption wavelength characteristic of water.

FIG. 5 is a diagram showing a light absorption wavelength characteristic of water (Kubo Uichi, "Introduction to Medical Laser," 1st Edition, Ohmsha, Ltd., Issued Jun. 25, 1985, page 70, ISBN4-274-03065-2).

In FIG. 5, a horizontal axis indicates a wavelength (μm) of an irradiation light, a vertical axis indicates a penetration depth (cm) of the irradiation light to the skin, and a penetration depth until light intensity is reduced to ⅒ when light is incident to water is shown with respect to light having each wavelength in an infrared region.

For example, it can be seen that in light in a wavelength band near 3.0 μm, the penetration depth is as small as about $2 \times 10^{-3}$ cm and the light is easily absorbed to water.

Figure 6:
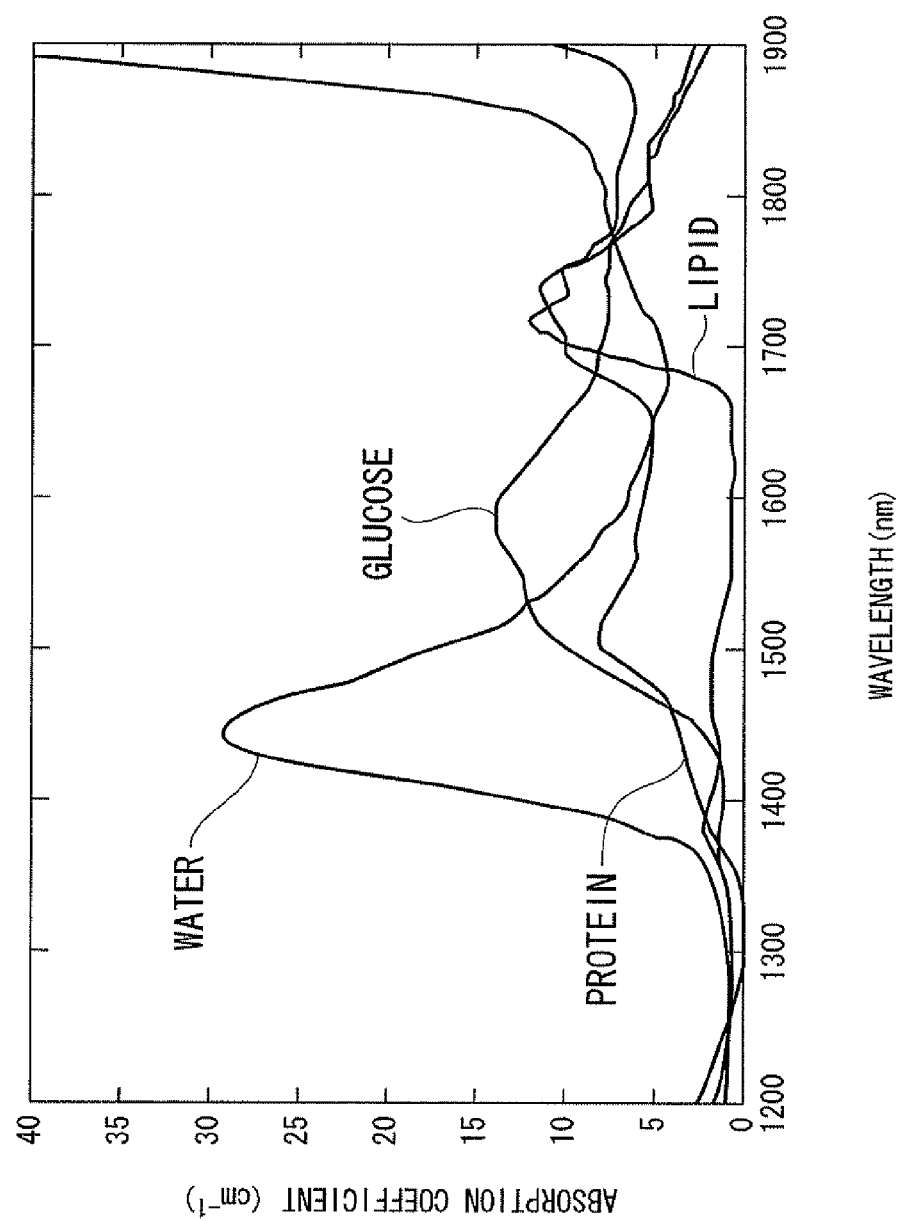
FIG. 6 is a diagram showing an absorption spectrum of main components of the skin.

FIG. 6 is a graph showing an absorption spectrum of main components of the skin. In FIG. 6, a horizontal axis indicates a wavelength of irradiation light and a vertical axis indicates an absorption coefficient.

It can be seen from FIG. 6 that the absorption coefficient of glucose is maximized when the wavelength is 1600 nm and the absorption coefficient of water is maximized when the wavelength is 1450 nm.

Accordingly, the simulation unit 2 may calculate the optical propagation path length distribution and the time-resolved waveform with respect to wavelengths at which a difference between absorption spectra of the main components of the skin is great, such as 1400 nm, 1450 nm, 1500 nm, 1600 nm, 1680 nm, 1720 nm, and 1740 nm.

When the simulation unit 2 calculates the optical propagation path length distribution and the time-resolved waveform of the skin model for a plurality of wavelengths, the simulation unit 2 stores information of the optical propagation path length distribution in the optical path length distribution storage unit 3 and stores information of the time-resolved waveform in the time-resolved waveform storage unit 4.

Figure 7:
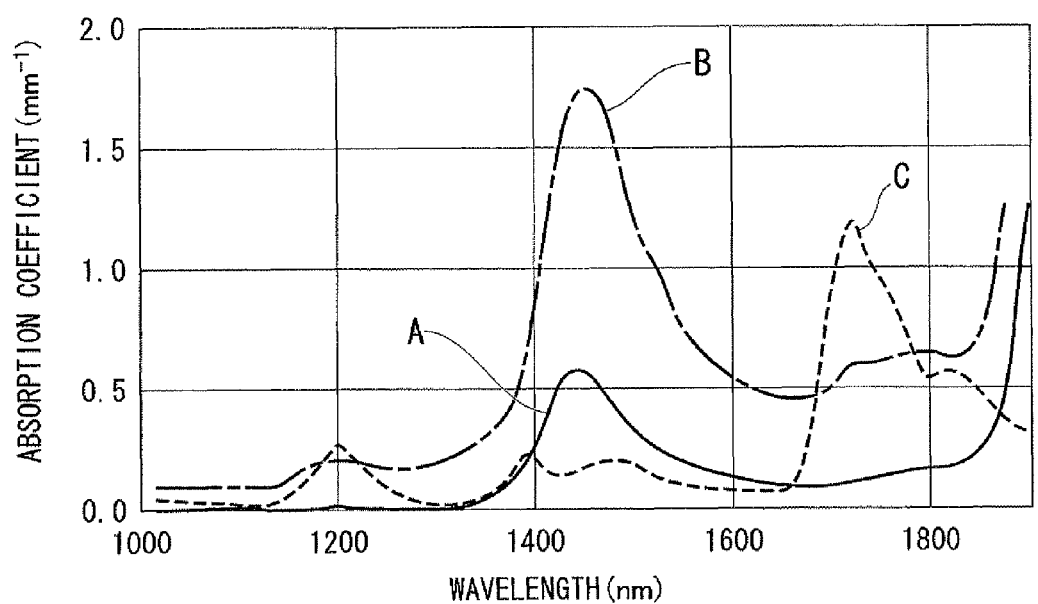
FIG. 7 is a diagram showing a relationship between a wavelength of light irradiated to each of subcutaneous tissue, a dermis and an epidermis of skin and an absorption coefficient.

FIG. 7 is a diagram showing a relationship between a wavelength of light irradiated to each of the epidermis 220, the dermis 230 and the subcutaneous tissue 240 of the skin 210 and an absorption coefficient. In FIG. 7, A denotes the absorption coefficient of the epidermis 220, B denotes the absorption coefficient of the dermis 230, and C denotes the absorption coefficient of the subcutaneous tissue 240.

Referring to FIG. 7, since, in the absorption spectrum of the dermis 230, a maximum value is near a wavelength of 1450 nm and the absorption coefficient value is about 60% of the absorption coefficient of the water, 60% of the absorption of the dermis 230 can be regarded as due to the water. Further, it can be seen that since, even in the absorption spectrum of the epidermis 220, a maximum value having a size that is about ⅓ that of the dermis 230 is near the wavelength of 1450 nm and the absorption coefficient value is about 20% of the absorption coefficient of the water, 20% of the absorption of the epidermis 220 is due to the water. Meanwhile, it can be considered that since, in the absorption spectrum of the subcutaneous tissue 240, only a maximum value having a size that is about ⅒ that of the dermis 230 is near the wavelength of 1450 nm and the absorption coefficient value is a few % of the absorption coefficient of the water, a few % of the absorption of the subcutaneous tissue 240 is due to the water.

Thus, while 60% of the absorption of the dermis 230 is considered to be due to the water and 20% of the absorption of the epidermis 220 is considered to be due to the water, a few % of the absorption in the subcutaneous tissue 240 is considered to be due to the water. Accordingly, it can be seen that, in order to non-invasively measure the blood sugar value from the skin, the dermis 230 containing glucose may be selected as a measurement target and an amount of the glucose contained in the dermis 230 may be measured.

It is known that the absorption coefficient of the water depends on temperature.

Figure 8:
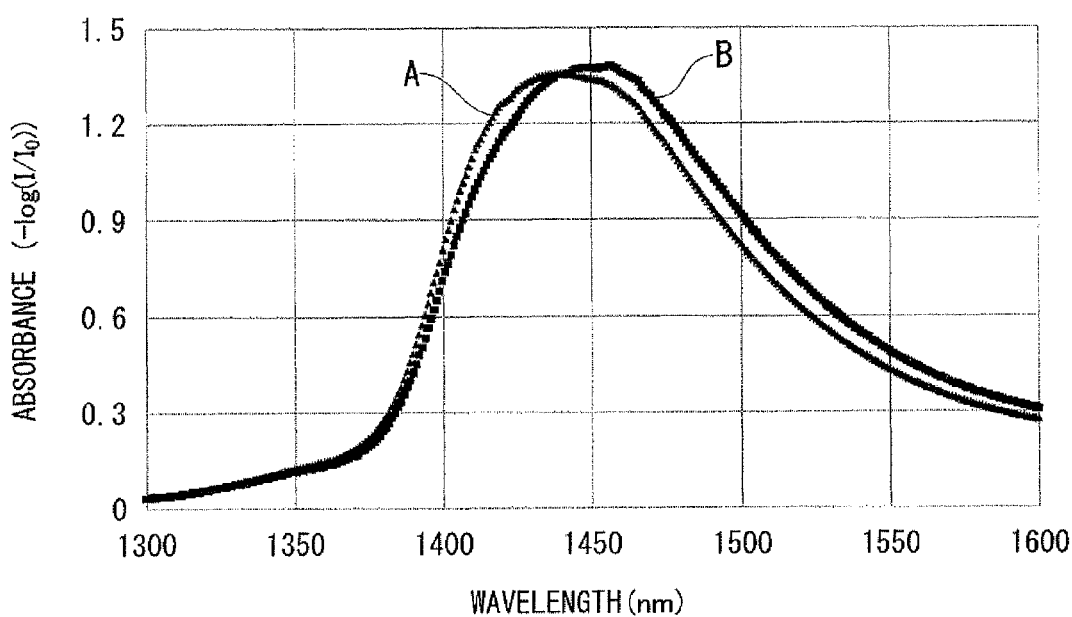
FIG. 8 is a diagram showing temperature dependence of an absorbance spectrum of water.

FIG. 8 is a diagram showing temperature dependence of the absorbance spectrum of the water. In FIG. 8, A denotes an absorbance spectrum of the water at 41° C. and 13 denotes the absorbance spectrum of the water at 21° C.

Here, the absorbance spectrum of the water at each of 41° C. and 21° C. was measured using an ultraviolet, visible and near-infrared spectrophotometer Lambda 900S (available from PerkinElmer Corp.), in which an optical cell having a cell length of 0.5 mm was used, a temperature control unit type was used as an optical cell holder, and temperature was adjusted in a range of ±0.1° C. using a bath circulator.

It is seen from FIG. 8 that a maximum value of the absorbance spectrum of the water is near a wavelength of 1450 nm at 21° C., and the maximum value is shifted from 1450 nm to a shorter wavelength when the temperature is higher than 21° C.

The absorbance spectrum of the water at 21° C. is used as a reference, a difference between an absorbance spectrum of the water at a temperature other than 21° C. and the reference is obtained, and a wavelength of a point at which the difference is "0" is obtained. This wavelength becomes a wavelength not affected by a temperature change.

Figure 9:
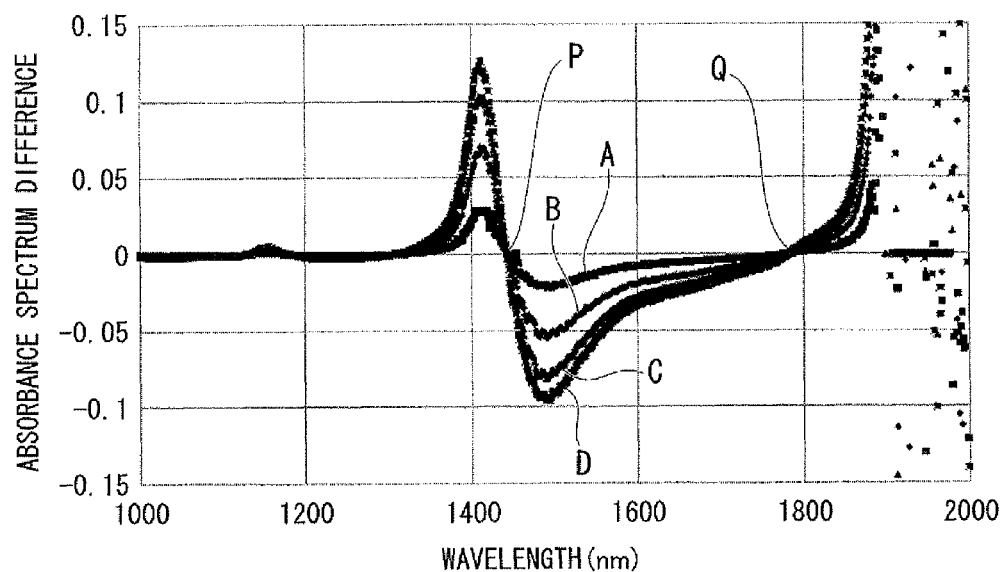
FIG. 9 is a diagram showing temperature dependence of a difference between absorbance spectra of water.

FIG. 9 is a diagram showing a temperature dependence of a difference between absorbance spectra of the water. In FIG. 9, A indicates a difference between the absorbance spectrum of the water at 25° C. and the absorbance spectrum of the water at 21° C., B indicates a difference between the absorbance spectrum of the water at 31° C. and the absorbance spectrum of the water at 21° C., C indicates a difference between the absorbance spectrum of the water at 37° C. and the absorbance spectrum of the water at 21° C., and D indicates a difference between the absorbance spectrum of the water at 41° C. and the absorbance spectrum of the water at 21° C.

It is seen from FIG. 9 that a maximum value of a difference between absorbance spectra of water in each temperature difference is shifted to a shorter wavelength as the temperature difference is great and a minimum value of the difference is shifted to a longer wavelength as the temperature difference is great, but the wavelength is constant irrespective of a size of the temperature difference at points P and Q at which the difference between the absorbance spectra of the water is "0." In this case, the wavelength at the point P is 1445 nm and the wavelength at the point Q is 1782 nm. Accordingly, when the absorbance spectrum of a sample is measured using light having either of 1445 nm and 1782 nm as the specific wavelength $\lambda_k$, the obtained absorbance spectrum is not affected by the temperature change.

For example, ranges of an absorbance and an absorption coefficient that can be regarded as stable against a temperature change when a blood sugar value is 100 mg/dl and a measurement accuracy is ±5% for two types of wavelengths of 1445 nm and 1782 nm were obtained to be 1.35±0.0000175 and ±0.00004/mm at the wavelength of 1445 nm and 0.39±0.0000175 and ±0.00004/mm at the wavelength of 1782 nm by experiment. Accordingly, wavelength ranges were obtained to be 1445±0.025 nm and 1782±0.1 nm from the absorbance and absorption coefficient ranges.

As a result, it was seen that the wavelength ranges that can be regarded as stable against the temperature change when the blood sugar value is 100 mg/dl and measurement accuracy is ±5©% are 1445±0.025 nm and 1782±0.1 nm.

Thus, measurement of an amount of the glucose contained in the dermis 230 using short pulsed light having a specific wavelength $\lambda_k$ at which a temperature change of the absorption coefficient of the water in the dermis is small enables the blood sugar value to be non-invasively measured from the skin.

Figure 10:
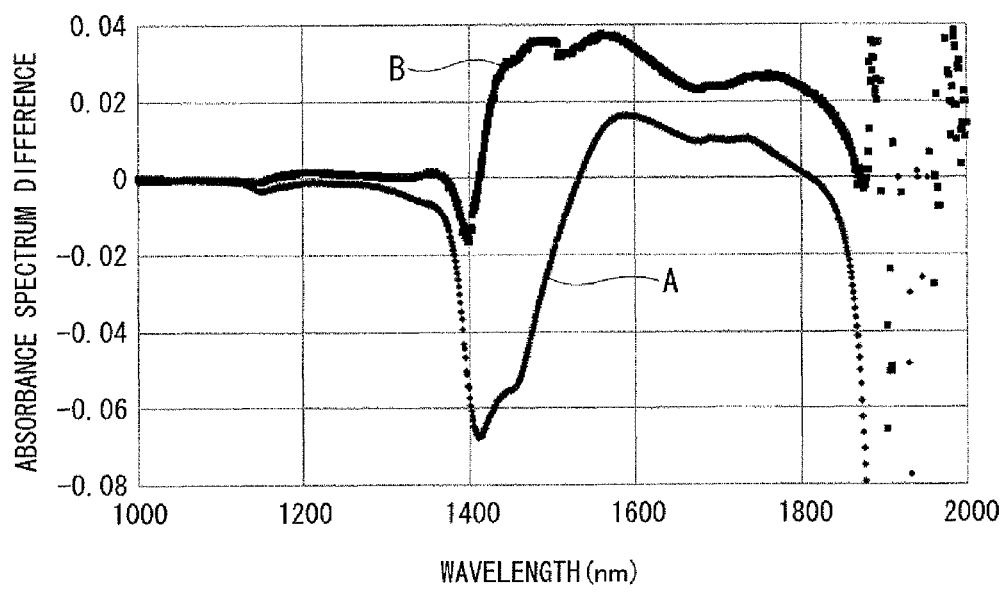
FIG. 10 is a diagram showing an example of an absorbance spectrum of a glucose solution.

FIG. 10 is a diagram showing an example of an absorbance spectrum of a glucose solution. In FIG. 10, A indicates a measured value of an absorbance spectrum of a glucose solution having a high concentration of 9.4 g/dl which was measured using distilled water (21.5° C.) as a reference side, and B indicates a correction value obtained by performing temperature correction and volume correction on a measured value of the absorbance spectrum of the same glucose solution.

In the glucose solution, a glucose concentration is 9.4 g/dl, which is about 100 times a normal value, and thus a volume increase at this time is about 6%.

Further, in this concentration, a volume ratio of the glucose and the water is as great as 6:100, which cannot be ignored. Thus, since the volume of the water of the sample side is reduced compared to the volume of the water of the reference side, the absorbance spectrum difference has a great negative value in wavelength regions near 1400 to 1500 nm and 1900 nm or more in which the absorbance of the water is great. This volume decrease corresponds to a decrease of 0.057 mm for a cell length of 1 mm. When the volume decrease and temperature correction are performed on the measured value of the absorbance spectrum of the glucose solution, a correction value indicated by B in FIG. 10 is obtained and is similar to an absorbance spectrum of solid glucose.

Thus, the value similar to the absorbance spectrum of the glucose alone can be obtained by performing the temperature correction and the volume correction on the measured value of the absorbance spectrum of the glucose solution.

Next, a process of measuring a blood sugar value using the blood sugar value measurement apparatus 1 will be described based on FIG. 11.

First, a user operates the blood sugar value measurement apparatus 1 by putting the blood sugar value measurement apparatus 1 to skin of, for example, his or her wrist and pressing a measurement initiation switch (not shown).

Here, the irradiation unit 5 irradiates, to the skin 21, short pulsed light having a specific wavelength $\lambda_k$ at which a temperature change of the absorption coefficient of the water in the dermis 230 constituting the skin 21 is small (step S1).

For example, one or both of 1445 nm and 1782 nm obtained in FIG. 9 may be used as the specific wavelength $\lambda_k$.

Then, the light guide unit 6 focuses plural types of backscattered light radiated from the skin 21, i.e., backscattered light radiated from the subcutaneous tissue 240, the dermis 230 and the epidermis 220, and guides the backscattered light to the light scattering medium layer selection unit 7.

The light scattering medium layer selection unit 7 selects signal light containing more backscattered light radiated by the dermis 230 from among the backscattered light radiated from the subcutaneous tissue 240, the dermis 230 and the epidermis 220 focused and guided by the light guide unit 6 (step S2).

Then, the light receiving unit 8 receives the backscattered light per unit time radiated from the dermis 230 (step S3). In this case, the light receiving unit 8 records light reception intensity per unit time (e.g., times $t_1$ to $t_m$ per 1 picosecond) from irradiation initiation in an internal memory.

When the light intensity acquisition unit 9 is notified that the light receiving unit 8 has completed light reception, the light intensity acquisition unit 9 acquires light reception intensity, at different times, of the backscattered light radiated from the dermis 230 (step S4). That is, the light intensity acquisition unit 9 acquires the light intensity of the backscattered light at each of a plurality of times $t_1$ to $t_m$.

Here, the times $t_1$ to $t_m$ when the light intensity acquisition unit 9 acquires the light intensity preferably include a time when the backscattered light radiated from the dermis 230 reaches a peak. That is, the time preferably is a time obtained by adding a time when the optical path length of the dermis 230 is maximized, to a time when the irradiation unit 5 has irradiated the short pulsed light having the specific wavelength $\lambda_1$.

Then, the optical absorption coefficient calculation unit 12 calculates the optical absorption coefficient of the dermis 230 based on the light reception intensity, at different times, of the backscattered light radiated from the dermis 230 acquired by the light intensity acquisition unit 9, i.e., the light intensity of the backscattered light at each of a plurality of times $t_1$ to $t_m$, using the following equation (8):

$$\begin{cases} N(t_1)\ln\left(\frac{N(t_1)}{I(t_1)}\right) = \sum_{i=1}^{n}\mu_i L_i(t_1) \\ \vdots \\ N(t_m)\ln\left(\frac{N(t_m)}{I(t_m)}\right) = \sum_{i=1}^{n}\mu_i L_i(t_m) \end{cases} \quad (8)$$

(where, I(t) denotes the intensity of the light received by the light receiving unit 5 at time t, N(t) denotes the light intensity, at time t, of the model of the time-resolved waveform of the short pulsed light having the specific wavelength $\lambda_k$, Li(t) denotes an optical path length of an i-th layer, at time t, of the model of the optical propagation path length distribution in each layer of the skin, and $\mu_i$ denotes an optical absorption coefficient of the i-th layer) (step S5).

Here, the first layer is the epidermis, the second layer is the dermis, the third layer is the subcutaneous tissue, $\mu_1$ denotes an optical absorption coefficient of the epidermis, $\mu_2$ denotes an optical absorption coefficient of the dermis, and $\mu_3$ denotes an optical absorption coefficient of the subcutaneous tissue.

Then, a determination is made as to whether the optical absorption coefficients have been calculated for as many specific wavelengths $\lambda_k$ as the number of types of the specific wavelength $\lambda_k$. When the optical absorption coefficients have been calculated, a next process is performed. When the optical absorption coefficients have not been calculated, a process subsequent to step S1 of irradiating the short pulsed light having the specific wavelength $\lambda_k$ is performed again (step S6).

Here, when the optical absorption coefficients have been calculated for as many specific wavelengths $\lambda_k$ as the number of types of the specific wavelength $\lambda_k$, the concentration calculation unit 13 calculates a concentration of the glucose contained in the dermis 230 based on the optical absorption coefficient $\mu$ of the dermis 230 calculated by the optical absorption coefficient calculation unit 12.

Here, a case in which the glucose concentration is calculated, for example, from a relationship between an optical absorption coefficient of a main component at a single wavelength and an optical absorption coefficient of each layer will be described.

The following equation (9) shows that the optical absorption coefficient of the skin is a sum of a function for a wavelength of each of water, glucose, protein, lipid and other components and a coefficient thereof:

$$f_{abs}(\lambda) = af_{Water}(\lambda) + bf_{Glc}(\lambda) + cf_P(\lambda) + df_L(\lambda) + \quad (9)$$

Equation (10) shows that an optical absorption coefficient of each of the epidermis, the dermis, and the subcutaneous tissue of the skin is a sum of an optical absorption coefficient for a wavelength for each of water, glucose, protein, lipid and other components and a concentration, from the optical absorption coefficient of the skin shown in Equation (9):

$$\begin{cases} \mu_{L1}(\lambda) = \varepsilon_W(\lambda)C_{WL1} + \varepsilon_W(\lambda)C_{WL1} + \varepsilon_P(\lambda)C_{PL1} + \varepsilon_L(\lambda)C_{LL1} \ldots \\ \mu_{L2}(\lambda) = \varepsilon_W(\lambda)C_{WL2} + \varepsilon_W(\lambda)C_{WL2} + \varepsilon_P(\lambda)C_{PL2} + \varepsilon_L(\lambda)C_{LL2} \ldots \\ \mu_{L3}(\lambda) = \varepsilon_W(\lambda)C_{WL3} + \varepsilon_W(\lambda)C_{WL3} + \varepsilon_P(\lambda)C_{PL3} + \varepsilon_L(\lambda)C_{LL3} \ldots \\ \vdots \end{cases} \quad (10)$$

Equation (11) is a version of Equation (10) using a matrix. In Equation (11), "C" is a coefficient matrix showing a concentration of each of water, glucose, protein, lipid and other components in each of the epidermis, dermis and subcutaneous tissues of the skin:

$$\begin{pmatrix} \mu_{L1} \\ \mu_{L2} \\ \mu_{L3} \\ \vdots \end{pmatrix} = \begin{pmatrix} \varepsilon_W(\lambda) \ldots \\ \varepsilon_G(\lambda) \ldots \\ \varepsilon_P(\lambda) \ldots \\ \varepsilon_L(\lambda) \ldots \\ \vdots \end{pmatrix} C \quad (11)$$

Equation (11) may be modified to Equation (12), which is a simple simultaneous equation to solve "C":

$$C = \begin{pmatrix} \varepsilon_W(\lambda) \ldots \\ \varepsilon_G(\lambda) \ldots \\ \varepsilon_P(\lambda) \ldots \\ \varepsilon_L(\lambda) \ldots \\ \vdots \end{pmatrix}^{-1} \begin{pmatrix} \mu_{L1} \\ \mu_{L2} \\ \mu_{L3} \\ \vdots \end{pmatrix} \quad (12)$$

When Equation (12) is expressed using a matrix, Equation (13) is obtained.

Here, a simple simultaneous equation representing a relationship between an absorption coefficient of a main component of the skin at a plurality of wavelengths ($\lambda$) and a concentration thereof in Equation (14) is formed for the optical absorption coefficient of the dermis (L2):

$$\begin{pmatrix} \mu_a(\lambda_1)_{L2} \\ \mu_a(\lambda_2)_{L2} \\ \mu_a(\lambda_3)_{L2} \\ \mu_a(\lambda_4)_{L2} \\ \vdots \end{pmatrix} = \quad (14)$$

$$(C_{WL2} C_{GL2} C_{PL2} C_{LL2} \ldots) \begin{pmatrix} \varepsilon_W(\lambda_1) & \varepsilon_W(\lambda_2) & \varepsilon_W(\lambda_3) & \varepsilon_W(\lambda_4) \\ \varepsilon_G(\lambda_1) & \varepsilon_G(\lambda_2) & \varepsilon_G(\lambda_3) & \varepsilon_G(\lambda_4) \\ \varepsilon_P(\lambda_1) & \varepsilon_P(\lambda_2) & \varepsilon_P(\lambda_3) & \varepsilon_P(\lambda_4) \\ \varepsilon_L(\lambda_1) & \varepsilon_L(\lambda_2) & \varepsilon_L(\lambda_3) & \varepsilon_L(\lambda_4) \end{pmatrix}$$

Equation (14) may be modified to Equation (15):

$$\begin{pmatrix} \mu_a(\lambda_1)_{L2} \\ \mu_a(\lambda_2)_{L2} \\ \mu_a(\lambda_3)_{L2} \\ \mu_a(\lambda_4)_{L2} \\ \vdots \end{pmatrix} = \begin{pmatrix} \varepsilon_W(\lambda_1) & \varepsilon_G(\lambda_1) & \varepsilon_P(\lambda_1) & \varepsilon_L(\lambda_1) \\ \varepsilon_W(\lambda_2) & \varepsilon_G(\lambda_2) & \varepsilon_P(\lambda_2) & \varepsilon_L(\lambda_2) \\ \varepsilon_W(\lambda_3) & \varepsilon_G(\lambda_3) & \varepsilon_P(\lambda_3) & \varepsilon_L(\lambda_3) \\ \varepsilon_W(\lambda_4) & \varepsilon_G(\lambda_4) & \varepsilon_P(\lambda_4) & \varepsilon_L(\lambda_4) \\ \vdots & \vdots & \vdots & \vdots \end{pmatrix} \begin{pmatrix} C_{WL2} \\ C_{GL2} \\ C_{PL2} \\ C_{LL2} \end{pmatrix} \quad (15)$$

Equation (15) may be modified to Equation (16), which is a simple simultaneous equation to solve "C." In Equation (16), $\varepsilon_W$ denotes the optical absorption coefficient of the water, $\varepsilon_G$ denotes the optical absorption coefficient of the glucose, $\varepsilon_P$ denotes the optical absorption coefficient of the protein, $\varepsilon_L$ denotes the optical absorption coefficient of the lipid, $\mu_{L1}$ denotes the optical absorption coefficient of the epidermis, $\mu_{L2}$ denotes the optical absorption coefficient of the dermis, and $\mu_{L3}$ denotes the optical absorption coefficient of the subcutaneous tissue. Further, optical absorption coefficients of main components of the skin and layers of the skin may be added:

$$\begin{pmatrix} C_{WL2} \\ C_{GL2} \\ C_{PL2} \\ C_{LL2} \end{pmatrix} = \begin{pmatrix} \varepsilon_W(\lambda_1) & \varepsilon_G(\lambda_1) & \varepsilon_P(\lambda_1) & \varepsilon_L(\lambda_1) \\ \varepsilon_W(\lambda_2) & \varepsilon_G(\lambda_2) & \varepsilon_P(\lambda_2) & \varepsilon_L(\lambda_2) \\ \varepsilon_W(\lambda_3) & \varepsilon_G(\lambda_3) & \varepsilon_P(\lambda_3) & \varepsilon_L(\lambda_3) \\ \varepsilon_W(\lambda_4) & \varepsilon_G(\lambda_4) & \varepsilon_P(\lambda_4) & \varepsilon_L(\lambda_4) \\ \vdots & \vdots & \vdots & \vdots \end{pmatrix}^{-1} \begin{pmatrix} \mu_a(\lambda_1)_{L2} \\ \mu_a(\lambda_2)_{L2} \\ \mu_a(\lambda_3)_{L2} \\ \mu_a(\lambda_4)_{L2} \\ \vdots \end{pmatrix} \quad (16)$$

Thus, the coefficient matrix "C" for the dermis (L2) may be calculated using Equation (16).

Further, a difference at a plurality of wavelengths will be described herein.

Here, the concentration of the glucose contained in the dermis 230 is calculated using the following equation (17):

$$\begin{cases} \mu_{a(1)} - \mu_{a(2)} = \sum_{j=1}^{p} g_j (\varepsilon_{j(1)} - \varepsilon_{j(2)}) \\ \quad \vdots \\ \mu_{a(q-1)} - \mu_{a(q)} = \sum_{j=1}^{p} g_j (\varepsilon_{j(q-1)} - \varepsilon_{j(q)}) \end{cases} \quad (17)$$

(where, $\mu_a$ denotes an optical absorption coefficient in an a-th layer that is the layer of the skin, $g_j$ denotes a molar concentration of a j-th component constituting the skin, $\varepsilon_j$ denotes an optical absorption coefficient of the j-th component, p denotes the number of main components constituting the skin, and q denotes the number of types of the short pulsed light) (step S7).

The above-described blood sugar value measurement apparatus 1 includes a computer system therein, and the processing operation of each step described above is stored in a program format in a computer-readable recording medium. When the program is read and executed by the computer, the processing operation may be performed.

Here, the computer-readable recording medium may include a magnetic disk, a magneto-optical disc, a CD-ROM, a DVD-ROM, a semiconductor memory, etc.

Further, the computer program is distributed to a computer by a communication line so that the program is executed by the computer.

Further, the above program may realize a part of each step.

Further, the program may be a difference file (a difference program) that can realize the above-described function in combination with a program that has already been recorded in a computer system.

As described above, according to the present embodiment, the use of the short pulsed light having the specific wavelength at which the temperature change of the absorption coefficient of the water is small as the short pulsed light irradiated to the skin can reduce effects of the water in the backscattered light radiated from the dermis and also effects of the water in the glucose concentration in the dermis of the skin calculated based on the backscattered light. Accordingly, it is possible to reduce the effects of the water in the glucose concentration and to accurately measure the concentration of the glucose contained in the dermis in a non-invasive manner.

(Second Embodiment)

Figure 12:
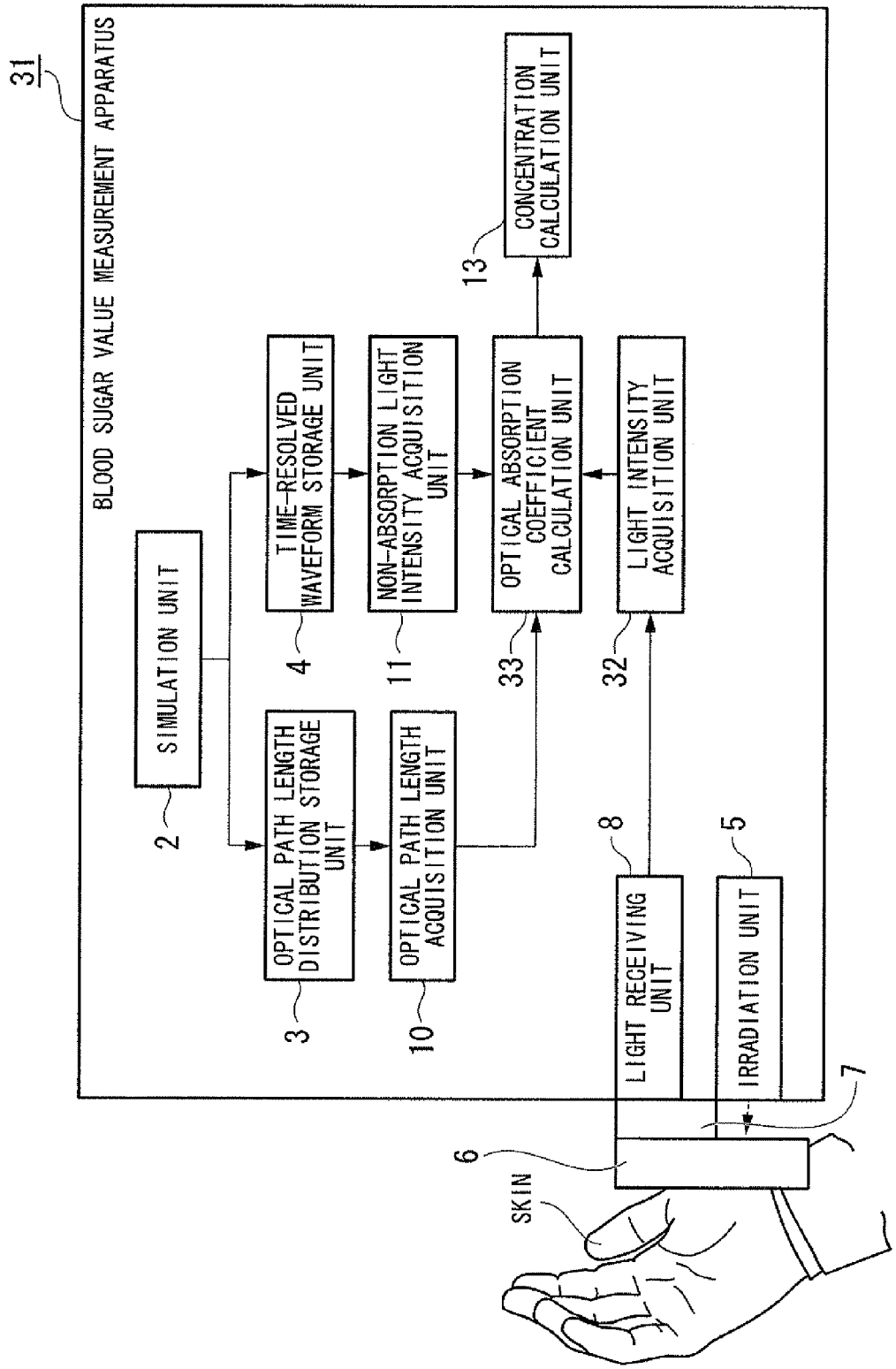
FIG. 12 is a schematic block diagram showing a configuration of a blood sugar value measurement apparatus of a second embodiment of the present invention.

FIG. 12 is a schematic block diagram showing a configuration of a blood sugar value measurement apparatus of a second embodiment of the present invention. A difference between a blood sugar value measurement apparatus 31 of the present embodiment and the blood sugar value measurement apparatus 1 of the first embodiment is that the light intensity acquisition unit 9 and the optical absorption coefficient calculation unit 12 are substituted with a light intensity acquisition unit 32 and an optical absorption coefficient calculation unit 33 having different functions from those of the light intensity acquisition unit 9 and the optical absorption coefficient calculation unit 12.

The light intensity acquisition unit 32 acquires a time change of a light intensity, between a given time and at least a given time τ, of backscattered light radiated from a dermis, which has been received by a light receiving unit 8.

The optical absorption coefficient calculation unit 33 calculates an optical absorption coefficient in the dermis of the skin to which the short pulsed light having the specific wavelength $\lambda_k$ has been irradiated.

The optical absorption coefficient calculation unit 33 calculates an optical absorption coefficient of any layer in the skin using the following equation (18):

$$\begin{cases} \int_0^\tau \ln\left(\frac{N(t)}{I(t)}\right) L_1(t) dt = \sum_{i=1}^{n} \mu_i \int_0^\tau L_1(t) L_i(t) dt \\ \quad \vdots \\ \int_0^\tau \ln\left(\frac{N(t)}{I(t)}\right) L_n(t) dt = \sum_{i=1}^{n} \mu_i \int_0^\tau L_n(t) L_i(t) dt \end{cases} \quad (18)$$

(where, I(t) denotes the intensity of the light received by the light receiving unit 8 at time t, N(t) denotes the light intensity, at time t, of a model of a time-resolved waveform of the short pulsed light having the specific wavelength $\lambda_k$, Li(t) denotes an optical path length of an i-th layer, at time t, of a model of an optical propagation path length distribution in each layer of the skin, n denotes the number of layers that are observed objects of the skin, and $\mu_i$ denotes an optical absorption coefficient of the i-th layer).

Here, a first layer indicates an epidermis, a second layer indicates a dermis, a third layer is a subcutaneous tissue, $\mu_1$ denotes an optical absorption coefficient of the epidermis, $\mu_2$ denotes an optical absorption coefficient of the dermis, and $\mu_3$ denotes an optical absorption coefficient of the subcutaneous tissue.

Figure 13:
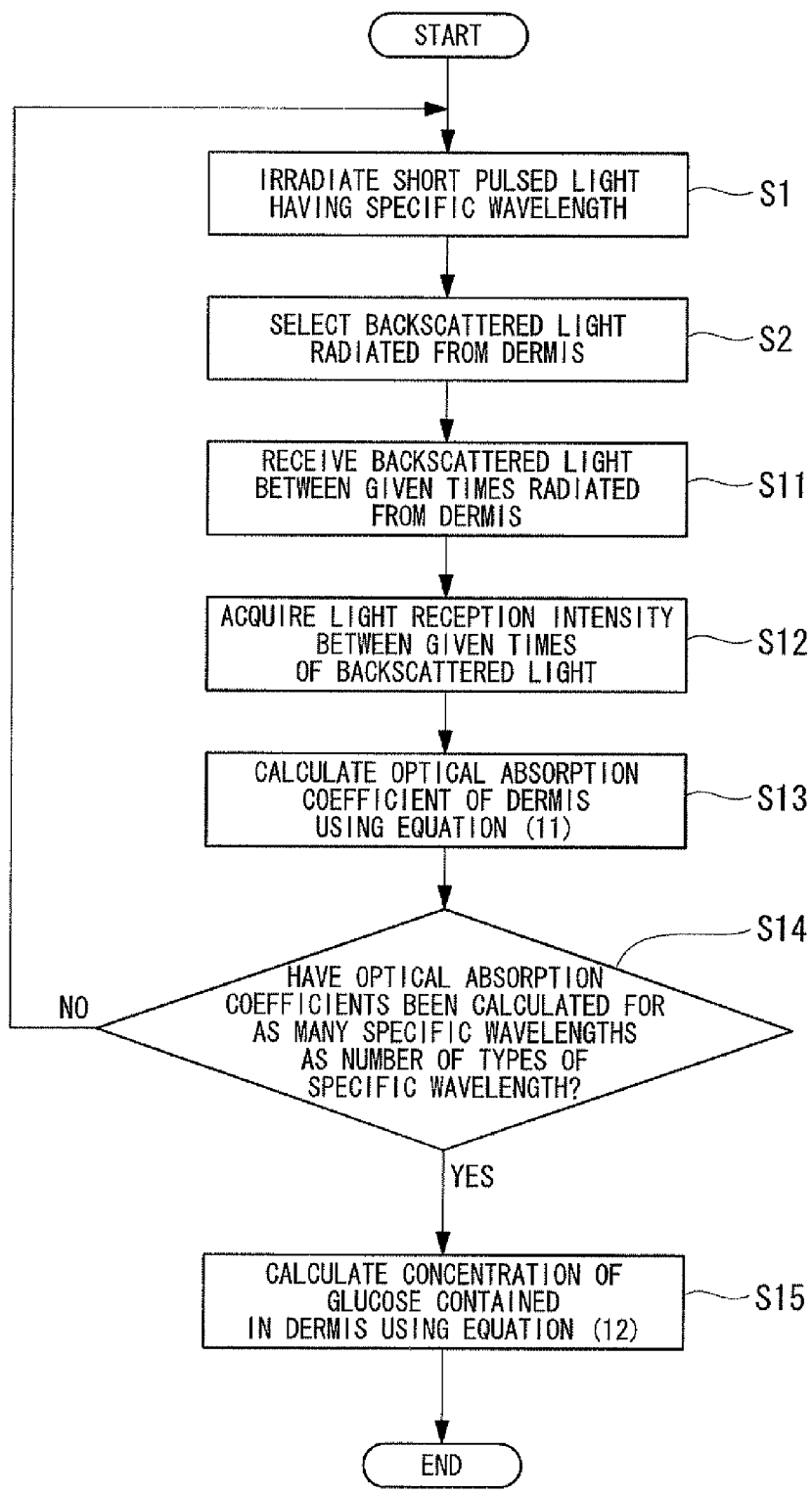
FIG. 13 is a flowchart showing a process of measuring a blood sugar value of the second embodiment of the present invention.

Next, a process of measuring a blood sugar value using the blood sugar value measurement apparatus 31 will be described based on FIG. 13.

Figure 11:
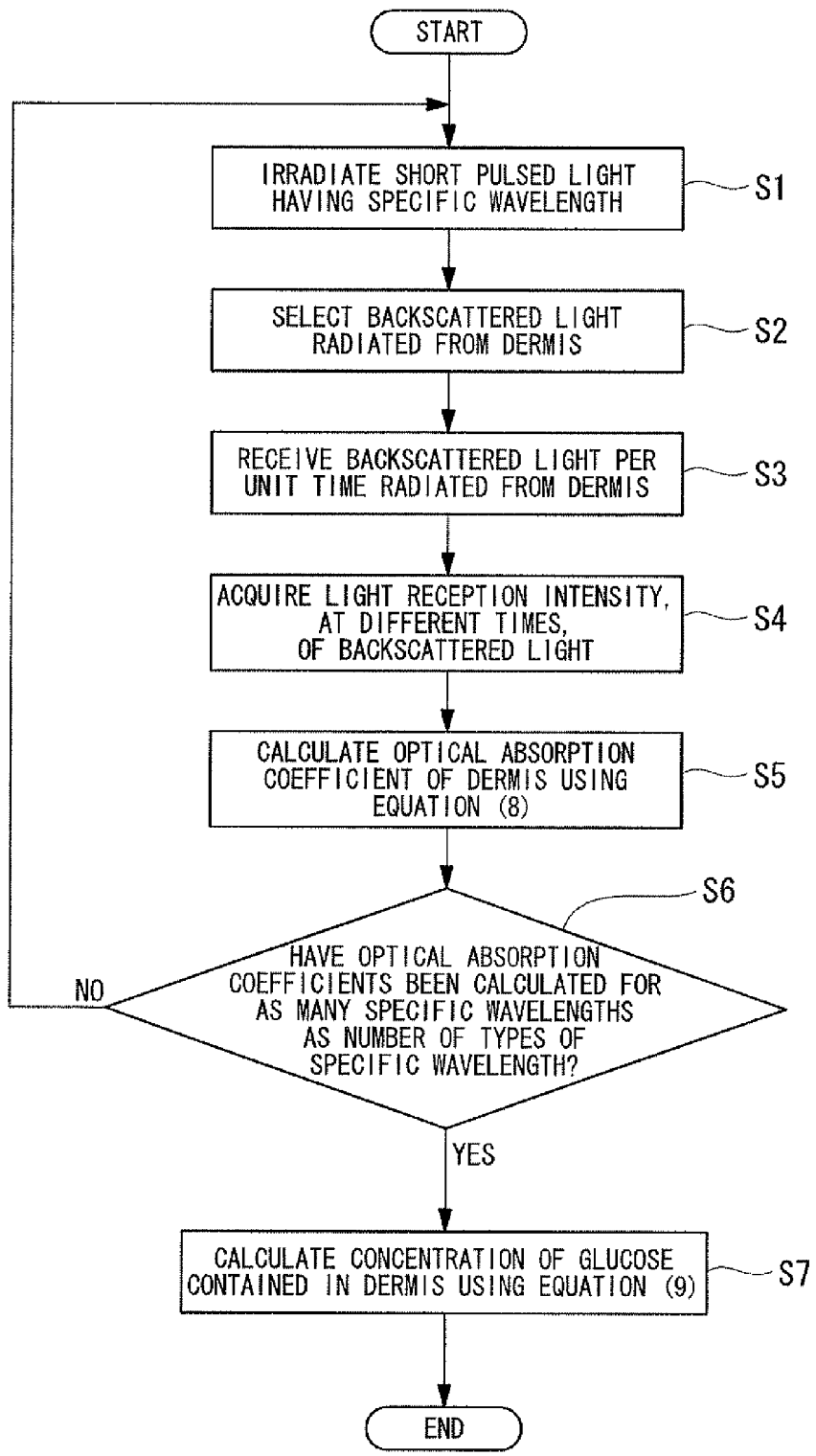
FIG. 11 is a flowchart showing a process of measuring a blood sugar value of a first embodiment of the present invention.

In this process, since processes from an initial process to a process (step S2) in which a light scattering medium layer selection unit 7 selects backscattered light radiated by the dermis 230 from among backscattered light radiated from the subcutaneous tissue 240, the dermis 230 and the epidermis 220 are the same as those shown in FIG. 11, a description thereof will be omitted.

After the backscattered light is selected, the light receiving unit 8 receives the backscattered light that is radiated from the dermis 230 between the given time and the given time $\tau$ (step S11). In this case, the light receiving unit 8 records a time change of light reception intensity between irradiation initiation and at least the given time $\tau$ in an internal memory.

Next, when the light intensity acquisition unit 32 is notified that the light receiving unit 8 has completed light reception, the light intensity acquisition unit 32 acquires the time change of the light reception intensity between the irradiation initiation and at least the given time $\tau$, of the backscattered light radiated from the dermis 230 (step S12).

The optical absorption coefficient calculation unit 33 then calculates the optical absorption coefficient of the dermis 230 based on the time change of the light reception intensity between the irradiation initiation and at least the given time $\tau$ of the backscattered light radiated from the dermis 230, which has been acquired by the light intensity acquisition unit 32, using the following equation (19):

$$\begin{cases} \int_0^\tau \ln\left(\frac{N(t)}{I(t)}\right) L_1(t)\,dt = \sum_{i=1}^n \mu_i \int_0^\tau L_1(t) L_i(t)\,dt \\ \vdots \\ \int_0^\tau \ln\left(\frac{N(t)}{I(t)}\right) L_n(t)\,dt = \sum_{i=1}^n \mu_i \int_0^\tau L_n(t) L_i(t)\,dt \end{cases} \quad (19)$$

(where, I(t) denotes the intensity of the light received by the light receiving unit 8 at time t, N(t) denotes the light intensity, at time t, of the model of the time-resolved waveform of the short pulsed light having the specific wavelength $\lambda_k$, Li(t) denotes an optical path length of an i-th layer, at time t, of the model of the optical propagation path length distribution in each layer of the skin, n denotes the number of layers that are observed objects of the skin, and $\mu_i$ denotes the optical absorption coefficient of the i-th layer) (step S13).

Then, a determination is made as to whether optical absorption coefficients have been calculated for as many specific wavelengths $\lambda_k$ as types of the specific wavelength $\lambda_k$. When the optical absorption coefficients have been calculated, a next process is performed. When the optical absorption coefficients have not been calculated, the steps from step S1 of irradiating the short pulsed light having the specific wavelength $\lambda_k$ are performed again (step S14).

Here, when the optical absorption coefficients have been calculated for as many specific wavelengths $\lambda_k$ as the number of types of the specific wavelength $\lambda_k$, a concentration calculation unit 13 calculates a concentration of glucose contained in the dermis 230 based on the optical absorption coefficient $\mu$ of the dermis 230 calculated by the optical absorption coefficient calculation unit 33 using the following equation (20):

$$\begin{cases} \mu_{a(1)} - \mu_{a(2)} = \sum_{j=1}^p g_j(\varepsilon_{j(1)} - \varepsilon_{j(2)}) \\ \vdots \\ \mu_{a(q-1)} - \mu_{a(q)} = \sum_{j=1}^p g_j(\varepsilon_{j(q-1)} - \varepsilon_{j(q)}) \end{cases} \quad (20)$$

(where, $\mu_a$ denotes the optical absorption coefficient in an a-th layer that is any layer of the skin, $g_j$ denotes a molar concentration of a j-th component constituting the skin, $\varepsilon_j$ denotes an optical absorption coefficient of the j-th component, p denotes the number of main components constituting the skin, and q denotes the number of types of the specific wavelength $\lambda_k$) (step S15).

Even in the present embodiment, it is possible to reduce effects of the water in the backscattered light radiated from the dermis and also to reduce effects of the water in the glucose concentration in the dermis of the skin calculated based on the backscattered light, similar to the first embodiment. Thus, it is possible to reduce the effects of water in the glucose concentration and to accurately measure the concentration of the glucose contained in the dermis in a non-invasive manner.

Further, in each embodiment, the case in which the concentration of the glucose contained in the dermis of the skin is measured by taking the blood sugar value measurement apparatus as a concentration determination apparatus, the skin of a person's palm as an observed object, the glucose as a target component, and the short pulsed light having a specific wavelength as the light having a specific wavelength has been described, but the present invention is not limited thereto. The concentration determination method may be used for another apparatus for determining a concentration of a target component in any layer of an observed object formed of a plurality of light scattering medium layers, or the short pulsed light having the specific wavelength may be substituted with continuous light having a specific wavelength.

For example, when the concentration determination method is applied to a portable apparatus for measuring concentrations of main components of skin, it can be effectively used for inspection, diagnosis or treatment of skin disease.

(Third Embodiment)

Figure 14:
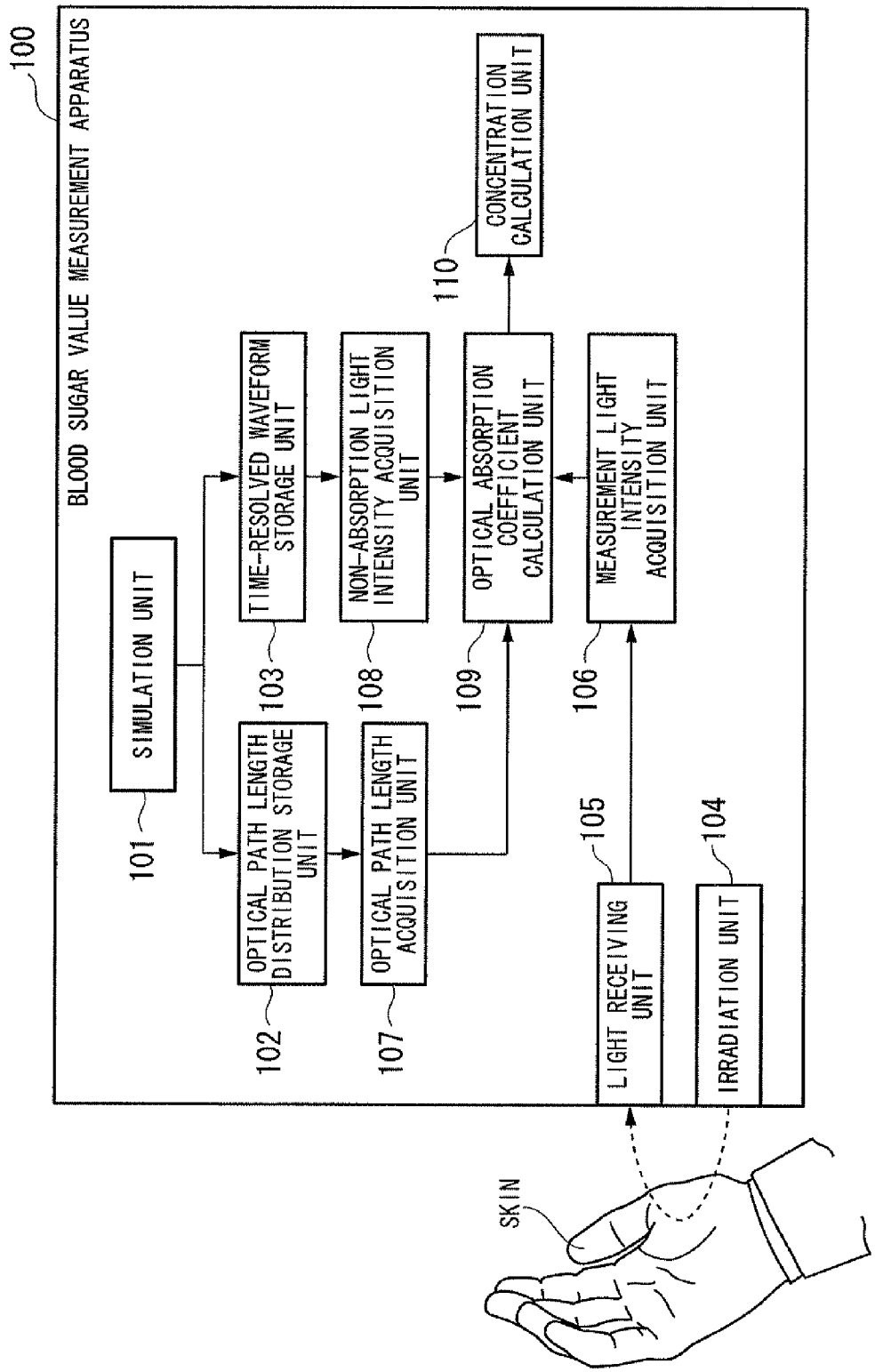
FIG. 14 is a schematic block diagram showing a configuration of a blood sugar value measurement apparatus according to the present invention.

Hereinafter, a third embodiment of the present invention will be described in detail with reference to the accompanying drawings. FIG. 14 is a schematic block diagram showing a configuration of a blood sugar value measurement apparatus according to a third embodiment of the present invention.

A blood sugar value measurement apparatus 100 (a concentration determination apparatus) includes a simulation unit 101, an optical path length distribution storage unit 102, a time-resolved waveform storage unit 103, an irradiation unit 104, a light receiving unit 105, a measurement light intensity acquisition unit 106 (light intensity acquisition unit), an optical path length acquisition unit 107, a non-absorption light intensity acquisition unit 108 (light intensity model acquisition unit), an optical absorption coefficient calculation unit 109, and a concentration calculation unit 110.

The blood sugar value measurement apparatus 100 measures a concentration of glucose (a target component) contained in a dermis (any layer) of skin (an observed object).

The simulation unit 101 performs simulation for irradiating light to a skin model having an optical absorption coefficient of 0.

The optical path length distribution storage unit 102 stores an optical propagation path length distribution of the skin model having the optical absorption coefficient of 0.

The time-resolved waveform storage unit 103 stores a time-resolved waveform of the skin model having the optical absorption coefficient of 0.

The irradiation unit 104 irradiates short pulsed light to the skin.

The light receiving unit 105 receives light obtained as the short pulsed light is backscattered by the skin.

The measurement light intensity acquisition unit 106 acquires a light intensity, at any time, of the light received by the light receiving unit 105.

The optical path length acquisition unit 107 acquires an optical path length at any time from the optical path length distribution storage unit 102.

The non-absorption light intensity acquisition unit 108 acquires a light intensity at any time from the time-resolved waveform storage unit 103.

The optical absorption coefficient calculation unit 109 calculates the optical absorption coefficient in the dermis of the skin to which the short pulsed light has been irradiated.

The concentration calculation unit 110 calculates a concentration of the glucose contained in the dermis.

Here, the short pulsed light refers to pulsed light having a pulse width of about 10 psec or less. Pulsed light having a pulse width in a range of 0.1 psec to 10 psec may be used as the short pulsed light.

In the blood sugar value measurement apparatus 100, the irradiation unit 104 irradiates the short pulsed light to the skin, the light receiving unit 105 receives light obtained as the short pulsed light is backscattered by the skin, and the measurement light intensity acquisition unit 106 acquires the intensity of the light received by the light receiving unit 105 at time t. Next, the optical path length acquisition unit 107 acquires the optical path length of each layer of the skin, at time t, of the optical propagation path length distribution in the skin model from the optical path length distribution storage unit 102, and the non-absorption light intensity acquisition unit 108 acquires the light intensity, at time t, of the time-resolved waveform of the short pulsed light in the skin model from the time-resolved waveform storage unit 103.

Next, the optical absorption coefficient calculation unit 109 calculates the optical absorption coefficient of the dermis of the skin based on the light intensity acquired by the measurement light intensity acquisition unit 106, the optical path length of each layer of the skin acquired by the optical path length acquisition unit 107, and the light intensity acquired by the non-absorption light intensity acquisition unit 108. The concentration calculation unit 110 calculates the glucose concentration in the dermis based on the optical absorption coefficient calculated by the optical absorption coefficient calculation unit 109.

Accordingly, it is possible to reduce effects of noise due to layers other than the dermis and calculate the concentration of the glucose contained in the dermis.

Next, operation of the blood sugar value measurement apparatus 100 will be described.

The blood sugar value measurement apparatus 100 should calculate the optical propagation path length distribution and the time-resolved waveform in each layer of the skin model in advance, before measuring the blood sugar value.

Since a method of calculating the optical propagation path length distribution and the time-resolved waveform of the skin model is the same as that in the first embodiment, a description thereof will be omitted.

A structure of skin tissue that is an observed object will be described based on FIG. 15.

Figure 15:
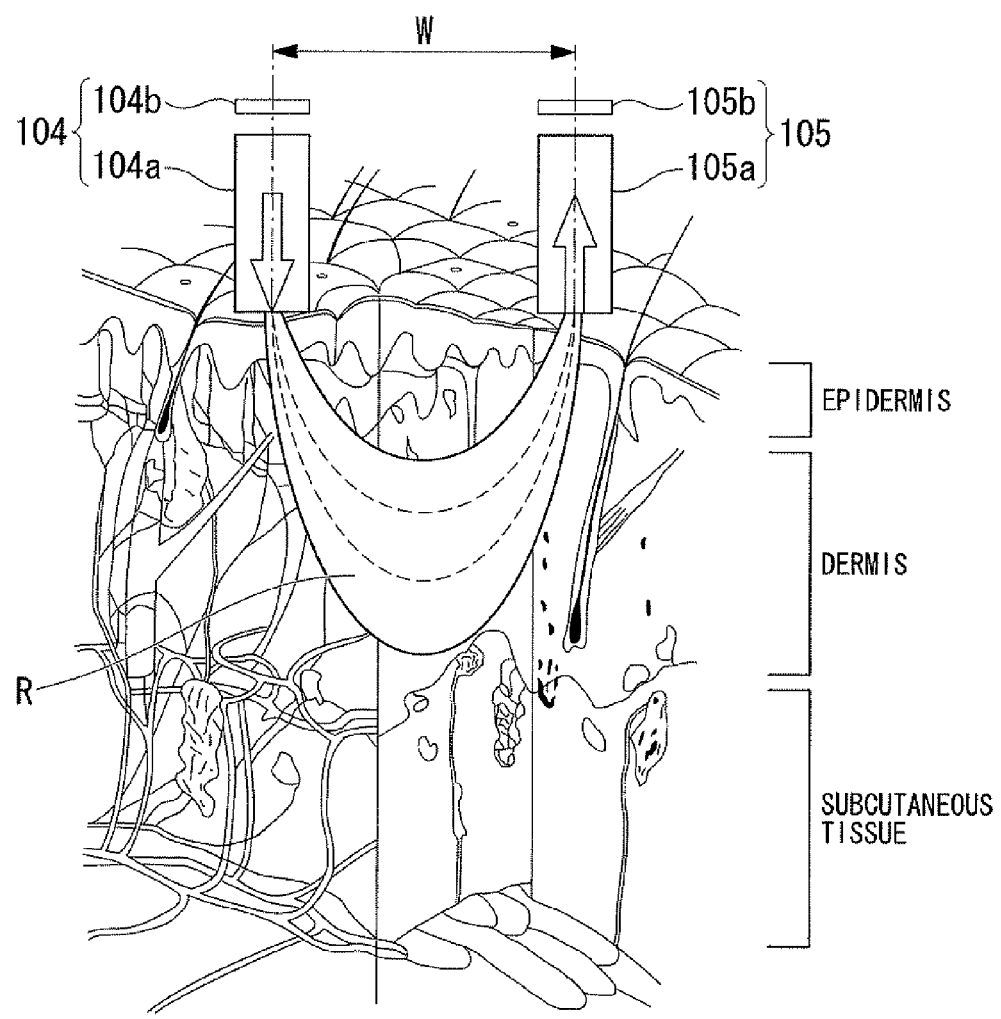
FIG. 15 is a cross-sectional view of skin tissue.

As shown in FIG. 15, skin tissue of a human is formed of three layers of an epidermis, a dermis, and subcutaneous tissue. The epidermis is an outermost thin layer having a thickness of 0.2 to 0.3 mm, and includes a corneous layer, a granular layer, a stratum spinosum, a bottom and the like. The dermis layer has a thickness of 0.5 to 2 mm between the epidermis and the subcutaneous tissue, and includes nerves, hair roots, sebaceous glands or sweat glands, hair follicles, blood vessels, and lymph nodes. The subcutaneous tissue is a layer having a thickness of 1 to 3 mm below the dermis, and most of the subcutaneous tissue is formed of subcutaneous fat.

Capillaries and the like are developed in the dermis, rapid material movement according to blood glucose occurs, and a glucose concentration in the dermis is considered to be changed with blood glucose concentration (blood sugar value). Therefore, the blood sugar value measurement apparatus 100 measures the glucose concentration in the dermis by irradiating light from the irradiation unit 104 to a surface of the skin tissue and detecting back-scattered light transmitting the skin tissue and being diffused using a light receiving unit 105.

The irradiation unit 104 includes a light source 104b, and an irradiation optical fiber 104a for transferring light radiated from the light source 104b to the epidermis. The light receiving unit 105 includes a photoelectric conversion element 105b, and a light receiving optical fiber 105a for transferring light output from the epidermis after transmitting the skin tissue and being diffused, to the photoelectric conversion element 105b. The irradiation optical fiber 104a and the light receiving optical fiber 105a are fixed to a probe apparatus so that optical axes (central axes of the cores) are in parallel in a state in which centers of the optical fiber cores are separated by a given irradiation light reception interval.

A path distribution R of the light arriving at the light receiving optical fiber 105a has a U shape. In fact, there are a plurality of U-shaped paths as indicated by a dotted line, and a propagation distance and a propagation time of light in each path differ from each other. An arrival depth of such a path distribution in the skin tissue is changed with an interval between the irradiation unit 104 and the light receiving unit 105, specifically, an irradiation light reception interval W that is a distance between centers of the cores of the irradiation optical fiber 104a and the light receiving optical fiber 105a. Accordingly, it is possible to measure an absorption spectrum of light mainly transmitting the dermis by appropriately setting the irradiation light reception interval W between the irradiation unit 104 and the light receiving unit 105.

Figure 16A:
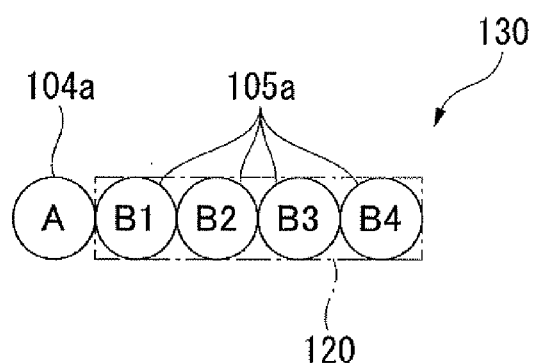
FIG. 16 is a cross-sectional view of a probe apparatus.
Figure 16B:
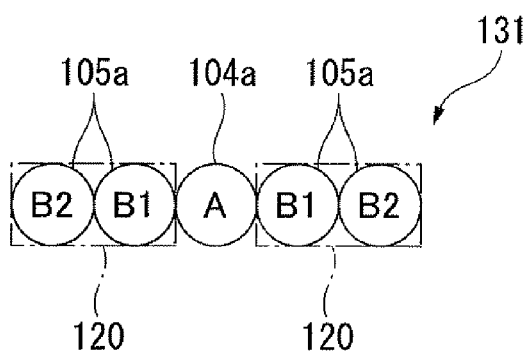
Figure 16C:
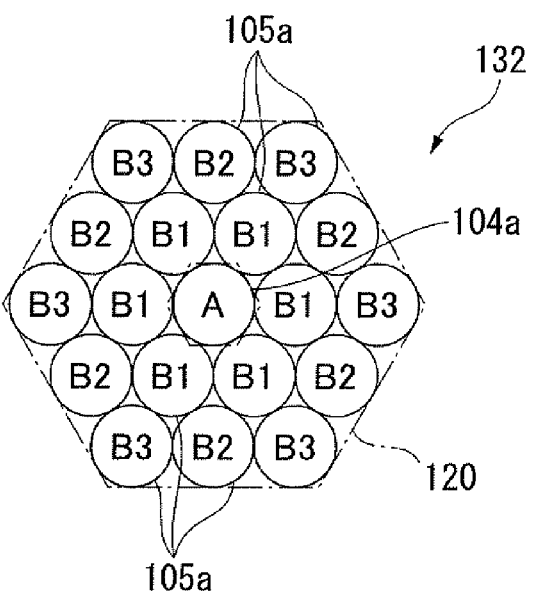

FIGS. 16A, 16B and 16C are cross-sectional views taken along a surface perpendicular to optical axes of the irradiation optical fiber 104a and the light receiving optical fiber 105a. Further, in FIGS. 16A, 16B, and 16C, an optical fiber indicated by reference numeral A is the irradiation optical fiber 104a and optical fibers indicated by reference numerals B1 to B4 are light receiving optical fibers 105a.

The probe apparatus 130 of FIG. 16A includes one irradiation optical fiber 104a arranged at a left end, and a plurality of light receiving optical fibers 105a arranged at regular intervals at a right end. In the probe apparatus 130, the irradiation optical fiber 104a and the light source 104b (see FIG. 15) correspond to an irradiation unit of the present invention, and a plurality of light receiving optical fibers 105a and photoelectric conversion elements 105b (see FIG. 15) arranged around the irradiation optical fiber 104a and the light source 104b correspond to a light receiving unit of the present invention.

The irradiation optical fiber 104a and the light receiving optical fiber 105a are arranged in a row in a direction perpendicular to the optical axis. In the probe apparatus 130, a leading end portion of the irradiation optical fiber 104a and a leading end portion of the light receiving optical fiber 105a exposed to a leading end portion of the probe apparatus 130 are brought into contact with a skin surface so that a process of irradiating the short pulsed light to the skin tissue and the process of receiving the light obtained as the short pulsed light is backscattered by the skin tissue can be performed.

The plurality of light receiving optical fibers 105a include a first light receiving optical fiber 105a (indicated by reference numeral B1) arranged at a first irradiation light reception interval from the irradiation optical fiber 104a, a second light receiving optical fiber 105a (indicated by reference numeral B2) arranged at a second irradiation light reception interval greater than the first irradiation light reception interval at right, a third light receiving optical fiber 105a (indicated by reference numeral B3) arranged at a third irradiation light reception interval greater than the second irradiation light reception interval at right, and a fourth light receiving optical fiber 105a (indicated by reference numeral B4) arranged at a fourth irradiation light reception interval greater than the third irradiation light reception interval at right.

For the plurality of light receiving optical fibers 105a, one or a plurality of light receiving optical fibers 105a are selected and used according to a depth of arrival at the skin tissue. For example, a method of selecting the first light receiving optical fiber 105a (indicated by reference numeral B1) at the smallest irradiation light reception interval when a spectrum of light transmitting the epidermis is desired to be accurately measured, and selecting the second light receiving optical fiber 105a (indicated by reference numeral B2) arranged at the second irradiation light reception interval and the third light receiving optical fiber 105a (indicated by reference numeral B3) arranged at the third irradiation light reception interval when a spectrum of light transmitting the dermis is desired to be accurately measured is used. Further, a thickness of the skin tissue differs from person to person. For example, the thickness of the skin tissue may differ between an adult and a child and between a man and a woman.

Thereby, even when information of the same dermis is obtained, the light receiving optical fiber 105a having a greater irradiation light reception interval may be considered to be used for a subject expected to have a thick epidermis and dermis, compared to a subject expected to be thin.

In FIG. 16A, the four light receiving optical fibers 105a have been shown, but the number of the light receiving optical fibers 105a is not limited thereto and may be three, five or more. A greater number of the light receiving optical fibers 105a enables the depth of arrival at the skin tissue to be controlled in a multi-step manner.

The probe apparatus 131 of FIG. 16B includes one irradiation optical fiber 104a arranged at a center thereof, and a plurality of light receiving optical fibers 105a arranged at regular intervals at both sides of the irradiation optical fiber 104a. In the probe apparatus 131, the irradiation optical fiber 104a and the light source 104b (see FIG. 15) correspond to an irradiation unit of the present invention, and the plurality of light receiving optical fibers 105a and photoelectric conversion elements 105b (see FIG. 15) arranged around the irradiation optical fiber 104a and the light source 104b correspond to a light receiving unit of the present invention.

The irradiation optical fiber 104a and the light receiving optical fiber 105a are arranged in a row in a direction perpendicular to optical axes. In the probe apparatus 131, a leading end portion of the irradiation optical fiber 104a and a leading end portion of the light receiving optical fiber 105a exposed to a leading end portion of the probe apparatus 131 are brought into contact with the skin surface so that the process of irradiating the short pulsed light to the skin tissue and the process of receiving the light obtained as the short pulsed light is backscattered by the skin tissue can be performed.

The plurality of light receiving optical fibers 105a include two first light receiving optical fibers 105a (indicated by reference numeral B1) arranged at a first irradiation light reception interval at both sides of the irradiation optical fiber 104a, and two second light receiving optical fibers 105a (indicated by reference numeral B2) arranged at a second irradiation light reception interval greater than the first irradiation light reception interval at both sides of the first light receiving optical fibers 105a.

For the plurality of light receiving optical fibers 105a, one or a plurality of light receiving optical fibers 105a are selected and used according to the depth of arrival at the skin tissue. For example, a method of selecting the first light receiving optical fiber 105a (indicated by reference numeral B1) at the smallest irradiation light reception interval when a spectrum of light transmitting the epidermis is desired to be accurately measured and selecting the first light receiving optical fiber 105a (indicated by reference numeral B1) arranged at the first irradiation light reception interval and the second light receiving optical fiber 105a (indicated by reference numeral B2) arranged at a second irradiation light reception interval when a spectrum of light transmitting the dermis is desired to be accurately measured is used. The probe apparatus 131 of FIG. 16B has a smaller selectable irradiation light reception interval than the probe apparatus 130 of FIG. 16A, but the light reception intensity is great because a plurality of light receiving optical fibers 105a are provided for one irradiation light reception interval. Thereby, low-noise measurement is possible.

In FIG. 16B, the light receiving optical fibers 105a having the two different types of irradiation light reception intervals have been shown, but the irradiation light reception intervals are not limited to the two types and may be three types. For example, when the measurement is performed at three types of irradiation light reception intervals, two third light receiving optical fibers 105a arranged at a third irradiation light reception interval greater than the second irradiation light reception interval may be provided at both sides of the second light receiving optical fibers 105a. The same applies to a case in which the irradiation light reception intervals are four types.

The probe apparatus 132 of FIG. 16C includes one irradiation optical fiber 104a arranged at a center thereof, and a plurality of light receiving optical fibers 105a arranged around the irradiation optical fiber 104a. In the probe apparatus 132, the irradiation optical fiber 104a and the light source 104b (see FIG. 15) correspond to an irradiation unit of the present invention, and the plurality of light receiving optical fibers 105a and photoelectric conversion elements 105b arranged around the irradiation optical fiber 104a and the light source 104b (see FIG. 15) correspond to a light receiving unit of the present invention.

The irradiation optical fiber 104a and the light receiving optical fiber 105a are arranged to be closely filled within a plane perpendicular to the optical axis. That is, the light receiving optical fibers 105a are arranged radially to have an interior angle of 60° around the irradiation optical fiber 104a. In the probe apparatus 132, a leading end portion of the irradiation optical fiber 104a and a leading end portion of the light receiving optical fiber 105a exposed to a leading end portion of the probe apparatus 132 are brought into contact with the skin surface so that the process of irradiating the short pulse to the skin tissue and the process of receiving the light obtained as the short pulsed light is backscattered by the skin tissue can be performed.

The plurality of light receiving optical fibers 105a include six first light receiving optical fibers 105a (indicated by reference numeral B1) arranged at a first irradiation light reception interval around the irradiation optical fiber 104a, six second light receiving optical fibers 105a (indicated by reference numeral B2) arranged at a second irradiation light reception interval greater than the first irradiation light reception interval around the first light receiving optical fibers 105a, and six third light receiving optical fibers 105a (indicated by reference numeral B3) arranged at a third irradiation light reception interval greater than the second irradiation light reception interval around the first light receiving optical fibers 105a.

For the plurality of light receiving optical fibers 105a, one or a plurality of light receiving optical fibers 105a are selected and used according to the depth of arrival at the skin tissue. Since the probe apparatus 132 of FIG. 16C has a greater number of light receiving optical fibers 105a provided at one irradiation light reception interval than the probe apparatus 131 of FIG. 16B, lower-noise measurement is possible.

Further, in FIGS. 16B and 16C, a plurality of light receiving optical fibers 105a are provided at one irradiation light reception interval. In this case, light transferred by the plurality of light receiving optical fibers 105a may be converted to an electric signal by the photoelectric conversion element provided for each light receiving optical fiber, and light transferred by the plurality of light receiving optical fibers 105a arranged at the same irradiation light reception interval may be focused on the same light receiving surface of the same photoelectric conversion element by the focusing element and converted collectively into an electric signal. When the latter method is used, the photoelectric conversion element can be common to the plurality of light receiving optical fibers 105a, thereby reducing cost of the members.

When one photoelectric conversion element is provided for each light receiving optical fiber, one light receiving unit is configured of one light receiving optical fiber and one photoelectric conversion element. When one photoelectric conversion element is provided for a plurality of light receiving optical fibers, one light receiving unit is configured of a plurality of light receiving optical fibers and one photoelectric conversion element.

The irradiation optical fiber 104a and the light receiving optical fiber 105a preferably are dispersion-compensation-type single-mode optical fibers for compensating for wavelength dispersion of light having a plurality of wavelengths 1 to q irradiated by the irradiation unit 104. Accordingly, it is possible to reduce a measurement error caused by the wavelength dispersion.

The irradiation optical fiber 104a and the light receiving optical fiber 105a may be multimode optical fibers that are not of a dispersion compensation type. Use of the multimode optical fiber increases a light receiving area (core diameter) compared to the use of a single-mode optical fiber, enabling low-noise measurement. However, since a measurement error caused by the wavelength dispersion becomes greater, lengths of the irradiation optical fiber 104a and the light receiving optical fiber 105a are preferably set so that a group delay time difference due to the wavelength dispersion of the light having a plurality of wavelengths 1 to q irradiated by the irradiation unit 104 is shorter than a propagation time corresponding to a peak of the optical propagation path length distribution of the epidermis, which is a layer closest to the surface among a plurality of light scattering medium layers included in the skin tissue.

For example, a case in which a step-index-type multimode optical fiber is used is considered. A group delay time difference of the step-index-type multimode optical fiber is expressed by the following equation (21):

$$\Delta Tm = (1/\cos \theta c - 1)To \approx To\Delta = (Ln1/c)\Delta \qquad (21)$$

Here, To denotes a group delay time of the fastest light going on the optical axis of the optical fiber, $\Delta$ denotes a fractional refractive index change (=1%) between a core and a cladding of the optical fiber, $\theta c$ denotes a critical angle, n1 denotes a refractive index of the core, L denotes a length of the optical fiber, and c denotes the speed of light. To denotes a path having the shortest propagation distance among a plurality of paths passing through the dermis shown in FIG. 15, i.e., a light path in which a depth of arrival of the short pulsed light is near a boundary between the epidermis and the dermis. A multimode fiber in which $\Delta Tm$ is smaller than the shortest arrival time of a dermis propagation light can increase the light intensity of a signal light compared to a single-mode fiber.

For example, when the group delay time difference is within 1.0 ps, a length of the light receiving optical fiber 105a for receiving light intensity is calculated to be 20 mm from Equation (21), in which the refractive index of the core is 1.5 and the speed of light is $3 \times 10^8$ m/s.

Geometrically describing propagation of the light in the multimode fiber, light at an angle $\theta 1$ with respect to the optical axis is $d = h/(\cos \theta 1)$ while light going along the optical axis ($\theta 1 = 0$) is h. Since $\cos \theta 1 = n2/n1$ (where, n2 denotes a refractive index of the cladding and n1 denotes a refractive index of the core) according to Snell's law, $d = h(n1/n2)$.

Here, since a fractional refractive index change $\Delta$ (=1−n2/n1) is 1%, n1/n2=1.01. Accordingly, d=1.01×h. Since h=20 mm, d=20.2 mm. That is, a propagation path difference between h and d when h is 20 mm, d−h, is equal to 0.2 mm. Since the speed v of light going into a material having a refractive index n is equal to the speed of light in air/n, $v = 3 \times 10^8 / 1.5 = 2 \times 10^8$ m/s. Accordingly, propagation path difference=propagation time difference t×speed of light=20 mm from a relationship that propagation time difference t=propagation path difference/speed of light.

Next, an operation in which the blood sugar value measurement apparatus 100 measures the blood sugar value will be described.

Figure 17:
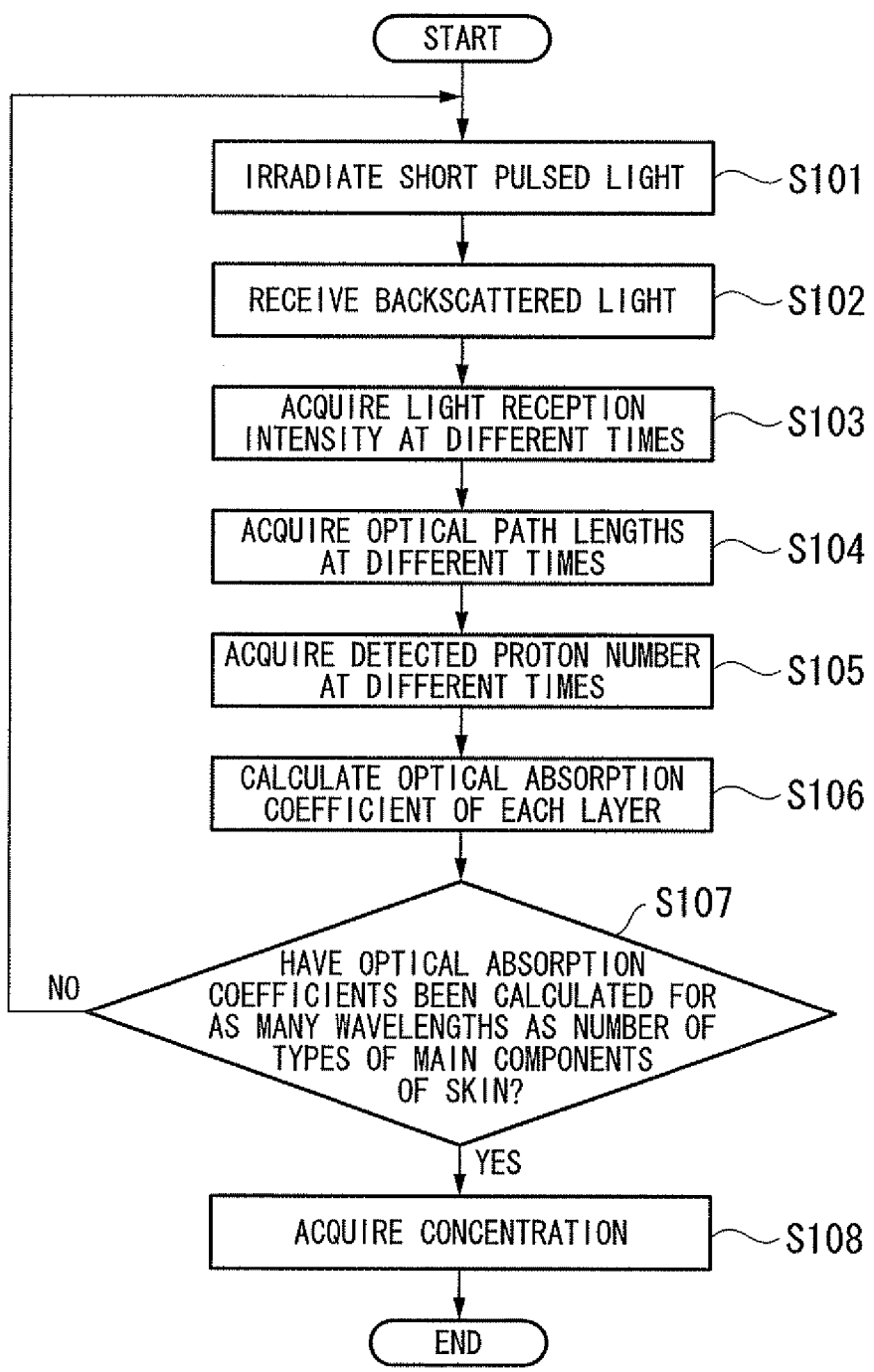
FIG. 17 is a first flowchart showing an operation in which the blood sugar value measurement apparatus measures a blood sugar value.

FIG. 17 is a first flowchart showing an operation in which the blood sugar value measurement apparatus measures a blood sugar value.

First, when the user operates the blood sugar value measurement apparatus 100 by putting the blood sugar value measurement apparatus 100 to the skin and pressing a measurement initiation switch (not shown), the irradiation unit 104 irradiates short pulsed light having a wavelength $\lambda_1$ to the skin (step S101). Here, the wavelength $\lambda_1$ is one of a plurality of wavelengths for which the simulation unit 101 calculates the optical propagation path length distribution and the time-resolved waveform.

When the irradiation unit 104 irradiates the short pulsed light, the light receiving unit 105 receives light irradiated from the irradiation unit 104 and backscattered by the skin (step S102). In this case, the light receiving unit 105 registers light reception intensity per unit time (e.g., 1 picosecond) from irradiation initiation in the internal memory.

Here, the light receiving unit 105 as a target is a specific light receiving unit selected from among a plurality of light receiving units provided in the light receiving unit. Each of the plurality of light receiving units 105 provided in the light receiving unit stores an electric signal according to a light reception amount, as light reception intensity, in an internal memory, which is not shown. However, all data of the light reception intensity is not acquired by the optical absorption coefficient calculation unit 109, but data of the light reception intensity stored in the internal memory of the specific light receiving unit 105 is selectively acquired by the optical absorption coefficient calculation unit 109. That is, the optical absorption coefficient calculation unit 109 corresponds to a selection unit of the present invention. The optical absorption coefficient calculation unit 109 may select a light receiving unit directly or indirectly selected by the user according to a menu screen or a light receiving unit set as default in advance. Examples of the former include selecting a light receiving unit by the user directly manipulating a display button such as "light receiving unit 1" or "light receiving unit 2" or selecting a light receiving unit by the user selecting age, gender or the like of a subject in a menu screen and indirectly selecting the light receiving unit associated with the age, the gender or the like.

When the light receiving unit 105 completes light reception, the measurement light intensity acquisition unit 106 acquires as many light reception intensities I(t) at different times t as the number of the layers of the skin, which have been stored in the internal memory of the specific light receiving unit 105 selected by the optical absorption coefficient calculation unit 109 (step S103). That is, the measurement light intensity acquisition unit 106 acquires light reception intensities $I(t_1)$ to $I(t_3)$ at three different times $t_1$ to $t_3$. Here, the reason why as many light reception intensities as the number of the layers of the skin are acquired is that the absorption coefficient of each layer of the skin is calculated using a simultaneous equation in a process which will be described later.

Further, the times $t_1$ to $t_3$ when the measurement light intensity acquisition unit acquires the light intensities may be times when the optical propagation path length distributions of the respective layers of the skin reach peaks. That is, a light intensity at a time obtained by adding a time when the optical path length of each layer of the skin is maximized in the graph shown in FIG. 3 to a time when the irradiation unit 104 has irradiated the short pulsed light may be acquired.

When the measurement light intensity acquisition unit 106 acquires the light reception intensities $I(t_1)$ to $I(t_3)$, the optical path length acquisition unit 107 acquires optical path lengths $L_1(t_1)$ to $L_1(t_3)$, $L_2(t_1)$ to $L_2(t_3)$, and $L_3(t_1)$ to $L_3(t_3)$ of the respective layers of the skin at times $t_1$ to $t_3$ from the optical propagation path length distribution of the wavelength $\lambda_1$ stored in the optical path length distribution storage unit 102 (step S104).

Further, when the measurement light intensity acquisition unit 106 acquires the light reception intensities $I(t_1)$ to $I(t_3)$, the non-absorption light intensity acquisition unit 108 acquires non-absorption light intensities $N(t_1)$ to $N(t_3)$ at times $t_1$ to $t_3$ from the time-resolved waveform of the wavelength $\lambda_1$ stored in the time-resolved waveform storage unit 103 (step S105).

When the optical path length acquisition unit 107 acquires the optical path length of each layer of the skin and the non-absorption light intensity acquisition unit 108 acquires the non-absorption light intensity, the optical absorption coefficient calculation unit 109 calculates optical absorption coefficients $\mu_1$ to $\mu_3$ of the respective layers of the skin based on Equation (22) (step S106). Here, the optical absorption coefficient $\mu_1$ indicates the optical absorption coefficient of the epidermis, the optical absorption coefficient $\mu_2$ indicates the optical absorption coefficient of the dermis, and the optical absorption coefficient $\mu_3$ indicates the optical absorption coefficient of the subcutaneous tissue layer:

$$\begin{cases} N'(t_1)\ln\left(\dfrac{N'(t_1)}{I'(t_1)}\right) = \sum_{i=1}^{3}\mu_i L_i(t_1) \\ N'(t_2)\ln\left(\dfrac{N'(t_2)}{I'(t_2)}\right) = \sum_{i=1}^{3}\mu_i L_i(t_2) \\ N'(t_3)\ln\left(\dfrac{N'(t_3)}{I'(t_3)}\right) = \sum_{i=1}^{3}\mu_i L_i(t_3) \end{cases} \quad (22)$$

$$\text{where } N'(t) = \dfrac{N(t)}{N_{in}}, \ I'(t) = \dfrac{I(t)}{I_{in}}$$

Here, ln(A) denotes a natural logarithm of A. Further, $I_{in}$ denotes the light intensity of the short pulsed light irradiated by the irradiation unit 104. Further, $N_{in}$ denotes the number of photons for which the simulation unit 101 has performed irradiation simulation.

When the optical absorption coefficient calculation unit 109 calculates the optical absorption coefficients $\mu_1$ to $\mu_3$ of the respective layers of the skin, the optical absorption coefficient calculation unit 109 judges whether the optical absorption coefficient calculation unit 109 has calculated the optical absorption coefficients $\mu_1$ to $\mu_3$ for the number of types of wavelength satisfying xC2≥α(e.g., α=3→x=3, α=4→x=4, and α=5→x=4) as the number α of types of an obtained component (step S107). In the present embodiment, since blood sugar value measurement is performed with the main components of the skin including four types of water, protein, lipid and glucose, the optical absorption coefficient calculation unit 109 judges whether the optical absorption coefficient calculation unit 109 has calculated optical absorption coefficients $\mu_1$ to $\mu_3$ for the four types of wavelengths $\lambda_1$ to $\lambda_4$. Here, the wavelengths $\lambda_1$ to $\lambda_4$ are selected from among the plurality of wavelengths for which the simulation unit 101 has calculated the optical propagation path length distribution and the time-resolved waveform.

When the optical absorption coefficient calculation unit 109 judges that there are wavelengths $\lambda_1$ to $\lambda_4$ for which the optical absorption coefficients $\mu_1$ to $\mu_3$ have not been calculated (step S107: NO), the process returns to step S1 to calculate the optical absorption coefficients $\mu_1$ to $\mu_3$ of the wavelengths $\lambda_1$ to $\lambda_4$ for which the optical absorption coefficients $\mu_1$ to $\mu_3$ have not yet been calculated.

On the other hand, when it is judged that the optical absorption coefficient calculation unit 109 has calculated the optical absorption coefficients $\mu_1$ to $\mu_3$ of the wavelengths $\lambda_1$ to $\lambda_4$ (step S107: YES), the concentration calculation unit 110 calculates the concentration of the glucose contained in the dermis using Equation (23) (step S108):

$$\begin{cases} \mu_{2(1)} - \mu_{2(2)} = \sum_{i=1}^{4} g_i(\varepsilon_{i(1)} - \varepsilon_{i(2)}) \\ \vdots \\ \mu_{2(4)} - \mu_{2(1)} = \sum_{i=1}^{4} g_i(\varepsilon_{i(4)} - \varepsilon_{i(1)}) \end{cases} \quad (23)$$

where $\mu_{2(1)}$ to $\mu_{2(4)}$ denote the optical absorption coefficients of the wavelengths $\lambda_1$ to $\lambda_4$ in the dermis. Further, $g_1$ to $g_4$ denote molar concentrations of water, protein, lipid and glucose that are the main components of the skin in the dermis. Further, $\epsilon_{1(1)}$ to $\epsilon_{1(4)}$ denote molar absorption coefficients of the water for the wavelengths $\lambda_1$ to $\lambda_4$, $\epsilon_{2(1)}$ to $\epsilon_{2(4)}$ denote molar absorption coefficients of the protein for the wavelengths $\lambda_1$ to $\lambda_4$, $\epsilon_{3(1)}$ to $\epsilon_{3(4)}$ denote molar absorption coefficients of the lipid for the wavelengths $\lambda_1$ to $\lambda_4$, and $\epsilon_{4(1)}$ to $\epsilon_{4(4)}$ denote molar absorption coefficients of the glucose for the wavelengths $\lambda_1$ to $\lambda_4$.

That is, the molar concentration of the glucose contained in the dermis can be obtained by calculating $g_4$ of Equation (23).

A reason why the molar concentration of the glucose can be obtained by Equation (23) will be described herein. Since wavelength dependence of a scattering coefficient of the skin is small, a change of the non-absorption light intensity N(t) and the optical path length $L_n(t)$ according to the wavelength can be ignored. Further, absorbance=molar absorption coefficient×molar concentration according to Beer-Lambert's law. Accordingly, the non-absorption light intensity N(t) is deleted by time-resolved measurement obtained at two wavelengths, such that Equation (23) representing a relational expression of an absorption coefficient difference obtained in the dermis and a molar absorption coefficient of each component forming the skin can be derived.

Thus, according to the present embodiment, the short pulsed light is irradiated and the glucose concentration is determined based on the intensity of the light received at a given time. Accordingly, the absorption coefficient of the dermis can be selectively calculated from the light received at a given time. Accordingly, the glucose concentration of the specific layer of skin can be calculated, and an accurate blood sugar value can be calculated by reducing effects of noise due to other layers.

Further, in Equation (23), the molar concentration of the glucose was obtained based on a difference between the optical absorption coefficients at a plurality of wavelengths. However, the molar concentration of the glucose can be directly obtained based on Equations (24) and (25) irrespective of the difference between the optical absorption coefficients at the plurality of wavelengths.

Equation (24) represents the optical absorption coefficients $\mu_1$ to $\mu_3$ in the respective layers.

$$\begin{cases} \mu_{1(i)} = \varepsilon_{1(i)} g_{11} + \varepsilon_{2(i)} g_{21} + \varepsilon_{3(i)} g_{31} + \varepsilon_{4(i)} g_{41} \\ \mu_{2(i)} = \varepsilon_{1(i)} g_{12} + \varepsilon_{2(i)} g_{22} + \varepsilon_{3(i)} g_{32} + \varepsilon_{4(i)} g_{42} \\ \mu_{3(i)} = \varepsilon_{1(i)} g_{13} + \varepsilon_{2(i)} g_{23} + \varepsilon_{3(i)} g_{33} + \varepsilon_{4(i)} g_{43} \end{cases} \quad (24)$$

In Equation (24), $\mu_{1(i)}$ (i=1 to 4) denotes the optical absorption coefficient of the wavelength $\lambda_i$ (i=1 to 4) in the epidermis, $\mu_{2(i)}$ (i=1 to 4) denotes the optical absorption coefficient of the wavelength $\lambda_i$ (i=1 to 4) in the dermis, and $\mu_{3(i)}$ (i=1 to 4) denotes the optical absorption coefficient of the wavelength $\lambda_i$ (i=1 to 4) in the subcutaneous tissue layer. $\epsilon_{1(i)}$ denotes a molar absorption coefficient of the water for the wavelength $\lambda_i$ (i=1 to 4), $\epsilon_{2(i)}$ denotes a molar absorption coefficient of the protein for the wavelength $\lambda_i$ (i=1 to 4), $\epsilon_{3(i)}$ denotes a molar absorption coefficient of the lipid for the wavelength $\lambda_i$ (i=1 to 4), and $\epsilon_{4(i)}$ denotes a molar absorption coefficient of the glucose for the wavelength $\lambda_i$ (i=1 to 4). $g_{1j}$, $g_{2j}$, $g_{3j}$, and $g_{4j}$ (j=1 to 3) denote molar concentrations of water, protein, lipid and glucose that are the main components of the skin in a j layer. Here, j=1 indicates the epidermis, j=2 indicates the dermis, and j=3 indicates the subcutaneous tissue layer.

Equation (25) is an equation for obtaining the molar concentrations $g_{12}$, $g_{22}$, $g_{32}$ and $g_{42}$ of the water, the protein, the lipid, and the glucose in the dermis (j=2). A molar concentration of the glucose contained in the dermis can be obtained by calculating $g_{42}$ of Equation (25).

$$\begin{pmatrix} g_{12} \\ g_{22} \\ g_{32} \\ g_{42} \end{pmatrix} = \begin{pmatrix} \varepsilon_{1(1)} & \varepsilon_{2(1)} & \varepsilon_{3(1)} & \varepsilon_{4(1)} \\ \varepsilon_{1(2)} & \varepsilon_{2(2)} & \varepsilon_{3(2)} & \varepsilon_{4(2)} \\ \varepsilon_{1(3)} & \varepsilon_{2(3)} & \varepsilon_{3(3)} & \varepsilon_{4(3)} \\ \varepsilon_{1(4)} & \varepsilon_{2(4)} & \varepsilon_{3(4)} & \varepsilon_{4(4)} \end{pmatrix}^{-1} \begin{pmatrix} \mu_{2(1)} \\ \mu_{2(2)} \\ \mu_{2(3)} \\ \mu_{2(4)} \end{pmatrix} \quad (25)$$

(Fourth Embodiment)

Next, a fourth embodiment of the present invention will be described in detail.

A blood sugar value measurement apparatus of the fourth embodiment has the same configuration as the blood sugar value measurement apparatus 100 according to the third embodiment. Operations of the measurement light intensity acquisition unit 106, the optical path length acquisition unit 107, the non-absorption light intensity acquisition unit 108, and the optical absorption coefficient calculation unit 109 differ from those in the third embodiment.

Figure 18:
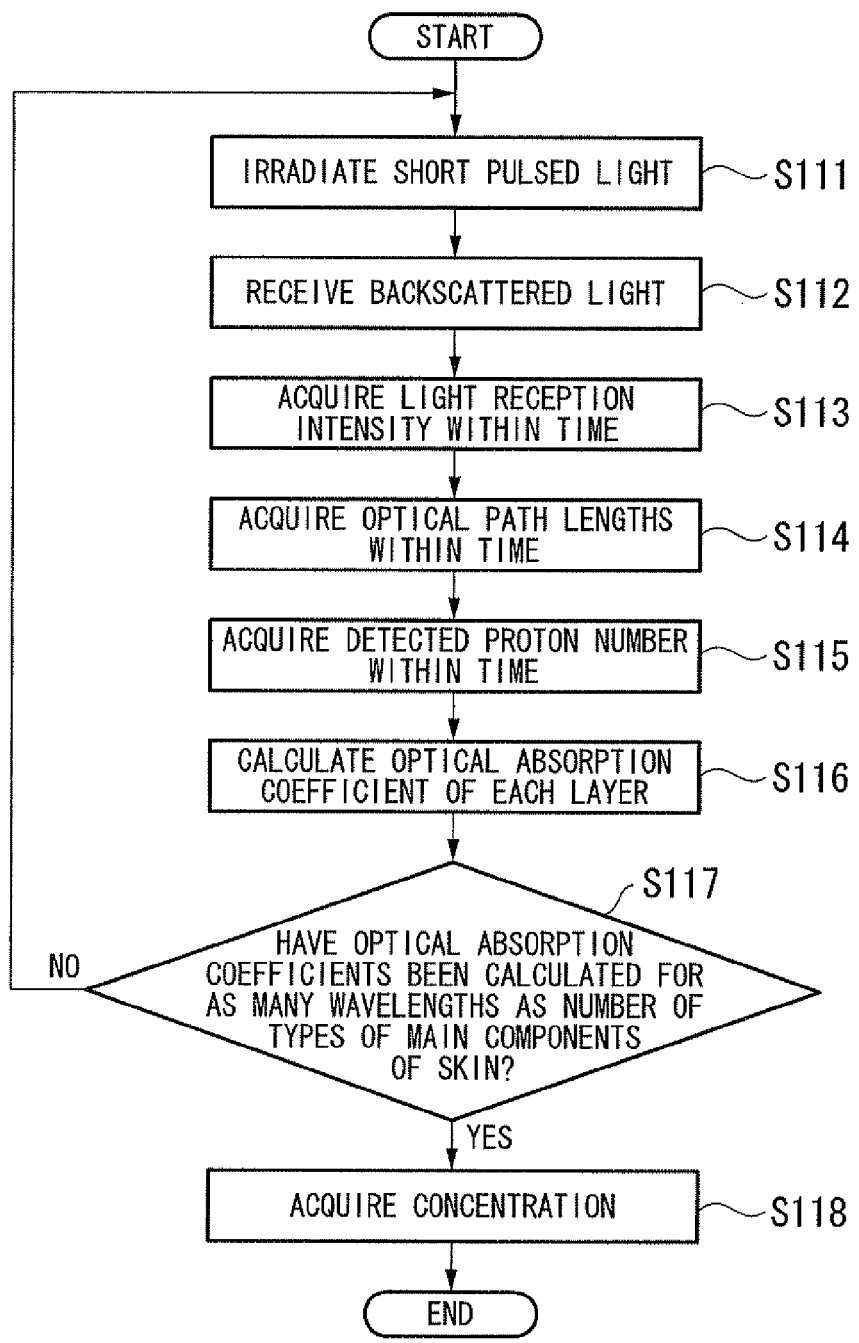
FIG. 18 is a second flowchart showing an operation in which the blood sugar value measurement apparatus measures a blood sugar value.

FIG. 18 is a second flowchart showing an operation in which the blood sugar value measurement apparatus measures the blood sugar value.

First, when the blood sugar value measurement apparatus 100 is operated, the irradiation unit 104 irradiates the short pulsed light having a wavelength $\lambda_1$ to the skin (step S111). Here, the wavelength $\lambda_1$ is one of the plurality of wavelengths for which the simulation unit 101 calculates an optical propagation path length distribution and a time-resolved waveform.

When the irradiation unit 104 irradiates the short pulsed light, the light receiving unit 105 receives light irradiated from the irradiation unit 104 and backscattered by the skin (step S112). In this case, the light receiving unit 105 registers light reception intensity per unit time (e.g., 1 picosecond) from irradiation initiation in the internal memory.

Figure 19:
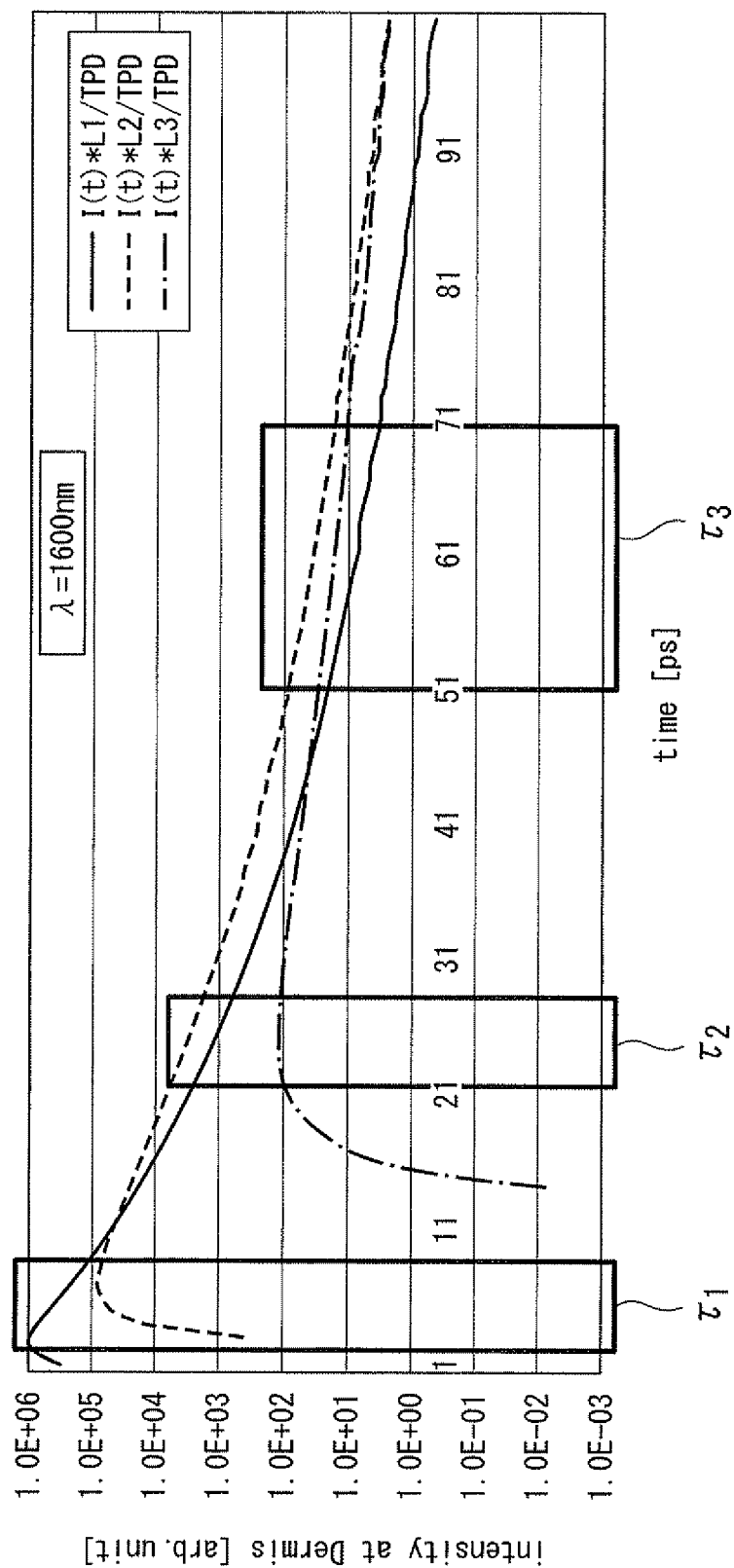
FIG. 19 is a diagram showing an optical path length at a given time acquired by an optical path length acquisition unit.

When the light receiving unit 105 completes light reception, the measurement light intensity acquisition unit 106 acquires a time distribution of the light reception intensity between any time and a time τ from the light reception intensities stored in the internal memory of the light receiving unit 105 (step S113). For a change of the light intensity up to the time τ, for example, times shown in FIG. 19 are selected. That is, when a spectrum of light transmitting the epidermis is desired to be accurately measured, a period τ1 of 1 ps to 10 ps is selected, when a spectrum of light transmitting the dermis is desired to be accurately measured, a period τ2 of 2 ps to 30 ps is selected, and when a spectrum of light transmitting the subcutaneous tissue is desired to be accurately detected, a period τ3 of 50 ps to 70 ps is selected. Since τ1, τ2, and τ3 do not overlap one another on a time axis, when a spectrum of light transmitting a layer close to the surface of the skin tissue is desired to be detected, a measurement initiation time and a measurement termination time are set early on the time axis.

When the measurement light intensity acquisition unit 106 acquires a time distribution of the light reception intensity up to the time τ, the optical path length acquisition unit 107 acquires optical path lengths $L_1$ to $L_3$ of the respective layers of the skin between any time and a time τ from an optical propagation path length distribution of the wavelength $\lambda_1$ stored in the optical path length distribution storage unit 102 (step S114).

Further, when the measurement light intensity acquisition unit 106 acquires the light reception intensity up to the time τ, the non-absorption light intensity acquisition unit 108 acquires non-absorption light intensity between any time and a time τ from the time-resolved waveform of the wavelength $\lambda_1$ stored in the time-resolved waveform storage unit 103 (step S115).

When the optical path length acquisition unit 107 acquires the optical path length of each layer of the skin and the non-absorption light intensity acquisition unit 108 acquires the non-absorption light intensity, the optical absorption coefficient calculation unit 109 calculates the optical absorption coefficients $\mu_1$ to $\mu_3$ of the respective layers of the skin using Equation (26) (step S116). Here, the optical absorption coefficient $\mu_1$ indicates the optical absorption coefficient of the epidermis, the optical absorption coefficient $\mu_2$ indicates the optical absorption coefficient of the dermis, and the optical absorption coefficient $\mu_3$ indicates the optical absorption coefficient of the subcutaneous tissue layer.

$$\begin{cases} \int_0^\tau \ln\left(\frac{N'(t)}{I'(t)}\right) L_1(t) dt = \sum_{i=1}^{3} \mu_i \int_0^\tau L_1(t) L_i(t) dt \\ \int_0^\tau \ln\left(\frac{N'(t)}{I'(t)}\right) L_2(t) dt = \sum_{i=1}^{3} \mu_i \int_0^\tau L_2(t) L_i(t) dt \\ \int_0^\tau \ln\left(\frac{N'(t)}{I'(t)}\right) L_3(t) dt = \sum_{i=1}^{3} \mu_i \int_0^\tau L_3(t) L_i(t) dt \end{cases} \quad (26)$$

$$\text{where } N'(t) = \frac{N(t)}{N_{in}}, I'(t) = \frac{I(t)}{I_{in}}$$

Here, ln(A) denotes a natural logarithm of A. Further, I(t) denotes light reception intensity of the light receiving unit 105 at time t and $I_{in}$ denotes the light intensity of the short pulsed light irradiated by the irradiation unit 104. Further, N(t) denotes the non-absorption light intensity of the time-resolved waveform at time t, and $N_{in}$ denotes the number of photons for which the simulation unit 101 performs irradiation simulation. Further, $L_1(t)$ to $L_3(t)$ denote optical path lengths of the respective layers of the skin at time t.

When the optical absorption coefficient calculation unit 109 calculates the optical absorption coefficients $\mu_1$ to $\mu_3$ of the respective layers of the skin, the optical absorption coefficient calculation unit 109 judges whether the optical absorption coefficient calculation unit 109 has calculated the optical absorption coefficients $\mu_1$ to $\mu_3$ for as many wavelengths as the number of types of the main components of the skin (step S117). In the present embodiment, since the blood sugar value measurement is performed using the four types of water, protein, lipid and glucose as the main components of the skin, the optical absorption coefficient calculation unit 109 judges whether the optical absorption coefficients $\mu_1$ to $\mu_3$ have been calculated for four types of wavelengths $\lambda_1$ to $\lambda_4$. Here, the wavelengths $\lambda_1$ to $\lambda_4$ are selected from among the plurality of wavelengths for which the simulation unit 101 has calculated the optical propagation path length distribution and the time-resolved waveform.

When it is judged that there are wavelengths $\lambda_1$ to $\lambda_4$ for which the optical absorption coefficient calculation unit 109 has not calculated the optical absorption coefficients $\mu_1$ to $\mu_3$ (step S117: NO), the process returns to step S1 to calculate the optical absorption coefficients $\mu_1$ to $\mu_3$ of the wavelengths $\lambda_1$ to $\lambda_4$ for which the optical absorption coefficients $\mu_1$ to $\mu_3$ have not yet been calculated.

On the other hand, when it is determined that the optical absorption coefficient calculation unit 109 has calculated the optical absorption coefficients $\mu_1$ to $\mu_3$ of the wavelengths $\lambda_1$ to $\lambda_4$ (step S117: YES), the concentration calculation unit 110 calculates the concentration of the glucose contained in the dermis using the above-described Equation (23) (step S118).

Thus, according to the present embodiment, the absorption coefficients $\mu_1$ to $\mu_3$ are calculated using an integral value of the optical path length up to time τ. Accordingly, it is possible to reduce effects of an error included in the measured light reception intensity I(t) on the result of calculation of the absorption coefficients $\mu_1$ to $\mu_3$.

Further, the case in which the concentration determination method is applied to the blood sugar value measurement apparatus 100 to measure the concentration of the glucose contained in the dermis of the skin has been described in the above-described embodiment, but the present invention is not limited thereto. The concentration determination method may be used for another apparatus for determining a concentration of a target component in any layer of an observed object fanned of a plurality of light scattering medium layers.

The above-described blood sugar value measurement apparatus 100 has a computer system therein. The operation of each processing unit described above is stored as a program format in a computer-readable recording medium. When the program is read and executed by the computer, the process is performed. Here, the computer-readable recording medium may include a magnetic disk, a magneto-optical disc, a CD-ROM, a DVD-ROM, a semiconductor memory, etc. Further, the computer program is distributed to a computer by a communication line so that the program is executed by the computer.

Further, the program may be a program for realizing part of the above-described function.

Further, the program may be a difference file (a difference program) that can realize the above-described function in combination with a program that has already been recorded in a computer system.

(Fifth Embodiment)

A fifth embodiment of the present invention will be described. Here, a description will be given in which a blood sugar value measurement apparatus is used as a concentration determination apparatus, skin of a person's palm is used as an observed object, glucose is used as a target component, and short pulsed light having a specific wavelength is used as light having a specific wavelength.

Figure 20:
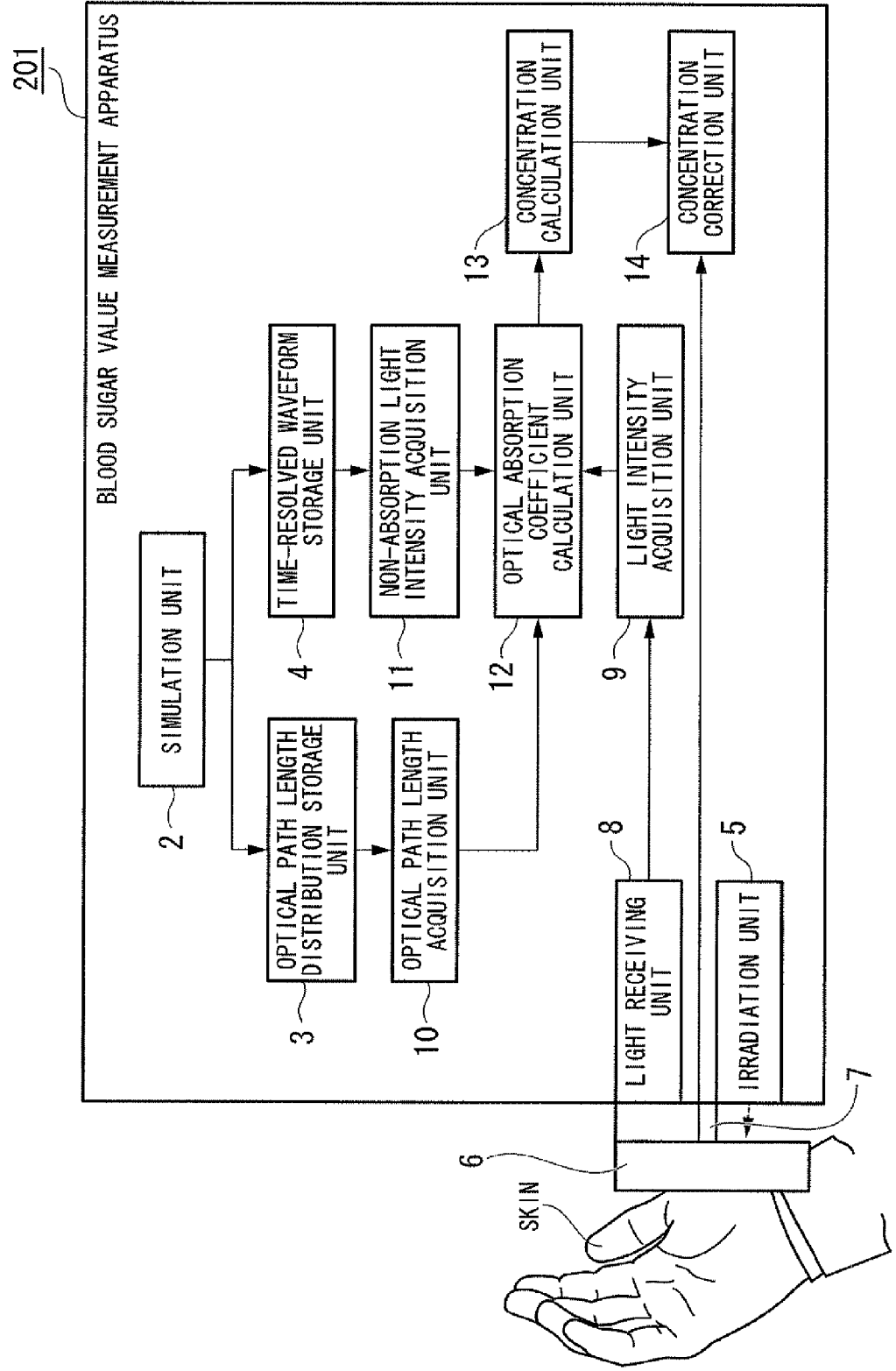
FIG. 20 is a schematic block diagram showing a configuration of a blood sugar value measurement apparatus of a fifth embodiment of the present invention.
Figure 21:
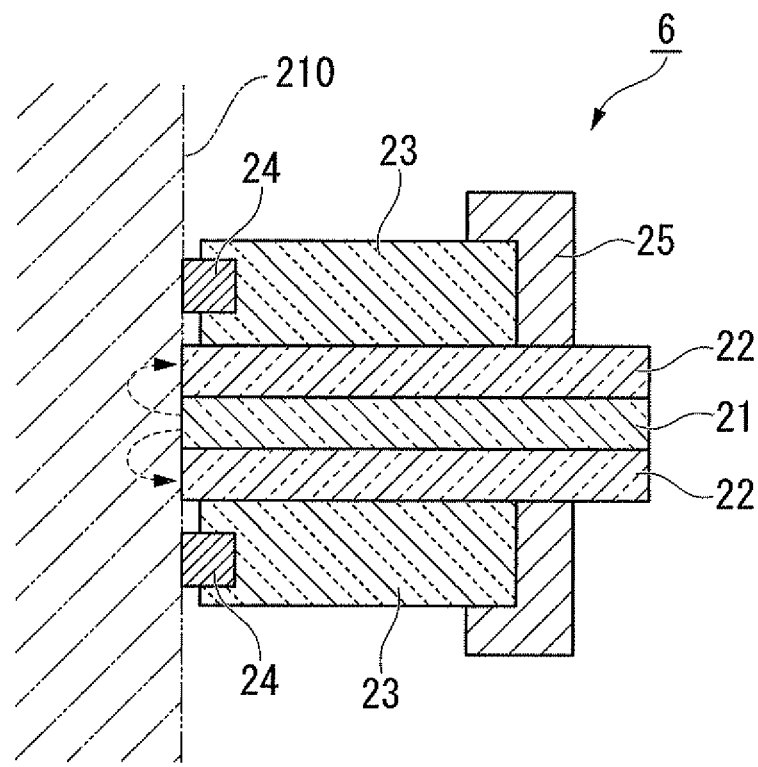
FIG. 21 is a cross-sectional view showing a configuration of a light guide unit of a blood sugar value measurement apparatus of a fifth embodiment of the present invention.

FIG. 20 is a schematic block diagram showing a configuration of a blood sugar value measurement apparatus of the fifth embodiment of the present invention. FIG. 21 is a cross-sectional view schematically showing a configuration of a light guide unit of the blood sugar value measurement apparatus.

A blood sugar value measurement apparatus 201 is an apparatus for noninvasively determining a concentration of glucose (a target component) included in a dermis (any layer) of a plurality of layers constituting skin (an observed object) of, for example, a palm. The blood sugar value measurement apparatus 201 includes a simulation unit 2, an optical path length distribution storage unit 3, a time-resolved waveform storage unit 4, an irradiation unit 5, a light guide unit 6, a light scattering medium layer selection unit 7, a light receiving unit 8, a light intensity acquisition unit 9, an optical path length acquisition unit 10, a non-absorption light intensity acquisition unit (light intensity model acquisition unit) 11, an optical absorption coefficient calculation unit 12, a concentration calculation unit 13, and a concentration correction unit 14.

The simulation unit 2 performs simulation for irradiating light to a skin model having an optical absorption coefficient of 0.

The optical path length distribution storage unit 3 stores a model of an optical propagation path length distribution in each layer constituting the skin, of short pulsed light irradiated to the skin. Here, the optical path length distribution storage unit 3 stores the optical propagation path length distribution of the skin model having the optical absorption coefficient of 0.

The time-resolved waveform storage unit 4 stores a model of a time-resolved waveform of the short pulsed light irradiated to the skin. Here, the time-resolved waveform storage unit 4 stores the time-resolved waveform of the skin model having the optical absorption coefficient of 0.

The irradiation unit 5 irradiates the short pulsed light to the skin. Here, the short pulsed light refers to pulsed light having a pulse width of about 100 psec or less. Alternatively, a pulsed light having a pulse width in a range of 0.1 psec to a few psec may be used as the short pulsed light.

As shown in FIG. 21, the light guide unit 6 includes an irradiation guide path 21 adhered to the skin 210 for guiding the short pulsed light generated from the irradiation unit 5 to the skin 210, a light reception guide path 22 provided integrally outside the irradiation guide path 21 for focusing plural types of backscattered light radiated from the skin 210 and guiding the light to the light scattering medium layer selection unit 7, a heat insulating material 23 provided outside the irradiation guide path 21 and the light reception guide path 22, which are formed integrally, a temperature sensor (temperature measurement unit) 24 provided in a surface, at a skin side, of the heat insulating material 23 for measuring a temperature of the dermis among the plurality of layers constituting the skin 210, and a base 25 for fixing the irradiation guide path 21, the light reception guide path 22 and the heat insulating material 23.

The irradiation guide path 21 and the light reception guide path 22 may be formed of a material having a small absorption lass of the guided short pulsed light. For example, quartz glass or plastic such as polymethylmethacrylate (PMMA) or polyethylene is suitably used.

The heat insulating material 23 may be a heat insulation material with sufficiently great heat capacity in a range not affecting a temperature change of the skin 210. It is preferable that an interval between the heat insulating material 23 and the skin 210 have such a size that the heat insulating material 23 does not directly receive the temperature change of the skin 210. The interval is preferably 0.5 mm to 1.0 mm. In the heat insulating material 23, the heat capacity is sufficiently small that it does not affect the temperature change of the skin 210, such that a thermal response time until reaching 90% of a temperature arrival value can be suppressed within 0.2 seconds.

The temperature sensor 24 measures a temperature of the dermis, which is at a depth of 0.3 mm to 1.5 mm from the surface of the skin 210, in a non-contact manner.

In the light guide unit 6, the irradiation guide path 21 guides the short pulsed light irradiated by the irradiation unit 5 and irradiates the short pulsed light to the skin 210. In this case, the short pulsed light is irradiated to the skin 210 and plural types of backscattered light are radiated from the skin 210. The plural types of backscattered light are guided to the light scattering medium layer selection unit 7 by the light reception guide path 22. After the short pulsed light is irradiated, the temperature sensor 24 measures a temperature of the dermis among the plurality of layers constituting the skin.

The temperature sensor 24 can measure temperature of the vicinity of the dermis among the plurality of layers constituting the skin without being affected by the temperature of the irradiation guide path 21 and the light reception guide path 22 because surroundings of the temperature sensor 24 are covered with the heat insulating material 23.

The light scattering medium layer selection unit 7 selects the backscattered light radiated by the dermis from among the plural types of backscattered light radiated from the skin, which have been focused and guided by the light guide unit 6.

The light receiving unit 8 receives the light obtained as the short pulsed light is backscattered by the skin.

The light intensity acquisition unit 9 acquires light reception intensities at a plurality of different times, of the backscattered light radiated from the dermis, which has been received by the light receiving unit 8.

Here, the plurality of times preferably include a peak time of the optical propagation path length distribution of each layer constituting the skin.

Thus, the inclusion of the peak time of the optical propagation path length distribution of each layer enables any layer from a plurality of layers of the skin, such as the dermis, to be efficiently selected.

The optical path length acquisition unit 10 acquires the optical path length of each layer of the skin, at a given time, of the model of the optical propagation path length distribution from the optical path length distribution storage unit 3. Here, the optical path length acquisition unit 10 acquires the optical path length at any time from the optical path length distribution storage unit 3.

The non-absorption light intensity acquisition unit 11 acquires light intensity, at a given time, of the model of the time-resolved waveform of the short pulsed light from the time-resolved waveform storage unit 4. Here, the non-absorption light intensity acquisition unit 11 acquires light intensity at any time from the time-resolved waveform storage unit 4.

The optical absorption coefficient calculation unit 12 calculates the optical absorption coefficient in the dermis of the skin to which the short pulsed light has been irradiated, using Equation (4).

The concentration calculation unit 13 calculates a concentration of the glucose contained in the dermis from the optical absorption coefficient in the dermis, using Equation (5).

The concentration correction unit 14 corrects the glucose concentration of the dermis calculated by the concentration calculation unit 13 using the temperature of the dermis measured by the temperature sensor 24.

The concentration correction unit 14 corrects the glucose concentration of the dermis calculated by the concentration calculation unit 13 using a difference between the temperature of the dermis measured by the temperature sensor 24 and a reference temperature, thereby suppressing effects of the temperature of the dermis on the glucose concentration of the dermis.

Accordingly, it is possible to suppress effects of the temperature of the dermis on the glucose concentration of the deaths and accurately measure the glucose concentration in a non-invasive manner.

In the thus configured blood sugar value measurement apparatus 1, short pulsed light having a continuous wavelength or a specific wavelength radiated from the irradiation unit 5 is irradiated to the skin 210 via the irradiation guide path 21. The plural types of backscattered light are radiated from the skin 210, but such backscattered light is focused by the light reception guide path 22 and guided to the light scattering medium layer selection unit 7.

Further, before and after the concentration of the backscattered light, the temperature sensor 24 measures the temperature of the dermis among the plurality of layers constituting the skin 210.

The light scattering medium layer selection unit 7 selects only the backscattered light radiated by the dermis from among the plural types of backscattered light radiated from the skin 210. The light receiving unit 8 receives only the backscattered light radiated from the dermis.

Further, the light intensity acquisition unit 9 acquires the light intensity of the backscattered light radiated from the dermis, which has been received by the light receiving unit 8 at time t.

Meanwhile, the optical path length acquisition unit 10 acquires the optical path length of each layer of the skin 210, at time t, of the optical propagation path length distribution in the skin model from the optical path length distribution storage unit 3, and the non-absorption light intensity acquisition unit 11 acquires light intensity, at time t, of the time-resolved waveform of the short pulsed light in the skin model from the time-resolved waveform storage unit 4.

Then, the optical absorption coefficient calculation unit 12 calculates the optical absorption coefficient of the dermis of the skin based on the light intensity acquired from the light intensity acquisition unit 9, the optical path length of each layer of the skin acquired by the optical path length acquisition unit 10, and the light intensity acquired by the non-absorption light intensity acquisition unit 11.

The concentration calculation unit 13 then calculates the concentration of the glucose contained in the dermis of the skin 20 based on the optical absorption coefficient calculated by the optical absorption coefficient calculation unit 12, using Equation (5).

Thus, the concentration of the glucose contained in the dermis is calculated.

The concentration correction unit 14 then corrects the glucose concentration of the dermis calculated by the concentration calculation unit 13 using the temperature of the dermis measured by the temperature sensor 24.

Such a correction of the glucose concentration of the dermis at any temperature using the temperature of the dermis measured by the temperature sensor 24 can reduce effects of the temperature on the glucose concentration of the dermis.

Thus, the correction of the concentration of the glucose contained in the dermis calculated based on the backscattered light radiated from the dermis using the temperature of the dermis measured by the temperature sensor 24 can suppress effects of the temperature of the dermis on the concentration of the glucose contained in the dermis. Accordingly, it is possible to accurately measure the concentration of the glucose contained in the dermis in a non-invasive manner.

Since the operation of the blood sugar value measurement apparatus 201 is the same as that in the first embodiment, a description thereof will be omitted.

Further, the following can be seen from FIG. 10.

For example, since the absorbance is about 0.035 with a glucose amount of 9.4 g/dl at a wavelength of 1600 nm, the absorption coefficient is about 0.08/mm. Meanwhile, since a normal value of a glucose amount is about 100 mg/dl in the dermis, an absorption coefficient corresponding to this normal value is about 0.0008/mm.

Effects of the temperature will be described with reference to FIG. 9.

In FIG. 9, since an absorbance difference is about −0.008 with a rise of 4° C. at a wavelength of 1600 nm, a change of the absorption coefficient is about −0.02/mm.

Here, if it is assumed that the absorbance change is linear with a temperature change, the change amount of the absorption coefficient is −0.004/mm when the temperature rises by 1° C. That is, it can be seen that the rise of 1° C. corresponds to the glucose concentration reduction of 500 mg/dl.

This is a correction value in the result of obtaining absorbance spectra with a cell length of 1 mm and at sample temperatures of 21° C. and 41° C. using an absorptiometer.

Further, an absorbance change due to the glucose concentration in actual skin increases by one digit more than the result of obtaining an absorbance spectrum with a cell length of 1 mm at sample temperatures of 21° C. and 41° C. using an absorptiometer after an optical path length extends due to scattering in the skin. Accordingly, a correction value of the absorption coefficient with respect to the temperature change in the actual skin also increases by one digit.

Next, a process of measuring a blood sugar value using the blood sugar value measurement apparatus 201 will be described based on FIG. 22.

First, a user operates the blood sugar value measurement apparatus 201 by putting the blood sugar value measurement apparatus 201 to skin of, for example, his or her wrist and pressing a measurement initiation switch (not shown).

Here, the temperature sensor 24 measures the temperature of the dermis 230 constituting the skin 210 (step S201).

Meanwhile, the irradiation unit 5 irradiates the short pulsed light to the dermis 230 constituting the skin 210 (step S202).

Then, the light guide unit 6 focuses the plural types of backscattered light radiated from the skin 210, i.e., the backscattered light radiated from the subcutaneous tissue 240, the dermis 230 and the epidermis 220, and guides the backscattered light to the light scattering medium layer selection unit 7.

The light scattering medium layer selection unit 7 selects the backscattered light radiated by the dermis 230 from among the backscattered light radiated from the subcutaneous tissue 240, the dermis 230 and the epidermis 220 focused and guided by the light guide unit 6 (step S203).

The light receiving unit 8 then receives the backscattered light per unit time radiated from the dermis 230 (step S204). In this case, the light receiving unit 8 records light reception intensity per unit time (e.g., time $t_1$ to $t_m$ per 1 picosecond) from irradiation initiation in an internal memory.

When the light intensity acquisition unit 9 is notified that the light receiving unit 8 has completed light reception, the light intensity acquisition unit 9 acquires light reception intensity of the backscattered light radiated from the dermis 230 at different times (step S205). That is, the light intensity acquisition unit 9 acquires the light intensity of the backscattered light at a plurality of times $t_1$ to $t_m$.

Here, times $t_1$ to $t_m$ when the light intensity acquisition unit 9 acquires the light intensity preferably include a time when the backscattered light radiated from the dermis 230 reaches a peak. That is, the time is preferably obtained by adding a time when the optical path length of the dermis 230 is maximized, to a time when the irradiation unit 5 has irradiated the short pulsed light.

Then, the optical absorption coefficient calculation unit 12 calculates the optical absorption coefficient of the dermis 230 based on the light reception intensities of the backscattered light radiated from the dermis 230 at different times, which has been acquired by the light intensity acquisition unit 9, i.e., the light intensity of the backscattered light at a plurality of times $t_1$ to $t_m$ using Equation (8) (step S206).

The concentration calculation unit 13 then calculates the concentration of the glucose contained in the dermis 230 based on the optical absorption coefficient μ of the dermis 230 calculated by the optical absorption coefficient calculation unit 12.

Further, since a method of calculating a glucose concentration is the same as that of the first embodiment, a description thereof will be omitted (step S207).

The concentration correction unit 14 then corrects the glucose concentration of the dermis 230 calculated by the concentration calculation unit 13 using the temperature of the dermis 230 measured by the temperature sensor 24, based on the following correction equation (step S208):

measured value of glucose concentration-value corresponding to absorption coefficient of water.

For example, when the temperature of the dermis 230 rises by T° C., a change amount of the absorption coefficient of the light is −0.004/mm×T. Accordingly, a reduction amount of the glucose concentration when the temperature of the dermis 230 rises by T° C. is 500 mg/dl×T.

The above-described blood sugar value measurement apparatus 1 includes a computer system therein, and the processing operation of each step described above is stored as a program format in a computer-readable recording medium. When the program is read and executed by the computer, the processing operation may be performed.

Here, the computer-readable recording medium may include a magnetic disk, a magneto-optical disc, a CD-ROM, a DVD-ROM, a semiconductor memory, etc.

Further, the computer program is distributed to a computer by a communication line so that the program is executed by the computer.

Further, the above program may realize a part of each step.

Further, the program may be a difference file (a difference program) that can realize the above-described function in combination with a program that has already been recorded in a computer system.

As described above, according to the present embodiment, when the short pulsed light is irradiated to the skin, the temperature of the dermis is measured, and the glucose concentration in the dermis of the skin calculated based on the backscattered light radiated from the dermis is corrected based on the measured temperature of the dermis, thereby reducing effects of the temperature on the glucose concentration in the dermis calculated based on the backscattered light. Thus, it is possible to reduce the effects of the temperature of the dermis on the glucose concentration and accurately measure the glucose concentration in a non-invasive manner.

(Sixth Embodiment)

Figure 23:
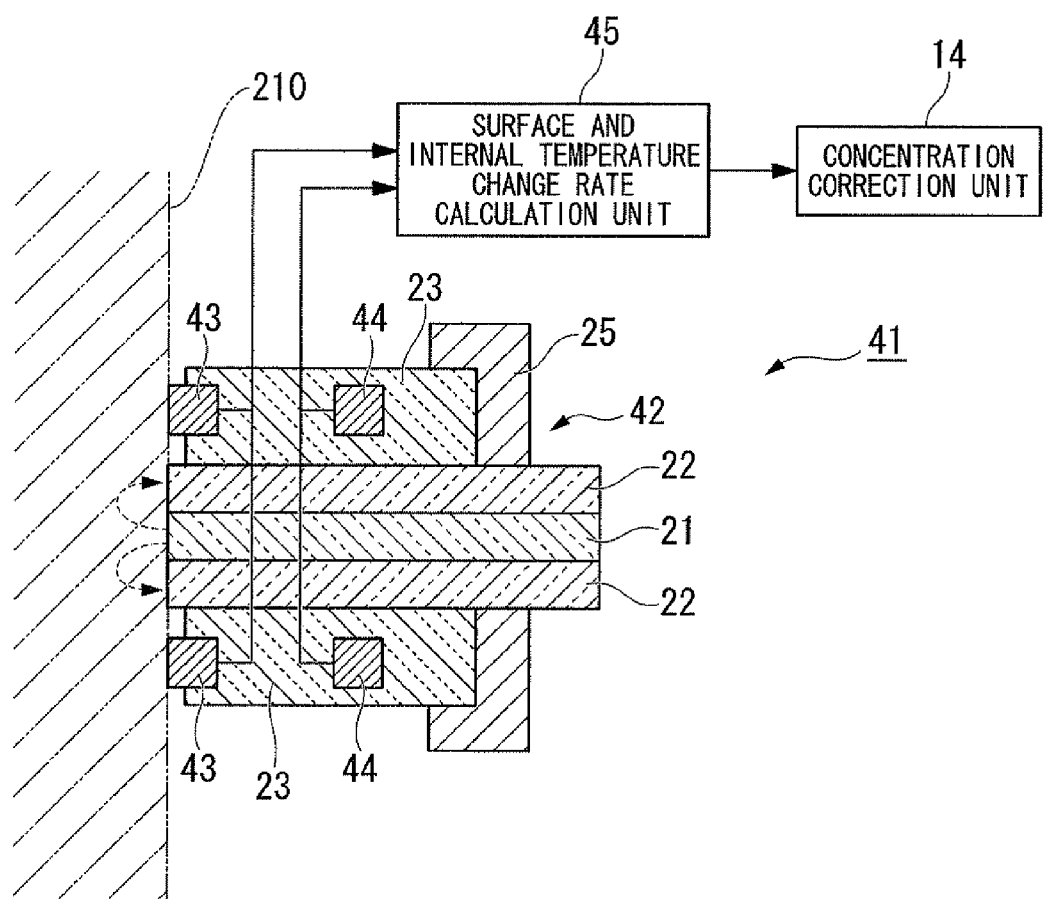
FIG. 23 is a cross-sectional view showing a configuration of a light guide unit of a blood sugar value measurement apparatus of a sixth embodiment of the present invention.

FIG. 23 is a cross-sectional view showing a schematic configuration of a light guide unit of a blood sugar value measurement apparatus (a concentration determination apparatus) of a sixth embodiment of the present invention. A difference between a light guide unit 42 of a blood sugar value measurement apparatus 41 of the present embodiment and the light guide unit 6 of the blood sugar value measurement apparatus 201 of the fifth embodiment is that the temperature sensor 24 is substituted with a surface temperature sensor (a surface temperature measurement unit) 43 for measuring a temperature of the surface of the skin 210, and an internal temperature sensor (an internal temperature measurement unit) 44 provided in the heat insulating material 23 for directly measuring a temperature of the surface temperature sensor 43, a surface and internal temperature change rate calculation unit (a surface and internal temperature change rate calculation unit) 45 for calculating, as a temperature change rate per unit time, a difference between the temperature of the dermis 230 measured by the surface temperature sensor 43 and the temperature of the vicinity of the surface temperature sensor 43 measured by the internal temperature sensor 44 is provided, and the surface and internal temperature change rate calculation unit 45 is connected to the concentration correction unit 14. Since, besides the light guide unit 42, the simulation unit 2 to the concentration correction unit 14 are exactly the same as those of the blood sugar value measurement apparatus 201 of the fifth embodiment, a description thereof will be omitted.

Next, a process of measuring a blood sugar value using the blood sugar value measurement apparatus 41 will be described based on FIG. 24.

First, a user operates the blood sugar value measurement apparatus 41 by putting the blood sugar value measurement apparatus 41 to skin of, for example, his or her wrist and pressing a measurement initiation switch (not shown).

Here, the surface temperature sensor 43 measures a temperature of the vicinity of the surface of the skin 210, i.e., the dermis 230, and the internal temperature sensor 44 measures a temperature of the vicinity of the surface temperature sensor 43 (step S211).

Meanwhile, the irradiation unit 5 irradiates short pulsed light to the dermis 230 constituting the skin 210 (step S212).

Figure 22:
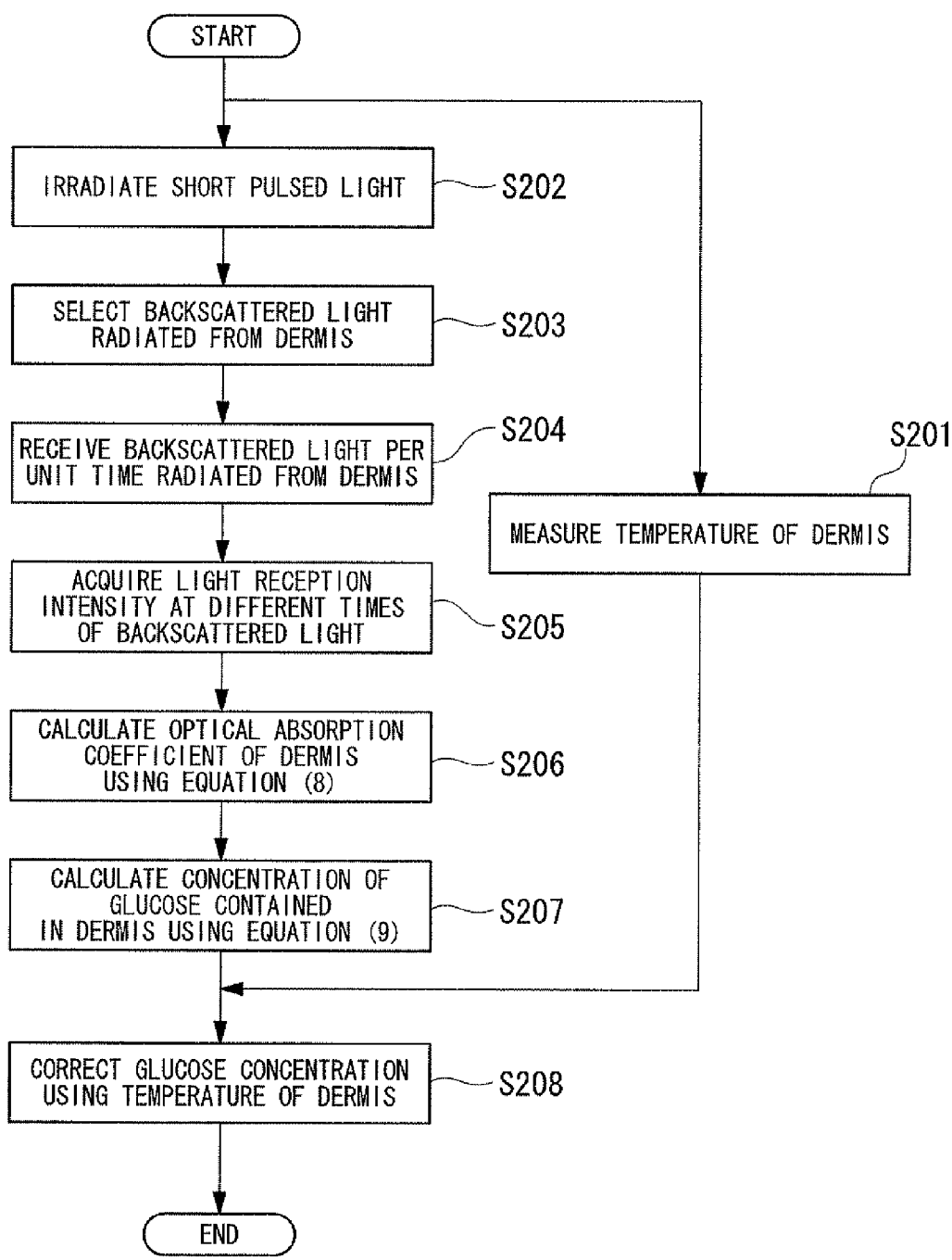
FIG. 22 is a flowchart showing a process of measuring a blood sugar value in the fifth embodiment of the present invention.

Then, processes from a process (step 5213) of selecting the backscattered light radiated by the dermis 230 from among the backscattered light radiated from the subcutaneous tissue 240, the dermis 230 and the epidermis 220 to a process (step S217) in which the concentration calculation unit 13 calculates a concentration of glucose contained in the dermis 230 are exactly the same as the process (steps S203 to S207) shown in FIG. 22 of the fifth embodiment.

The surface and internal temperature change rate calculation unit 45 then calculates a difference between the temperature of the dermis 230 measured by the surface temperature sensor 43 and the temperature of the vicinity of the surface temperature sensor 43 measured by the internal temperature sensor 44, as a temperature change rate per unit time, and judges whether the temperature change rate per unit time is within a set value (step S218).

Here, when the temperature change rate per unit time is within the set value, the temperature correction in the concentration correction unit 14, which is a next process, is performed, and when the temperature change rate per unit time exceeds the set value, this is reported using a reporting means such as sound. The temperature of the vicinity of the surface of the skin 210, i.e., the dermis 230, is measured by the surface temperature sensor 43 again and the temperature of the vicinity of the surface temperature sensor 43 is measured by the internal temperature sensor 44 again (step S211).

The concentration correction unit 14 corrects the glucose concentration of the dermis 230 calculated by the concentration calculation unit 13 using the temperature of the dermis 230 measured by the surface temperature sensor 43 using the following correction equation (step S219):

measured value of glucose concentration -value corresponding to absorption coefficient of water.

For example, when the temperature of the dermis 230 rises by T° C., a change amount of the absorption coefficient of the light is −0.004/mm×T. Accordingly, a reduction amount of the glucose concentration when the temperature of the dermis 230 rises by T° C. is 500 mg/dl×T.

As described above, according to the present embodiment, when the short pulsed light is irradiated to the skin, the temperature of the dermis 230 and the temperature of the vicinity of the surface temperature sensor 43 are measured. When a temperature change rate per unit time calculated from a difference between the temperature of the dermis 230 measured by the surface temperature sensor 43 and the temperature of the vicinity of the surface temperature sensor 43 measured by the internal temperature sensor 44 is within the set value, the glucose concentration of the dermis 230 is corrected using the temperature of the dermis 230 measured by the surface temperature sensor 43, thereby reducing effects of the temperature on the glucose concentration in the dermis. Thus, it is possible to reduce effects of the temperature of the dermis on the glucose concentration and accurately measure the glucose concentration in a non-invasive manner.

(Seventh Embodiment)

Figure 25:
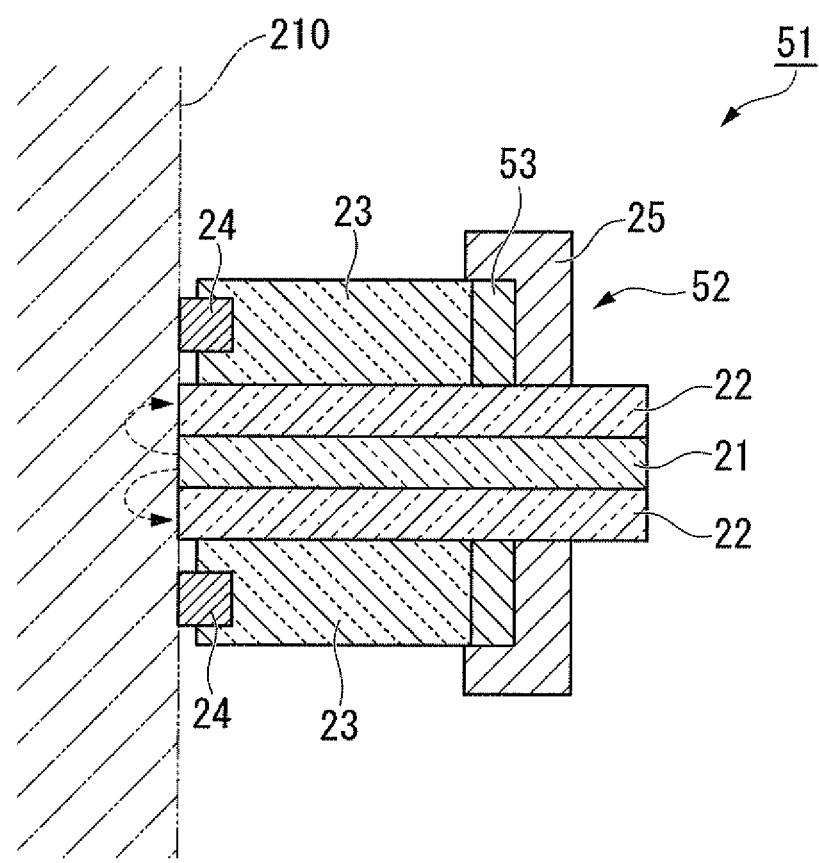
FIG. 25 is a cross-sectional view showing a configuration of a light guide unit of a blood sugar value measurement apparatus of a seventh embodiment of the present invention.

FIG. 25 is a cross-sectional view showing a schematic configuration of a light guide unit of a blood sugar value measurement apparatus (a concentration determination apparatus) of a seventh embodiment of the present invention. A difference between a light guide unit 52 of a blood sugar value measurement apparatus 51 of the present embodiment and the light guide unit 6 of the blood sugar value measurement apparatus 201 of the fifth embodiment is that an internal heat insulation unit (temperature adjustment means) 53 for adjusting and heat-insulating the vicinity of the temperature sensor 24 to a given temperature, for example, 36.0° C., using a heating means such as a heater is provided in a surface of the heat insulating material 23 opposite to the temperature sensor 24. Since, besides the light guide unit 52, the simulation unit 2 to the concentration correction unit 14 are exactly the same as those of the blood sugar value measurement apparatus 201 of the fifth embodiment, a description thereof will be omitted.

Figure 26:
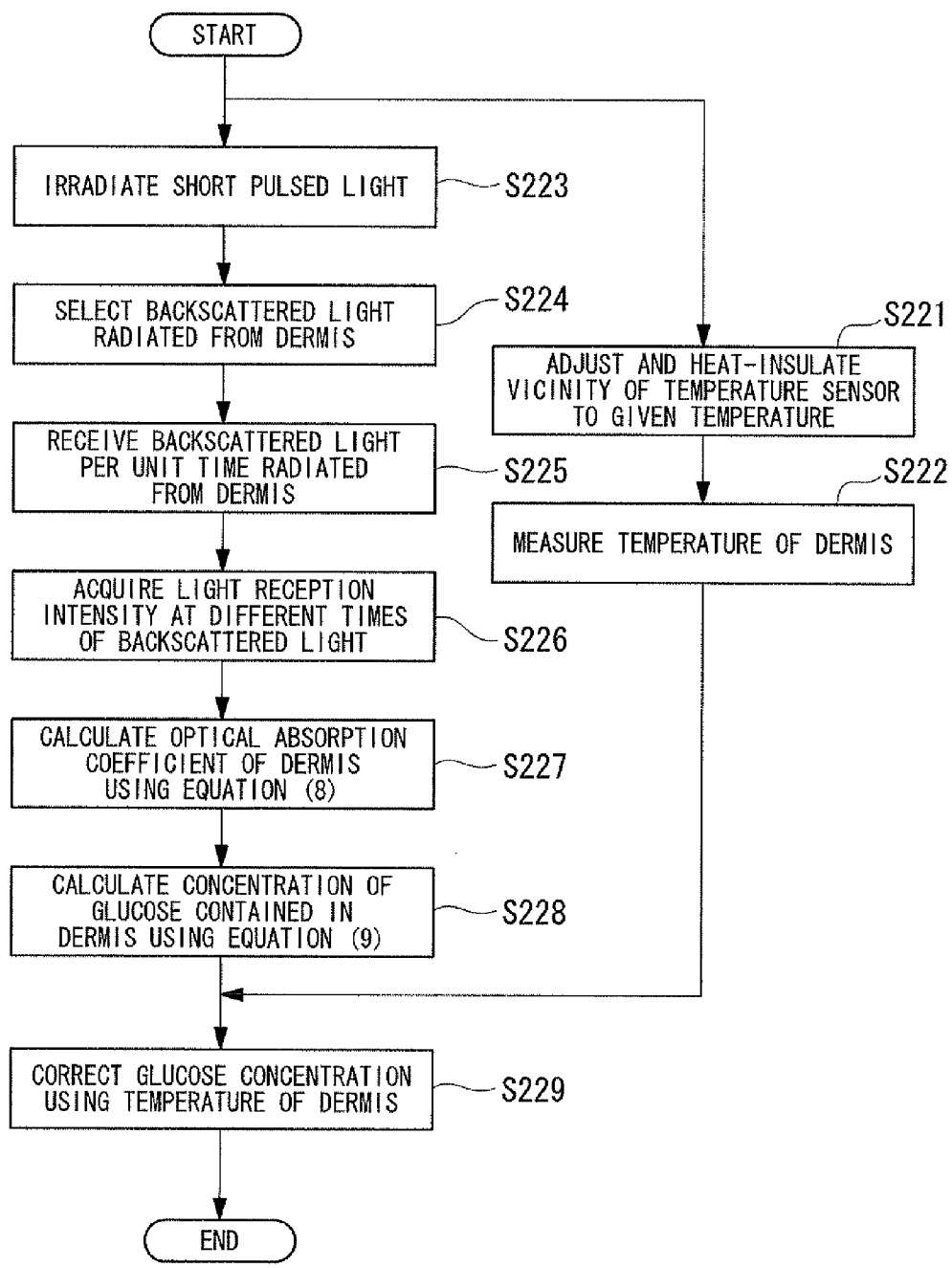
FIG. 26 is a flowchart showing a process of measuring a blood sugar value in a seventh embodiment of the present invention.

Next, a process of measuring a blood sugar value using the blood sugar value measurement apparatus 51 will be described based on FIG. 26.

First, a user operates the blood sugar value measurement apparatus 51 by putting the blood sugar value measurement apparatus 51 to skin of, for example, his or her wrist and pressing a measurement initiation switch (not shown).

Here, the internal heat insulation unit 53 adjusts and heat-insulates the vicinity of the temperature sensor 24 to a given temperature, for example, 36.0° C. (step S221).

The temperature sensor 24 then measures the temperature of the vicinity of the surface of the skin 210, i.e., the dermis 230 (step S222).

Meanwhile, the irradiation unit 5 irradiates short pulsed light to the dermis 230 constituting the skin 210 (step S223).

Then, processes from a process (step S224) of selecting the backscattered light radiated by the dermis 230 from among the backscattered light radiated from the subcutaneous tissue 240, the dermis 230 and the epidermis 220 to a process (step S229) of correcting the glucose concentration of the dermis 230 calculated by the concentration calculation unit 13 using the temperature of the de 230 measured by the temperature sensor 24 are exactly the same as the process (step S203 to S208) shown in FIG. 22 of the fifth embodiment.

The concentration correction unit 14 corrects the calculated glucose concentration of the dermis 230 based on the temperature of the dermis 230 measured by the temperature sensor 24 using the following correction equation (step S229):

measured value of glucose concentration-value corresponding to absorption coefficient of water.

For example, when the temperature of the dermis 230 rises by T° C., a change amount of the absorption coefficient of the light is −0.004/mm×T. Accordingly, a reduction amount of the glucose concentration when the temperature of the dermis 230 rises by T° C. is 500 mg/dl×T.

As described above, according to the present embodiment, since the internal heat insulation unit 53 adjusts and heat-insulates the vicinity of the temperature sensor 24 to a given temperature and then the temperature sensor 24 measures the temperature of the dermis 230, it is possible to suppress a temperature change in the temperature sensor 24 and improve measurement accuracy of the temperature sensor 24 by adjusting and heat-insulating the vicinity of the temperature sensor 24 to a given temperature.

(Eighth Embodiment)

Figure 27:
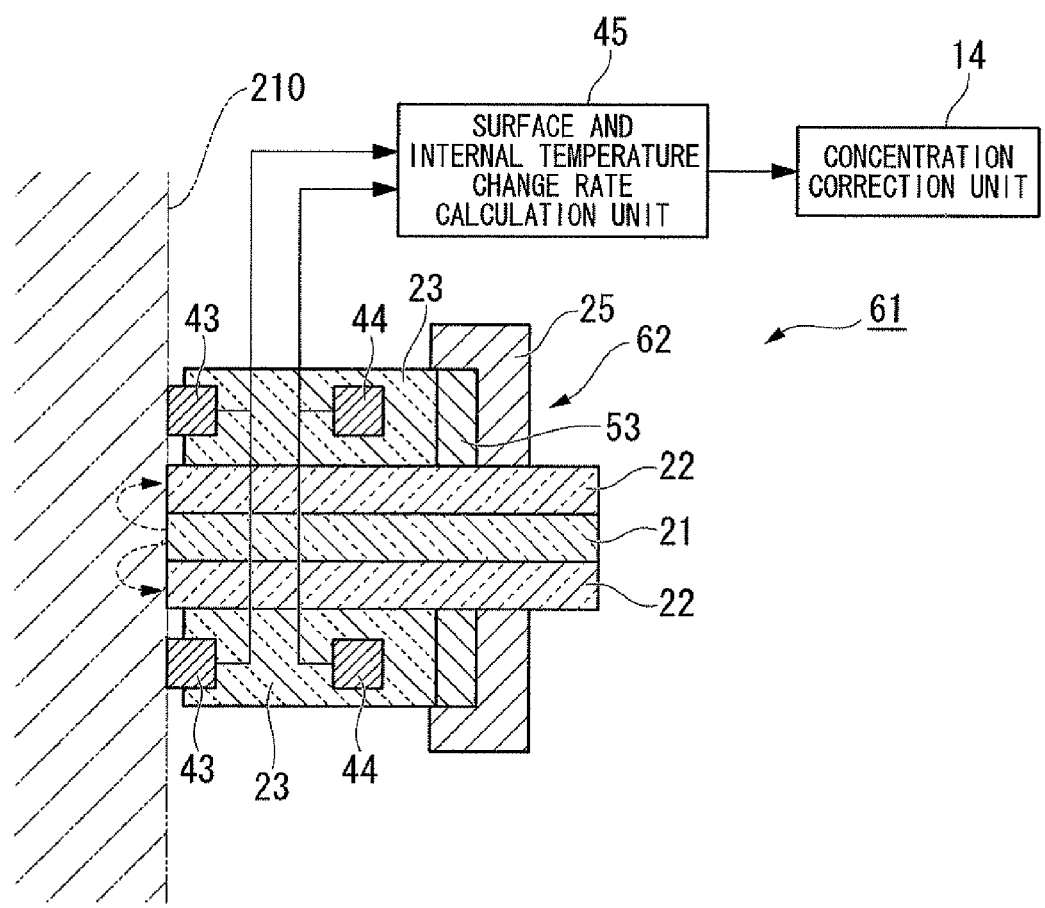
FIG. 27 is a cross-sectional view showing a configuration of a light guide unit of a blood sugar value measurement apparatus of an eighth embodiment of the present invention.

FIG. 27 is a cross-sectional view showing a schematic configuration of a light guide unit of a blood sugar value measurement apparatus (a concentration determination apparatus) of an eighth embodiment of the present invention. A difference between a light guide unit 62 of a blood sugar value measurement apparatus 61 of the present embodiment and the light guide unit 42 of the blood sugar value measurement apparatus 41 of the sixth embodiment is that an internal heat insulation unit (a temperature adjustment means) 53 of the third embodiment is provided in a surface of the heat insulating material 23 opposite to the surface temperature sensor 43. Since, besides the light guide unit 62, the simulation unit 2 to the concentration correction unit 14 are exactly the same as those of the blood sugar value measurement apparatuses 201 and 41 of the fifth and sixth embodiments, a description thereof will be omitted.

A deep-portion thermometer using a heat flow compensation method is configured of the surface temperature sensor 43, the internal temperature sensor 44, and the internal heat insulation unit 53. In the deep-portion thermometer, when sufficient time lapses, tissues of the epidermis 220 and the dermis 230 reach thermal equilibrium and the temperature of the epidermis 220 is coincident with the temperature of the dermis 230. Accordingly, it is possible to measure the temperature of the dermis 230.

Figure 28:
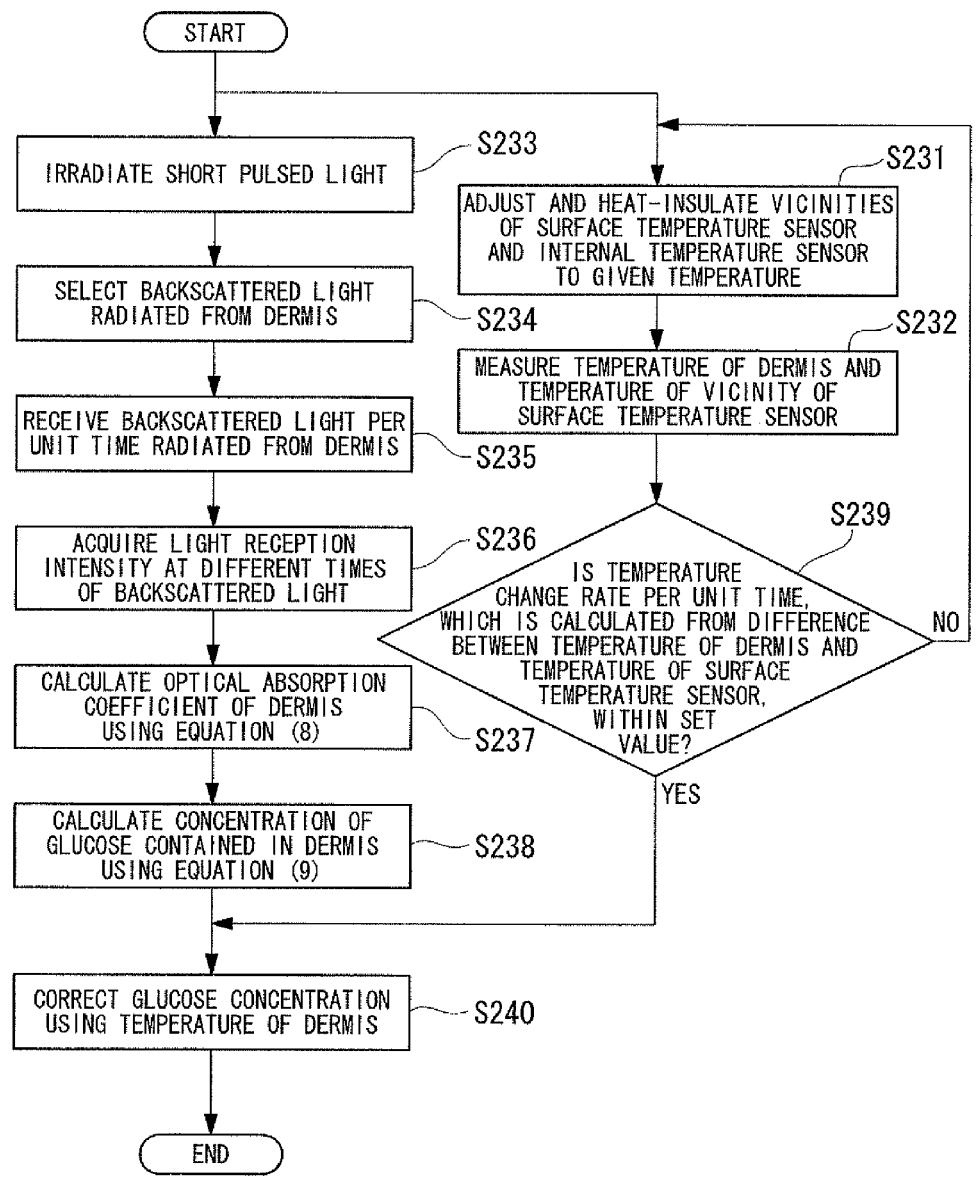
FIG. 28 is a flowchart showing a process of measuring a blood sugar value in the eighth embodiment of the present invention.

Next, a process of measuring a blood sugar value using the blood sugar value measurement apparatus 61 will be described based on FIG. 28.

First, a user operates the blood sugar value measurement apparatus 61 by putting the blood sugar value measurement apparatus 61 to skin of, for example, his or her wrist and pressing a measurement initiation switch (not shown).

Here, the internal heat insulation unit 53 adjusts and heat-insulates the vicinity of the surface temperature sensor 43 and the internal temperature sensor 44 to a given temperature, for example, 36.0° C. (step S231).

The surface temperature sensor 43 then measures the temperature of the vicinity of the surface of the skin 210, i.e., the dermis 230, and the internal temperature sensor 44 measures the temperature of the vicinity of the surface temperature sensor 43 (step S232).

Meanwhile, the irradiation unit 5 irradiates short pulsed light to the dermis 230 constituting the skin 210 (step S233).

Figure 24:
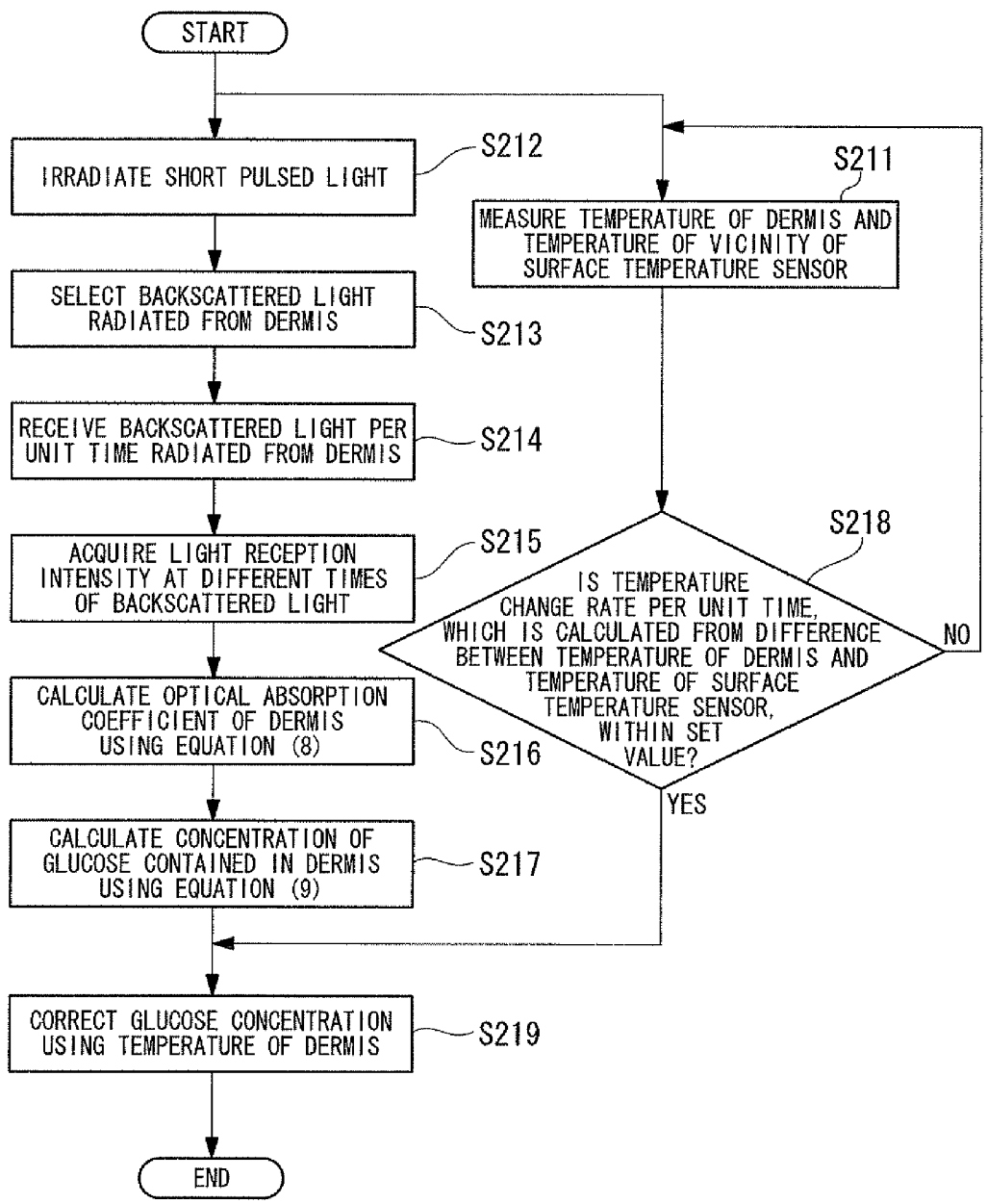
FIG. 24 is a flowchart showing a process of measuring a blood sugar value in the sixth embodiment of the present invention.

Then, processes from a process (step S234) of selecting the backscattered light radiated by the dermis 230 from among the backscattered light radiated from the subcutaneous tissue 240, the dermis 230 and the epidermis 220 to a process (step S238) in which the concentration calculation unit 13 calculates the concentration of the glucose contained in the dermis 230 are exactly the same as the process (step S213 to S217) shown in FIG. 24 of the sixth embodiment.

The surface and internal temperature change rate calculation unit 45 then calculates a difference between the temperature of the dermis 230 measured by the surface temperature sensor 43 and the temperature of the vicinity of the surface temperature sensor 43 measured by the internal temperature sensor 44, as a temperature change rate per unit time, and judges whether the temperature change rate per unit time is within a set value (step S239).

Here, when the temperature change rate per unit time is within the set value, the temperature correction in the concentration correction unit 14, which is a next process, is performed. When the temperature change rate exceeds the set value, this is reported using a reporting means such as sound, and the temperature of the vicinity of the surface of the skin 210, i.e., the dermis 230, is measured by the surface temperature sensor 43 and the temperature of the vicinity of the surface temperature sensor 43 is measured by the internal temperature sensor 44 (step S232).

The concentration correction unit 14 corrects the glucose concentration of the dermis 230 calculated by the concentration calculation unit 13, using the temperature of the dermis 230 measured by the surface temperature sensor 43, from the following correction equation (step S240):

measured value of glucose concentration-value corresponding to absorption coefficient of water.

For example, when the temperature of the dermis 230 rises by T° C., a change amount of the absorption coefficient of the light is −0.004/mm×T. Accordingly, a reduction amount of the glucose concentration when the temperature of the dermis 230 rises by T ° C is 500 mg/dl×T.

As described above, according to the present embodiment, when the short pulsed light is irradiated to the skin, the vicinities of the surface temperature sensor 43 and the internal temperature sensor 44 are adjusted and heat-insulated to a given temperature by the internal heat insulation unit 53, and then the temperature of the dermis 230 and the temperature of the vicinity of the surface temperature sensor 43 are measured. When a temperature change rate per unit time calculated from a difference between the temperature of the dermis 230 measured by the surface temperature sensor 43 and the temperature of the vicinity of the surface temperature sensor 43 measured by the internal temperature sensor 44 is within the set value, the glucose concentration of the dermis 230 is corrected using the temperature of the dermis 230 measured by the surface temperature sensor 43. Accordingly, it is possible to suppress a temperature change in the temperature sensor 24 and reduce effects of the temperature on the glucose concentration in the dermis. Thus, it is possible to reduce the effects of the temperature of the dermis on the glucose concentration and accurately measure the glucose concentration in a non-invasive manner.

(Ninth Embodiment)

Figure 29:
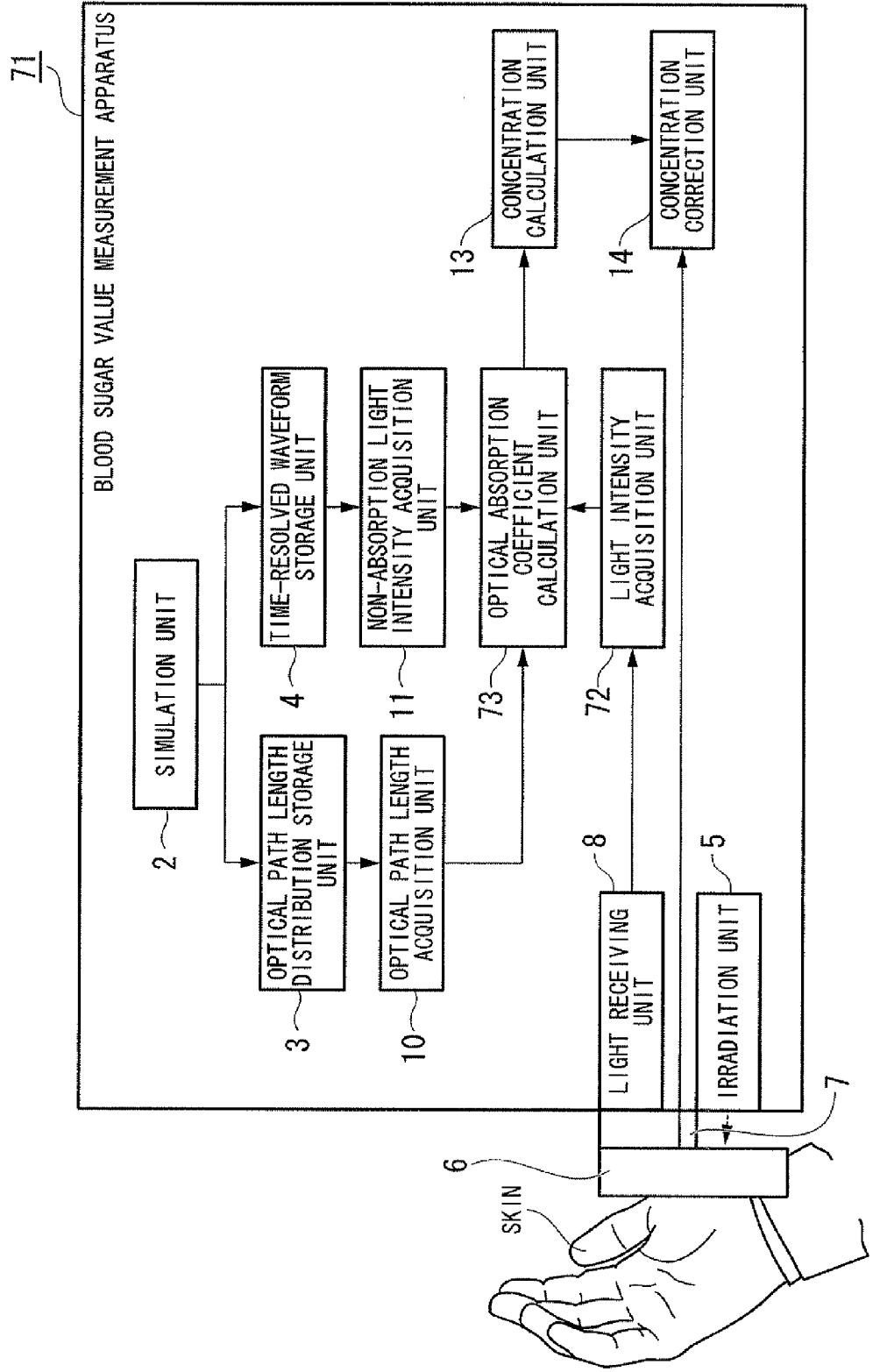
FIG. 29 is a schematic block diagram showing a configuration of a blood sugar value measurement apparatus of a ninth embodiment of the present invention.

FIG. 29 is a schematic block diagram showing a configuration of a blood sugar value measurement apparatus (a concentration determination apparatus) of a ninth embodiment of the present invention. A difference between a blood sugar value measurement apparatus 71 of the present embodiment and the blood sugar value measurement apparatus 201 of the fifth embodiment is that the light intensity acquisition unit 9 and the optical absorption coefficient calculation unit 12 are substituted with a light intensity acquisition unit (a light intensity acquisition unit) 72 and an optical absorption coefficient calculation unit (an optical absorption coefficient calculation unit) 73 having different functions from those of the light intensity acquisition unit 9 and the optical absorption coefficient calculation unit 12.

The light intensity acquisition unit 72 acquires light intensity of the backscattered light between a given time and at least a given time τ, radiated from the dermis, which has been received by the light receiving unit 8.

The optical absorption coefficient calculation unit 73 calculates the optical absorption coefficient in the dermis of the skin to which the short pulsed light having a specific wavelength $\lambda_k$ has been irradiated.

The optical absorption coefficient calculation unit 73 calculates an optical absorption coefficient of any layer in the skin using Equation (18).

Figure 30:
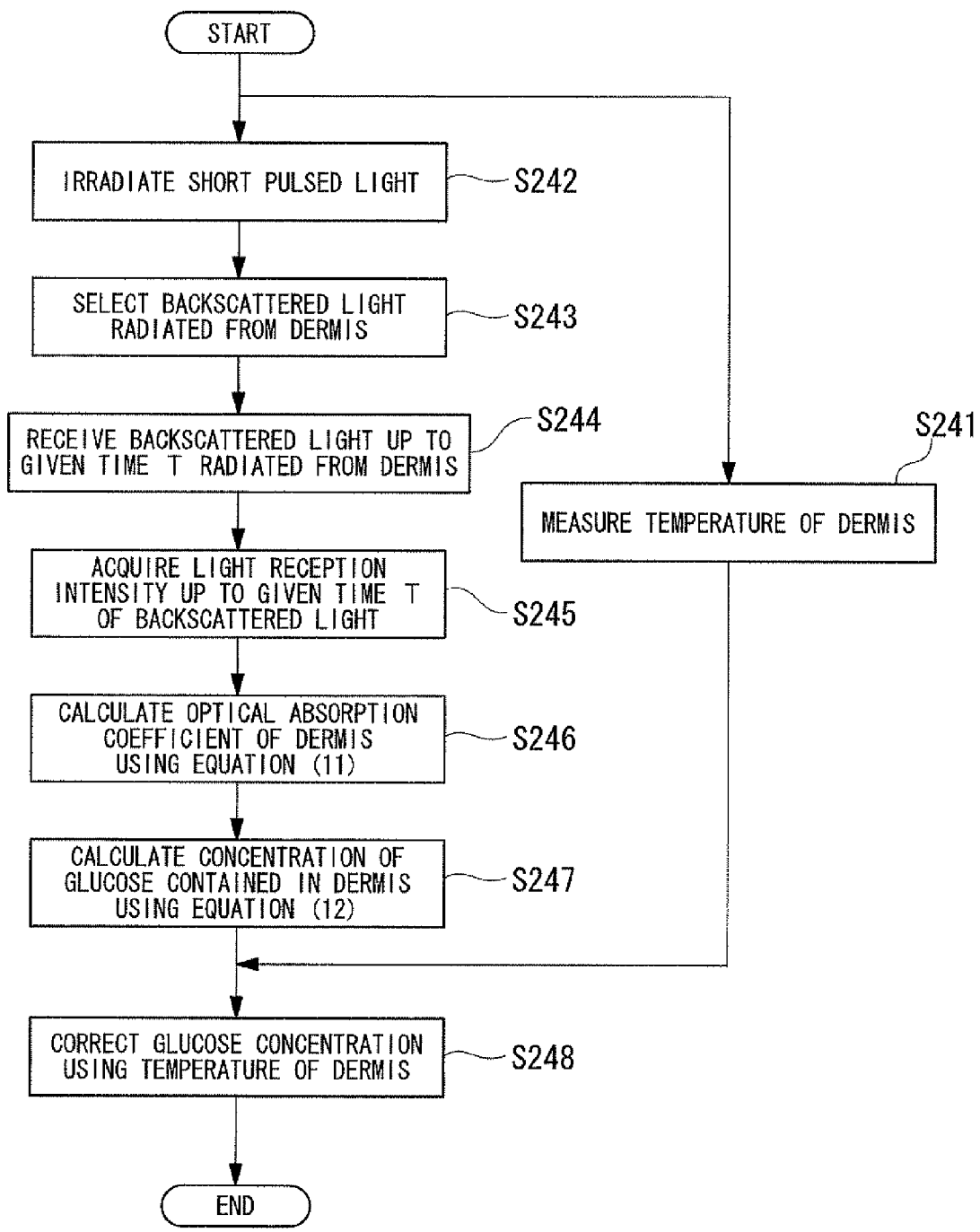
FIG. 30 is a flowchart showing a process of measuring a blood sugar value in the ninth embodiment of the present invention.

Next, a process of measuring a blood sugar value using the blood sugar value measurement apparatus 71 will be described based on FIG. 30.

In this process, since processes up to a process (step S243) in which the light scattering medium layer selection unit 7 selects the backscattered light radiated by the dermis 230 from among the backscattered light radiated from the subcutaneous tissue 240, the dermis 230 and the epidermis 220 is the same as the process shown in FIG. 22, a description thereof will be omitted.

After the backscattered light is selected, the light receiving unit 8 receives the backscattered light radiated from the dermis 230 up to a given time τ (step S244). In this case, the light receiving unit 8 records light reception intensity from irradiation initiation to at least the given time τ in an internal memory.

Then, when the light intensity acquisition unit 72 is notified that the light receiving unit 8 has completed light reception, the light intensity acquisition unit 72 acquires light reception intensity between irradiation initiation and at least given time τ, of the backscattered light radiated from the dermis 230 (step S245).

The optical absorption coefficient calculation unit 73 then calculates the optical absorption coefficient of the dermis 230 based on the light reception intensity between the irradiation initiation and at least given time τ, of the backscattered light radiated from the dermis 230, which has been acquired by the light intensity acquisition unit 72, using Equation (19) (step S246).

The concentration calculation unit 13 then calculates the concentration of the glucose contained in the dermis 230 based on the optical absorption coefficient μ of the dermis 230 calculated by the optical absorption coefficient calculation unit 73, using Equation (20) (step S247).

The concentration correction unit 14 then corrects the glucose concentration of the dermis is 230 calculated by the concentration calculation unit 13, based on the temperature of the dermis 230 measured by the temperature sensor 24, using the following correction equation (step S248):

measured value of glucose concentration-value corresponding to absorption coefficient of water.

For example, when the temperature of the dermis 230 rises by T° C., a change amount of the absorption coefficient of the light is −0.004/mm×T. Accordingly, a reduction amount of the glucose concentration when the temperature of the dermis 230 rises by T° C. is 500 mg/dl×T.

Even in the present embodiment, it is possible to suppress a temperature change in the temperature sensor 24 and reduce effects of the temperature on the glucose concentration in the dermis, similar to the fifth embodiment. Thus, it is possible to reduce the effects of the temperature of the dermis on the glucose concentration and accurately measure the glucose concentration in a non-invasive manner.

Further, in each embodiment, the case in which the concentration of the glucose contained in the dermis of the skin is measured and the blood sugar value measurement apparatus is used as a concentration determination apparatus, the skin of a person's palm is used as an observed object, the glucose is used as a target component, and the short pulsed light having a specific wavelength is used as light having a specific wavelength has been described, but the present invention is not limited thereto and the concentration determination method may be used for another apparatus for determining a concentration of a target component in any layer of an observed object formed of a plurality of light scattering medium layers.

Further, in each embodiment, the case in which the short pulsed light having the specific wavelength is used has been described, but continuous light having a specific wavelength may be used in place of the short pulsed light having the specific wavelength.

In this case, the simulation unit 2, the optical path length distribution storage unit 3, the time-resolved waveform storage unit 4, the optical path length acquisition unit 10 and the non-absorption light intensity acquisition unit 11 are unnecessary, and the temperature correction is possible.

Further, when the concentration determination apparatus of each embodiment is applied to, for example, a portable apparatus for measuring a concentration of a main component of skin, the apparatus can be effectively used for inspection, diagnosis or treatment of skin disease.

(Tenth Embodiment)

Figure 31:
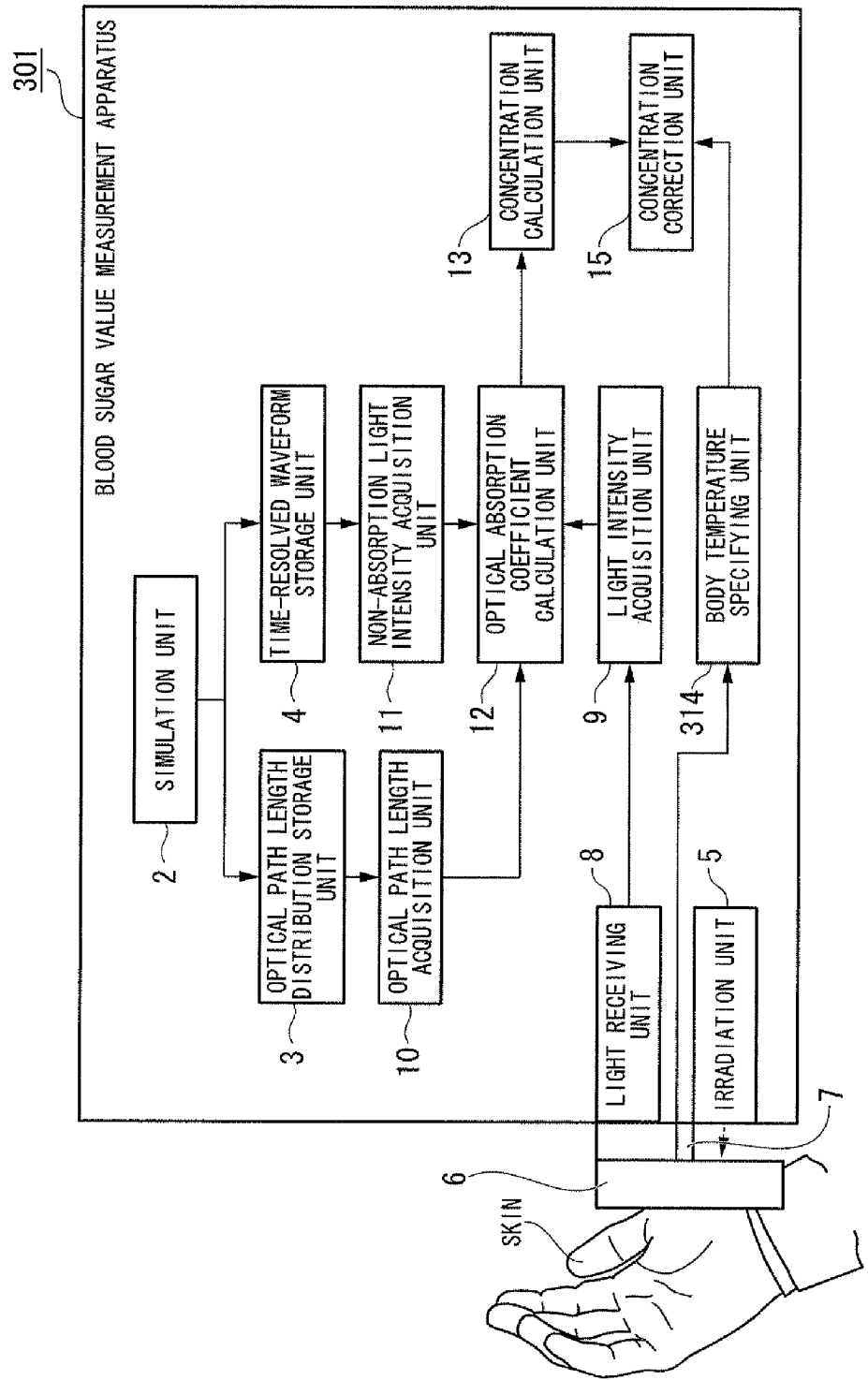
FIG. 31 is a schematic block diagram showing a configuration of a blood sugar value measurement apparatus of a tenth embodiment of the present invention.

FIG. 31 is a schematic block diagram showing a configuration of a blood sugar value measurement apparatus of a tenth embodiment of the present invention. FIG. 21 is a cross-sectional view showing a schematic configuration of a light guide unit of the blood sugar value measurement apparatus.

A blood sugar value measurement apparatus 301 noninvasively determines a concentration of glucose (a target component) included in a dermis (any layer) among a plurality of layers constituting skin (an observed object) of, for example, a palm of a human body (a living body). The blood sugar value measurement apparatus 301 includes a simulation unit 2, an optical path length distribution storage unit 3, a time-resolved waveform storage unit 4, an irradiation unit 5, a light guide unit 6, a light scattering medium layer selection unit 7, a light receiving unit 8, a light intensity acquisition unit 9, an optical path length acquisition unit 10, a non-absorption light intensity acquisition unit (light intensity model acquisition unit) 11, an optical absorption coefficient calculation unit 12, a concentration calculation unit 13, a body temperature specifying unit 314, and a concentration correction unit 15.

The simulation unit 2 performs simulation for irradiating light to a skin model having an optical absorption coefficient of 0.

The optical path length distribution storage unit 3 stores a model of an optical propagation path length distribution in each layer constituting the skin, of short pulsed light irradiated to the skin. Here, the optical path length distribution storage unit 3 stores the optical propagation path length distribution of the skin model having the optical absorption coefficient of 0.

The time-resolved waveform storage unit 4 stores a model of a time-resolved waveform of the short pulsed light irradiated to the skin. Here, the time-resolved waveform storage unit 4 stores the time-resolved waveform of the skin model having the optical absorption coefficient of 0.

The irradiation unit 5 irradiates the short pulsed light to the skin. Here, the short pulsed light refers to pulsed light having a pulse width of about 100 psec or less. Alternatively, pulsed light having a pulse width in a range of 0.1 psec to a few psec may be used as the short pulsed light.

As shown in FIG. 21, the light guide unit 6 includes an irradiation guide path 21 adhered to the skin 210 for guiding the short pulsed light generated from the irradiation unit 5 to the skin 210, a light reception guide path 22 provided integrally outside the irradiation guide path 21 for focusing the plural types of backscattered light radiated from the skin 210 and guiding the light to the light scattering medium layer selection unit 7, a heat insulating material 23 provided outside the irradiation guide path 21 and the light reception guide path 22, which are integrally formed, a pulse wave sensor (pulse wave detection unit) 24 provided in a surface, at a skin side, of the heat insulating material 23 for detecting, over a given area, pulse pressure of the vicinity of a portion having a beat in the living body, a temperature sensor (temperature measurement unit) 25 provided near the pulse wave sensor 24 for measuring a temperature over a given area, and a base 26 for fixing the irradiation guide path 21, the light reception guide path 22 and the heat insulating material 23.

A probe of the present invention is configured of the light guide unit 6, the irradiation unit 5, and the light receiving unit 8.

The irradiation guide path 21 and the light reception guide path 22 may be formed of a material having small absorption loss of the guided short pulsed light. For example, quartz glass or plastic such as polymethylmethacrylate (PMMA) or polyethylene is suitably used.

The heat insulating material 23 may be a heat insulation material with sufficiently small heat capacity in a range not affecting a temperature change of the skin 210. It is preferable that an interval between the heat insulating material 23 and the skin 210 have such a size that the heat insulating material 23 does not directly receive the temperature change of the skin 210. The interval is preferably 0.5 mm to 1.0 mm. In the heat insulating material 23, the heat capacity is sufficiently small that it does not affect the temperature change of the skin 210, such that a thermal response time until reaching 90% of a temperature arrival value can be suppressed within 0.2 seconds.

The pulse wave sensor 24 detects pulse pressure of the vicinity of a portion having a beat in the living body, i.e., pulse pressure of an artery such as a radial artery over the surface of the skin 210 including the artery (a given area), in a non-contact manner.

This pulse wave sensor 24 converts a detected analog signal into a digital signal using an A/D conversion unit, performs a fast Fourier transform (FFT) process on a pulse wave signal converted into the digital signal using an FFT processing unit, obtains a beat number from the pulse wave signal subjected to the FFT process using a beat number calculation unit, and outputs the beat number as a signal.

Further, when the beat number is obtained from the pulse wave signal, a peak interval of a waveform of the received pulse wave signal may be obtained and a reciprocal number thereof may be calculated as the beat number.

Further, a heart rate, i.e., the number of heart beats per unit time, is originally necessary, but a pulse rate may also be obtained since the heart rate is equal to the pulse rate. Accordingly, an electrocardiogram may be detected to directly obtain the heart rate.

The pulse rate and the heart rate should be distinguished in terms of medicine, but the pulse rate and the heart rate need not be distinguished in the present invention. Accordingly, the pulse rate and the heart rate are referred to as "beat number."

Since surroundings of the pulse wave sensor 24 are covered with the heat insulating material 23, the pulse wave sensor 24 is not affected by the temperature of the irradiation guide path 21 and the light reception guide path 22.

A beat judgment means for judging whether a pulse pressure is being detected may be provided in the pulse wave sensor 24, as necessary.

The temperature sensor 25 measures temperature over the surface (a given area) of the skin 210 including the artery in a non-contact manner.

The temperature sensor 25 converts a detected analog signal into a digital signal using an A/D conversion unit and outputs the digital signal.

Since the surroundings of the temperature sensor 25 are covered with the heat insulating material 23, the temperature sensor 25 can measure the temperature of the skin 210 without being affected by the temperature of the irradiation guide path 21 and the light reception guide path 22.

In the light guide unit 6, when the irradiation guide path 21 guides the short pulsed light irradiated by the irradiation unit 5 and irradiates the light to the skin 210, plural types of backscattered light are radiated from the skin 210 as the short pulsed light is irradiated to the skin 210. The plural types of backscattered light are guided to the light scattering medium layer selection unit 7 by the light reception guide path 22.

The light scattering medium layer selection unit 7 selects the backscattered light mainly radiated by the dermis from the plural types of backscattered light radiated from the skin, which have been focused and guided by the light guide unit 6.

The light receiving unit 8 receives light that is obtained as the short pulsed light is backscattered by the skin.

The light intensity acquisition unit 9 acquires light reception intensity at a plurality of different times, of the backscattered light radiated from the dermis, which has been received by the light receiving unit 8.

Here, the plurality of times preferably include a peak time of the optical propagation path length distribution of each layer constituting the skin.

Thus, the inclusion of the peak time of the optical propagation path length distribution of each layer enables any layer, for example, the dermis, to be efficiently selected from among the plurality of layers of the skin.

The optical path length acquisition unit 10 acquires an optical path length of each layer of the skin, at a given time, of the model of the optical propagation path length distribution, from the optical path length distribution storage unit 3. Here, the optical path length acquisition unit 10 acquires the optical path length at any time from the optical path length distribution storage unit 3.

The non-absorption light intensity acquisition unit 11 acquires light intensity, at a given time, of the model of the time-resolved waveform of the short pulsed light from the time-resolved waveform storage unit 4. Here, the non-absorption light intensity acquisition unit 11 acquires light intensity at any time from the time-resolved waveform storage unit 4.

The optical absorption coefficient calculation unit 12 calculates the optical absorption coefficient in the dermis of the skin to which the short pulsed light has been irradiated using Equation (4).

The concentration calculation unit 13 calculates a concentration of the glucose contained in the dermis from the optical absorption coefficient in the dermis using Equation (5).

The body temperature specifying unit 314 specifies a maximum pulse pressure among the pulse pressures based on the pulse pressure data detected over the surface of the skin 210 including the artery in a non-contact manner by the pulse wave sensor 24 and the temperature data measured over the surface of the skin 210 including the artery in a non-contact manner by the temperature sensor 25, and specifies temperature of a portion corresponding to the specified maximum pulse pressure as body temperature similar to the deep-portion temperature of the living body. This body temperature is specified per constant time and stored in a storage unit, such as a memory.

The concentration correction unit 15 corrects the glucose concentration of the dermis calculated by the concentration calculation unit 13 using the body temperature of the living body specified by the body temperature specifying unit 314.

The concentration correction unit 15 can accurately detect the glucose concentration of the dermis according to the active state of the living body by correcting the glucose concentration of the dermis calculated by the concentration calculation unit 13 using a difference between the body temperature of the living body specified by the body temperature specifying unit 314 and a reference temperature. Accordingly, it is possible to accurately measure the glucose concentration of the dermis according to the active state of the living body in a non-invasive manner and in a short time.

In the thus configured blood sugar value measurement apparatus 1, pulse pressure of the vicinity of a portion having a beat in the living body, i.e., pulse pressure of the artery, is detected in a non-contact manner by the pulse wave sensor 24 by sliding the light guide unit 6 in any direction along the skin 210 in a state in which a leading end portion of the light guide unit 6 is put to the skin 210 of the living body. In this case, the temperature of the skin 210 near the artery detected by the pulse wave sensor 24 is measured by the temperature sensor 25 in a non-contact manner.

Meanwhile, the short pulsed light radiated from the irradiation unit 5 is irradiated to the skin 210 via the irradiation guide path 21. The plural types of backscattered light are radiated from the skin 210, but are focused by the light reception guide path 22 and guided to the light scattering medium layer selection unit 7.

The light scattering medium layer selection unit 7 selects only backscattered light mainly radiated by the dermis from among the plural types of backscattered light radiated from the skin 210. The light receiving unit 8 receives only the backscattered light mainly radiated from the dermis.

Further, the light intensity acquisition unit 9 acquires light intensity of the backscattered light radiated from the dermis, which has been received by the light receiving unit 8 at time t.

Meanwhile, the optical path length acquisition unit 10 acquires the optical path length of each layer of the skin 210, at time t, of the optical propagation path length distribution in the skin model from the optical path length distribution storage unit 3, and the non-absorption light intensity acquisition unit 11 acquires light intensity, at time t, of the time-resolved waveform of the short pulsed light in the skin model from the time-resolved waveform storage unit 4.

The optical absorption coefficient calculation unit 12 then calculates the optical absorption coefficient of the dermis of the skin based on the light intensity acquired from the light intensity acquisition unit 9, the optical path length of each layer of the skin acquired by the optical path length acquisition unit 10, and the light intensity acquired by the non-absorption light intensity acquisition unit 11.

The concentration calculation unit 13 then calculates the concentration of the glucose contained in the dermis of the skin 20 based on the optical absorption coefficient calculated by the optical absorption coefficient calculation unit 12 using Equation (5).

Thus, the concentration of the glucose contained in the dermis is calculated.

Meanwhile, the body temperature specifying unit 314 specifies a maximum pulse pressure among the pulse pressures based on the pulse pressure data detected over the surface of the skin 210 including the artery in a non-contact manner by the pulse wave sensor 24 and the temperature data measured over the surface of the skin 210 including the artery in a non-contact manner by the temperature sensor 25, and specifies temperature of a portion corresponding to the specified maximum pulse pressure as body temperature similar to the deep-portion temperature of the living body.

Then, the concentration correction unit 15 corrects the glucose concentration of the dermis calculated by the concentration calculation unit 13 using the body temperature specified by the body temperature specifying unit 314.

Thus, it is possible to accurately detect the glucose concentration of the dermis according to the active state of the living body by correcting the concentration of the glucose contained in the dermis calculated based on the backscattered light radiated from the dermis, using the body temperature specified by the pulse pressure body temperature specifying unit 314, based on the pulse pressure data detected by the pulse wave sensor 24 and the temperature data of the surface of the skin 210 including the artery measured by the temperature sensor 25. Accordingly, it is possible to accurately measure the concentration of the glucose contained in the dermis in a non-invasive manner according to the active state of the living body.

Next, a body temperature measurement principle of the present embodiment will be described based on results of experiments conducted by the present inventor.

Here, a temperature distribution around a carpal artery portion was measured using a radiation thermometer having an aperture diameter of 5 mm. As a result, it was proven that temperature substantially on the carpal artery portion rises by less than 1° C. compared to the temperature of the peripheral portion, and body temperature close to normal temperature is measured.

Figure 32:
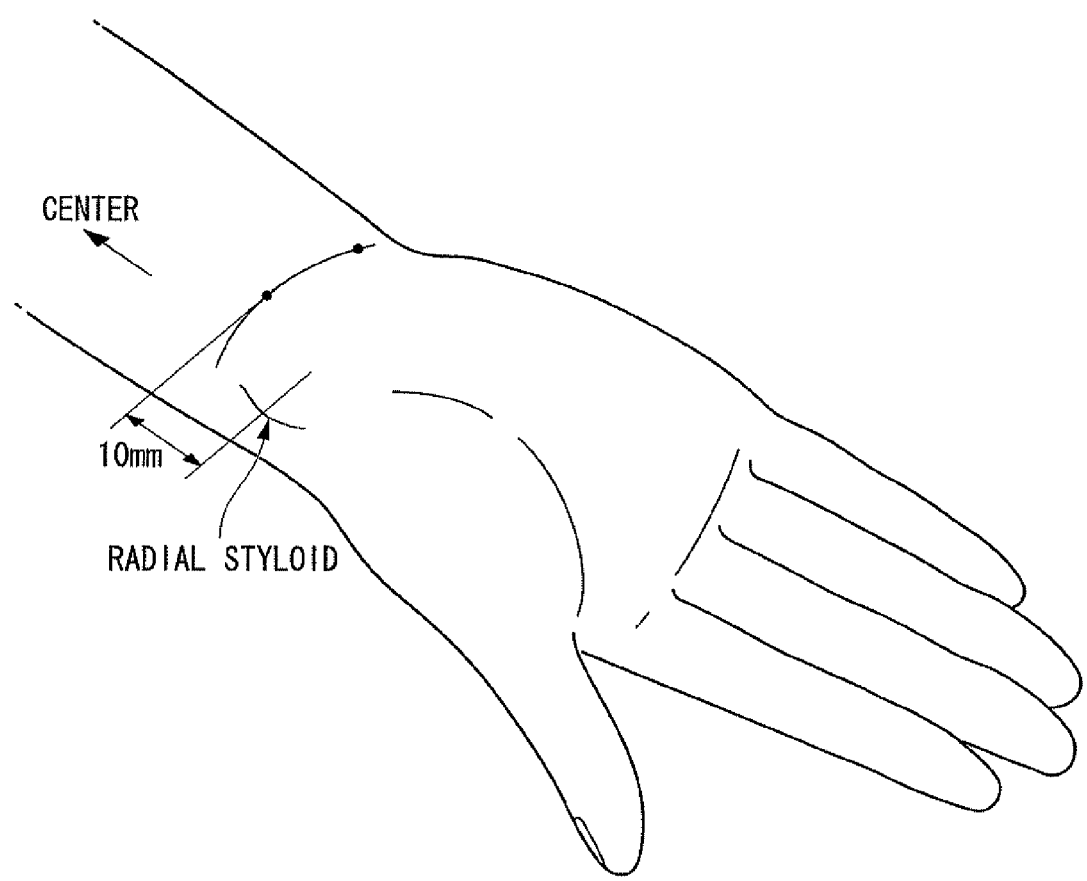
FIG. 32 is a perspective view showing an appearance near a measured part of a palm of a living body.

FIG. 32 is a perspective view showing an appearance of a measured part of the vicinity of a palm of a living body.

For measurement of the temperature, measurement points were prepared at 5 mm intervals on an imaginary line perpendicular to a radial artery/ulnar artery at a position moved by 10 mm from a radial styloid to a center, and temperature measurement at each measurement point was performed.

Figure 33A:
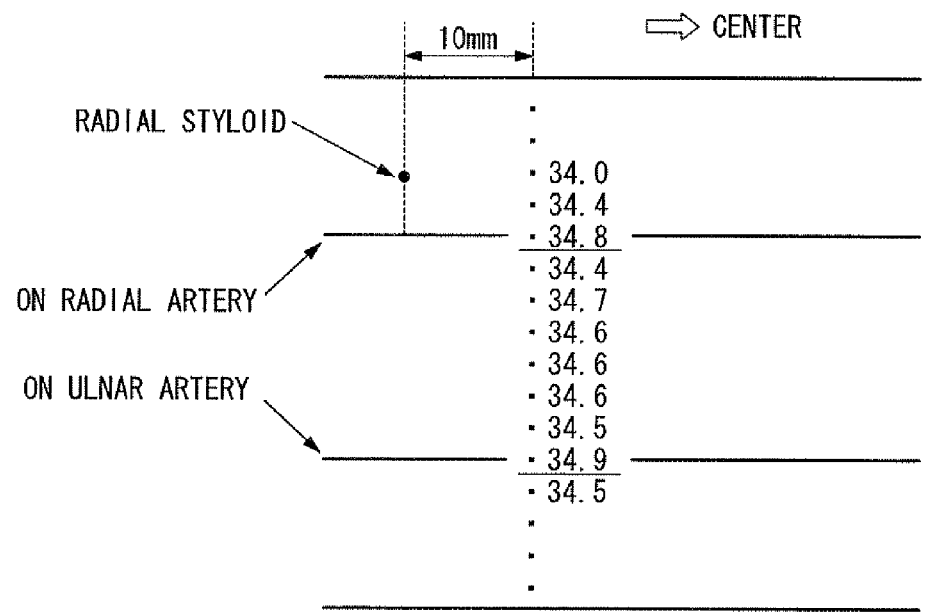
FIGS. 33A and 33B are diagrams showing a temperature measurement result near a palm of a living body each measurement point.
Figure 33B:
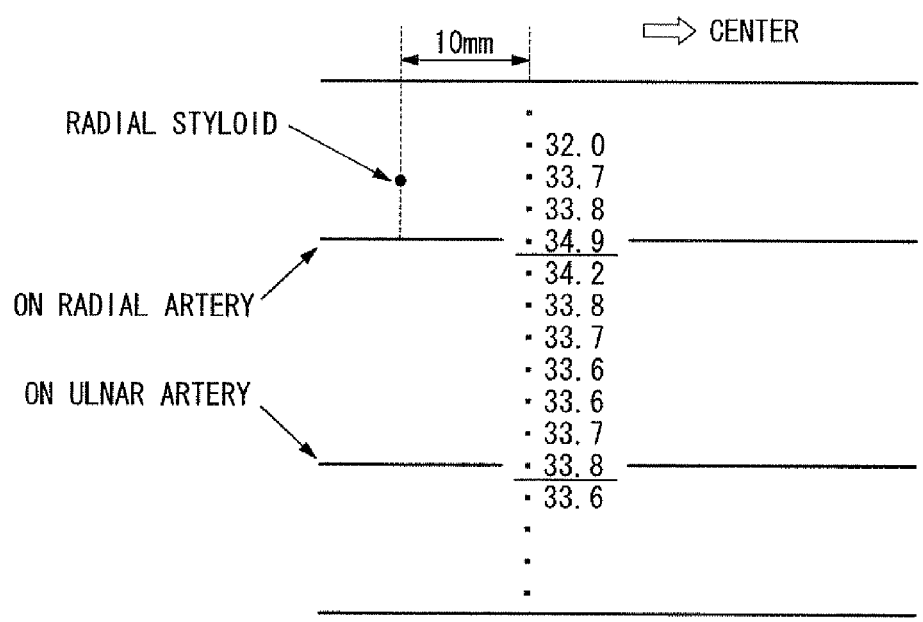

FIGS. 33A and 33B are diagrams showing the result of measuring a temperature at each measurement point near a palm of a living body. FIG. 33A shows a temperature measurement result in a dry arm. FIG. 33B shows a temperature measurement result when a measured part was soaked in water and then temperature measurement was performed.

As apparent from FIGS. 33A and 33B, either of temperature on a radial artery or temperature on an ulnar artery is higher than temperature of a peripheral portion and has a value closer to a deep-portion temperature. In addition, a difference between the temperature on the artery and the temperature of the peripheral portion is further prominent in a case in which the measured part is soaked in water than a case in which the measured part is dry. In particular, the temperature measured on the radial artery is not substantially affected by water and has substantially the same value as that when it is dry.

Reviewing the above experiment result from a medical point of view, it can be considered that since an artery such as a radial artery is a path transferring a heat source such as blood, temperature of the epidermis in such a portion on the artery is sufficiently closer to the deep-portion temperature compared to the peripheral portion. In addition, since a beat with a fast time response is observed according to blood output from a heart in the portion on the radial artery, a portion generating the beat is searched for and temperature of the portion is measured, such that a body temperature sufficiently closer to the deep-portion temperature can be obtained.

A portion from which the beat is detected may be an artery other than a microvascular artery, i.e., any portion on each of a large artery, a middle artery, and a small artery. For example, a portion of the middle artery may include the above-described radial artery, and the small artery may include a base of a finger.

Figure 34:
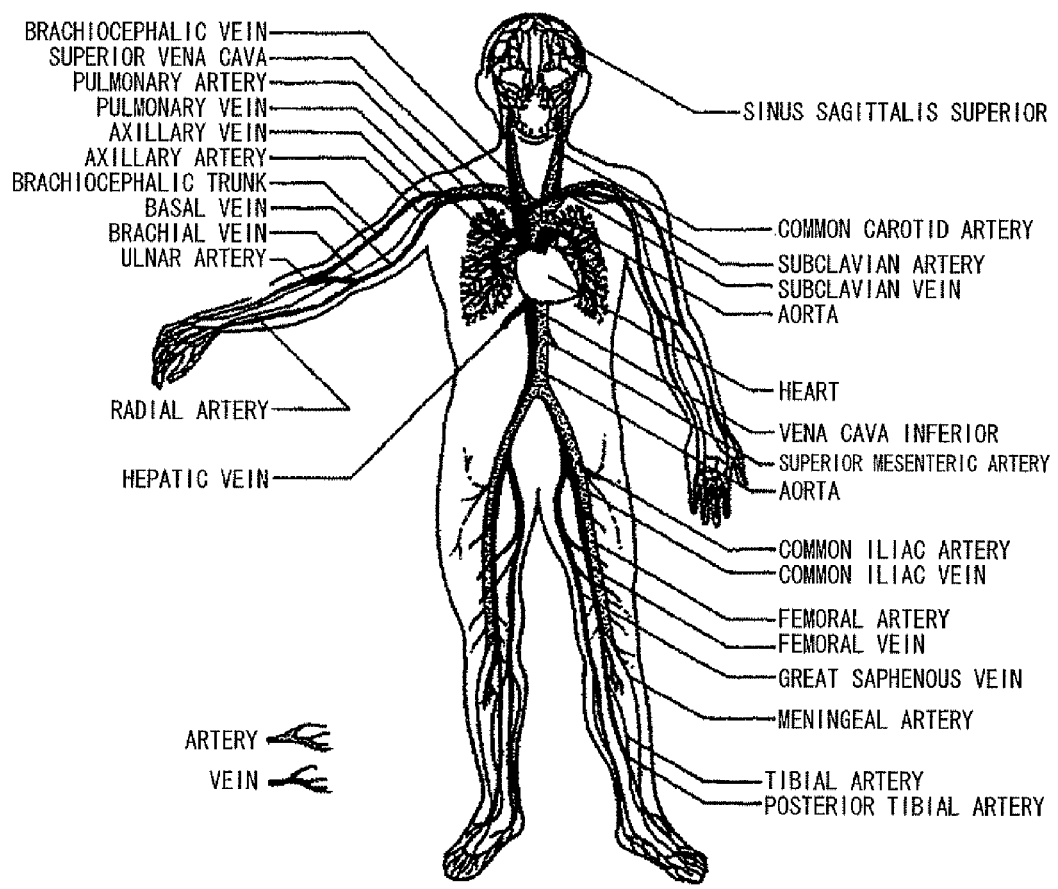
FIG. 34 is a schematic diagram showing an overall circulatory system of a living body.

FIG. 34 is a schematic diagram showing an overall circulatory system of a living body.

The overall circulatory system consists of physical blood vessels that distribute blood from a heart to each portion of a living body and return the blood from the portions of the living body. Meanwhile, a circulatory unit including microscopic vessels involved in exchange between fluid and tissue, lymphatic capillaries associated with the microscopic vessels, and interstitial tissue or parenchymal tissue surrounding lymphatic capillaries is called a micro circulatory system. In the micro circulatory system, microvascular arteries branch into network-shaped capillaries at an arterial end, which are then gathered again to form microvascular veins. The microvascular veins are connected to veins.

Thus, when the body temperature is measured at a distal portion such as a radial artery, it is expected that body temperature close to the deep-portion temperature can be accurately measured even when the distal portion is wet as it may be in ordinary life, and not in an exceptional state such as the distal portion always being exposed to water.

For example, when it is assumed that a change of body temperature of the person is desired to be monitored during sleep, body temperature measurement can be performed without problem by applying the measurement principle.

In the present embodiment, in order to measure the body temperature sufficiently close to the deep-portion temperature of the living body, the pulse wave sensor 24 and the temperature sensor 25 of the above-described light guide unit 6 are arranged on a surface on the radial artery of the living body, and temperature detected from the portion of the living body is defined as the body temperature.

Traditionally, when the deep-portion temperature is measured, temperature measurement has been performed in the rectum, tongue, side and the like using a small device such as a thermometer or table-top equipment, but in measurement at such portions, only measurement of one point at a time could be performed. Further, since the apparatus is generally large, it is difficult to always carrying the apparatus to continuously measure body temperature.

On the other hand, in the present embodiment, it is possible to relatively easily measure the body temperature sufficiently close to the deep-portion temperature of the living body. Accordingly, the body temperature sufficiently close to the deep-portion temperature measured in the present embodiment is useful for, for example, calculation of consumed calories. The body temperature is very important in view of clinical medicine.

Since the operation of the blood sugar value measurement apparatus 301 is the same as that in the first embodiment, a description thereof will be omitted.

Next, a process of measuring a blood sugar value using the blood sugar value measurement apparatus 301 will be described based on FIG. 35.

First, a user operates the blood sugar value measurement apparatus 301 by putting the blood sugar value measurement apparatus 301 to skin of, for example, his or her wrist and pressing a measurement initiation switch (not shown).

Here, pulse pressure of the vicinity of a portion having a beat in the living body, i.e., pulse pressure of the artery, is detected in a non-contact manner by the pulse wave sensor 24 by sliding the light guide unit 6 along the skin 210 in any direction in a state in which a leading end portion of the light guide unit 6 is put to the skin 210 of the living body. Simultaneously, temperature of the skin 210 near the artery detected by the pulse wave sensor 24 is measured by the temperature sensor 25 in a non-contact manner (step S301).

Then, the body temperature specifying unit 314 specifies a maximum pulse pressure among the pulse pressures based on the pulse pressure data detected over the surface of the skin 210 including the artery in a non-contact manner by the pulse wave sensor 24 and the temperature data measured over the surface of the skin 210 including the artery in a non-contact manner by the temperature sensor 25, and specifies temperature of a portion corresponding to the specified maximum pulse pressure as body temperature similar to the deep-portion temperature of the living body (step S302).

Meanwhile, the irradiation unit 5 irradiates the short pulsed light to the dermis 230 constituting the skin 210 (step S303).

The light guide unit 6 then focuses the plural types of backscattered light radiated from the skin 210, i.e., the backscattered light radiated from the subcutaneous tissue 240, the dermis 230 and the epidermis 220, and guides the light to the light scattering medium layer selection unit 7.

The light scattering medium layer selection unit 7 selects the backscattered light radiated by the dermis 230 from among the backscattered light radiated from the subcutaneous tissue 240, the dermis 230 and the epidermis 220 focused and guided by the light guide unit 6 (step S304).

Then, the light receiving unit 8 receives the backscattered light per unit time radiated from the dermis 230 (step S305). In this case, the light receiving unit 8 records light reception intensity per unit time (e.g., times $t_1$ to $t_m$ per 1 picosecond) from irradiation initiation in an internal memory.

When the light intensity acquisition unit 9 is notified that the light receiving unit 8 has completed light reception, the light intensity acquisition unit 9 acquires the light reception intensity of the backscattered light radiated from the dermis 230 at different times (step S306). That is, the light intensity acquisition unit 9 acquires the light intensity of the backscattered light at each of a plurality of times $t_1$ to $t_m$.

Here, times $t_1$ to $t_m$ when the light intensity acquisition unit 9 acquires the light intensity preferably include a time when the backscattered light radiated from the dermis 230 reaches a peak. That is, the time is preferably obtained by adding a time when an optical path length of the dermis 230 is maximized, to a time when the irradiation unit 5 has irradiated the short pulsed light.

Then, the optical absorption coefficient calculation unit 12 calculates the optical absorption coefficient of the dermis 230 based on the light reception intensity, at different times, of the backscattered light radiated from the dermis 230, which has been acquired by the light intensity acquisition unit 9, i.e., the light intensity of the backscattered light at a plurality of times $t_1$ to $t_m$, using Equation (8) (step S307).

Then, the concentration calculation unit 13 calculates the concentration of the glucose contained in the dermis 230 based on the optical absorption coefficient μ of the dermis 230 calculated by the optical absorption coefficient calculation unit 12 using Equation (9) (step S308).

Then, the concentration correction unit 14 corrects the glucose concentration of the dermis 230 calculated by the concentration calculation unit 13 based on the difference between the body temperature similar to the deep-portion temperature of the living body specified by the body temperature specifying unit 314 and a reference temperature, using the following correction equation (step S309):

measured value of glucose concentration-value corresponding to absorption coefficient of water.

For example, when the temperature of the dermis 230 rises by T° C., a change amount of the absorption coefficient of the light is −0.004/mm×T. Accordingly, a reduction amount of the glucose concentration when the temperature of the dermis 230 rises by T° C. is 500 mg/dl×T.

The above-described blood sugar value measurement apparatus 301 includes a computer system therein, and the processing operation of each step described above is stored as a program format in a computer-readable recording medium. When the program is read and executed by the computer, the processing operation may be performed.

Here, the computer-readable recording medium may include a magnetic disk, a magneto-optical disc, a CD-ROM, a DVD-ROM, a semiconductor memory, etc.

Further, the computer program is distributed to a computer by a communication line so that the program is executed by the computer.

Further, the program may realize a part of each step.

Further, the program may be a difference file (a difference program) that can realize the above-described function in combination with a program that has already been recorded in a computer system.

As described above, according to the present embodiment, the pulse pressure of the artery is detected in a non-contact manner by the pulse wave sensor 24 and simultaneously, the temperature of the skin 210 near the artery is measured in a non-contact manner by the temperature sensor 25, and the glucose concentration in the dermis of the skin calculated based on the backscattered light radiated from the dermis is corrected based on the body temperature similar to the deep-portion temperature of the living body specified by the body temperature specifying unit 314. Accordingly, it is possible to accurately detect the glucose concentration in the dermis calculated based on the backscattered light according to the active state of the living body. Thus, it is possible to accurately measure the glucose concentration in the dermis according to the active state of the living body in a non-invasive manner and in a short time.

(Eleventh Embodiment)

Figure 36:
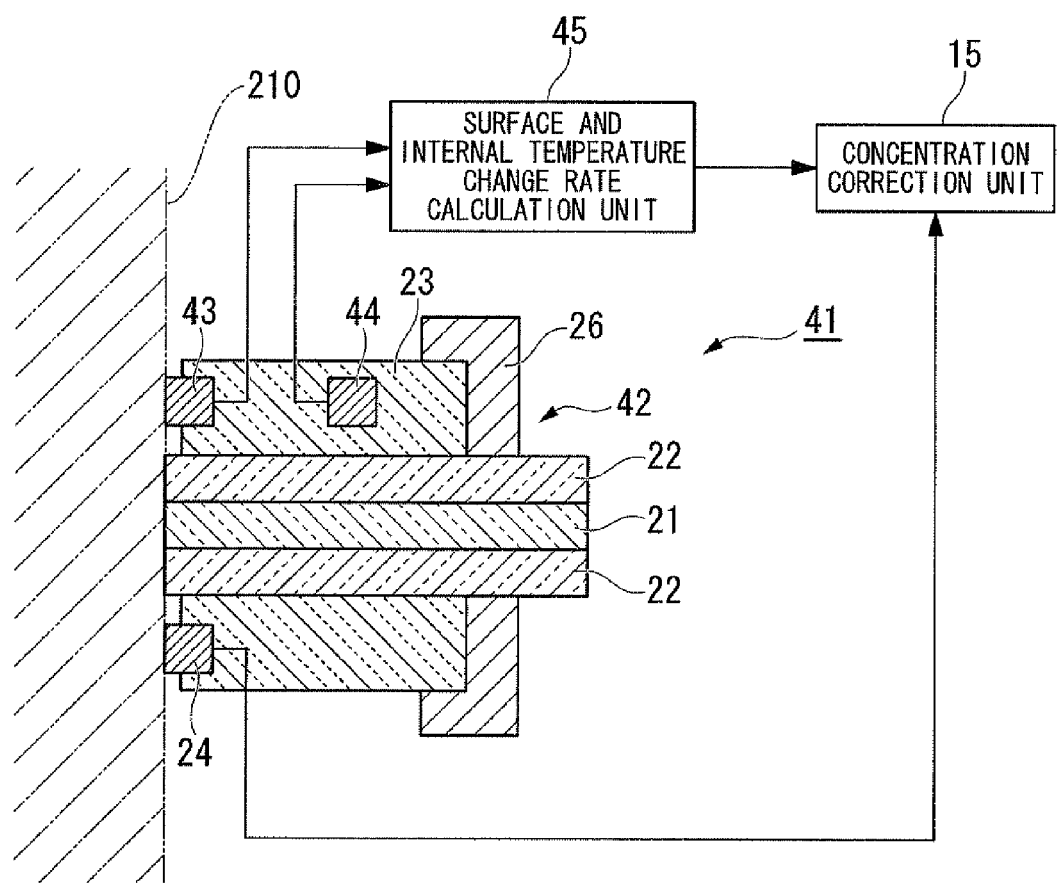
FIG. 36 is a cross-sectional view showing a configuration of a light guide unit of a blood sugar value measurement apparatus of an eleventh embodiment of the present invention.

FIG. 36 is a cross-sectional view showing a schematic configuration of a light guide unit of a blood sugar value measurement apparatus (a concentration determination apparatus) of an eleventh embodiment of the present invention. A difference between a light guide unit 42 of a blood sugar value measurement apparatus 41 of the present embodiment and the light guide unit 6 of the blood sugar value measurement apparatus 301 of the tenth embodiment is that the temperature sensor 25 is substituted with a surface temperature sensor (surface temperature measurement unit) 43 for measuring a temperature of the surface of the skin 210 and a sensor internal temperature measurement sensor (sensor internal temperature measurement unit) 44 provided in the heat insulating material 23 for directly measuring a temperature of the surface temperature sensor 43, a surface and internal temperature change rate calculation unit 45 for calculating a difference between the temperature of the dermis 230 measured by the surface temperature sensor 43 and the temperature of the vicinity of the surface temperature sensor 43 measured by the sensor internal temperature measurement sensor 44 as a temperature change rate per unit time is provided, and the pulse wave sensor 24 and the surface and internal temperature change rate calculation unit 45 are connected to the concentration correction unit 15. Since, besides the light guide unit 42, a simulation unit 2 to a concentration calculation unit 13 are exactly the same as those of the blood sugar value measurement apparatus 1 of the tenth embodiment, a description thereof will be omitted.

Next, a process of measuring a blood sugar value using the blood sugar value measurement apparatus 41 will be described based on FIG. 37.

First, a user operates the blood sugar value measurement apparatus 41 by putting the blood sugar value measurement apparatus 41 to skin of, for example, his or her wrist and pressing a measurement initiation switch (not shown).

Here, the light guide unit 42 is slid along the skin 210 in any direction in a state in which a leading end portion of the light guide unit 42 is put to the skin 210 of the living body, and pulse pressure of the vicinity of a portion having a beat in the living body, i.e., pulse pressure of the artery, is detected in a non-contact manner by the pulse wave sensor 24 (step S311).

Then, the surface temperature sensor 43 measures temperature of the surface of the skin 210, i.e., a surface temperature on the artery, and the sensor internal temperature measurement sensor 44 measures temperature of the vicinity of the surface temperature sensor 43 (step S312).

Then, the surface and internal temperature change rate calculation unit 45 calculates a difference between the surface temperature on the artery measured by the surface temperature sensor 43 and the temperature of the vicinity of the surface temperature sensor 43 measured by the sensor internal temperature measurement sensor 44, as a temperature change rate per unit time, and judges whether the temperature change rate per unit time is within a set value (step S313).

Here, when the temperature change rate per unit time is within the set value, the irradiation unit 5 irradiates short pulsed light to the dermis 230 constituting the skin 210 (step S314).

On the other hand, when a temperature change rate per unit time exceeds the set value, this is reported using a reporting means such as sound and pulse pressure of the artery is detected in a non-contact manner again (step S311).

Figure 35:
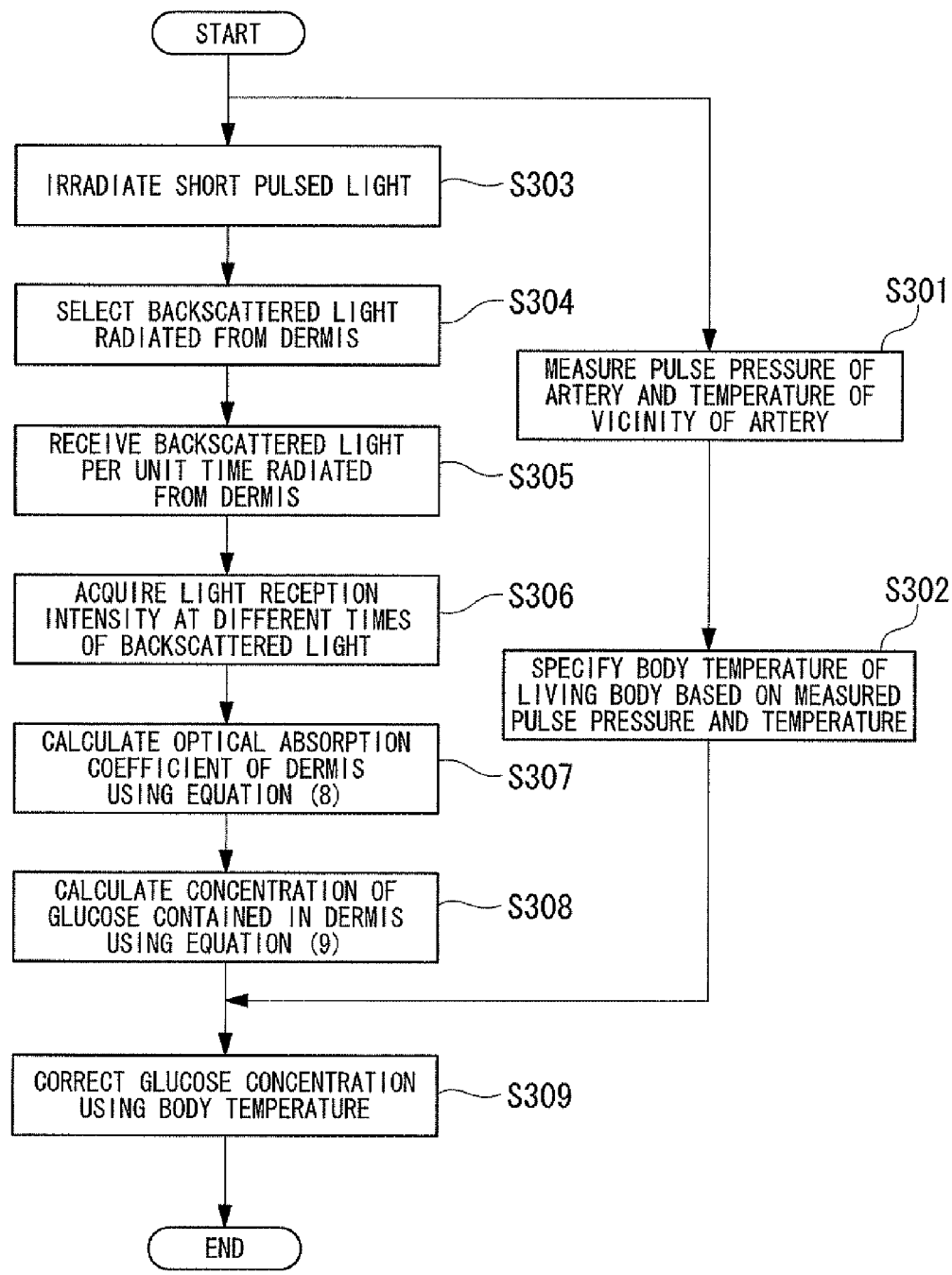
FIG. 35 is a flowchart showing a process of measuring a blood sugar value in the tenth embodiment of the present invention.

After the short pulsed light is irradiated, processes from a process (step 5315) of selecting the backscattered light radiated by the dermis 230 from among the backscattered light radiated from the subcutaneous tissue 240, the dermis 230 and the epidermis 220 to a process (step S319) in which the concentration calculation unit 13 calculates the concentration of the glucose contained in the dermis 230 are exactly the same as the process (step S304 to S308) shown in FIG. 35 of the tenth embodiment.

The concentration correction unit 15 corrects the glucose concentration of the dermis 230 calculated by the concentration calculation unit 13 using the surface temperature on the artery measured by the surface temperature sensor 43 from the following correction equation (step S320):

measured value of glucose concentration-value corresponding to absorption coefficient of water.

For example, when the temperature of the dermis 230 (=a surface temperature on the artery) rises by T° C., a change amount of the absorption coefficient of the light is −0.004/mm×T. Accordingly, a reduction amount of the glucose concentration when the temperature of the dermis 230 rises by T° C. is 500 mg/dl×T.

As described above, according to the present embodiment, the pulse pressure of the artery in the living body is detected in a non-contact manner by the pulse wave sensor 24, and the temperature on the artery and the temperature of the vicinity of the surface temperature sensor 43 are measured. When the temperature change rate per unit time calculated from the difference between the temperature on the artery measured by the surface temperature sensor 43 and the temperature of the vicinity of the surface temperature sensor 43 measured by the sensor internal temperature measurement sensor 44 is within the set value, the glucose concentration of the dermis 230 is corrected using the temperature on the artery measured by the surface temperature sensor 43, thereby accurately detecting the glucose concentration in the dermis according to the active state of the living body. Thus, it is possible to accurately measure the glucose concentration in the dermis according to the active state of the living body in a non-invasive manner and in a short time.

(Twelfth Embodiment)

A cross-sectional view showing a schematic configuration of a light guide unit of a blood sugar value measurement apparatus (a concentration determination apparatus) of a twelfth embodiment of the present invention is the same as FIG. 25. A difference between a light guide unit 52 of a blood sugar value measurement apparatus 51 of the present embodiment and the light guide unit 6 of the blood sugar value measurement apparatus 1 of the tenth embodiment is that an internal heat insulation unit (temperature adjustment means) 53 for adjusting and heat-insulating the vicinities of the pulse wave sensor 24 and the temperature sensor 25 to a given temperature, for example, 36.0° C., using a heating means such as a heater is provided in a surface of a heat insulating material 23 opposite to the pulse wave sensor 24 and the temperature sensor 25. Since, besides the light guide unit 52, a simulation unit 2 to a concentration correction unit 15 are the same as those in the blood sugar value measurement apparatus 301 of the tenth embodiment, a description thereof will be omitted.

Figure 38:
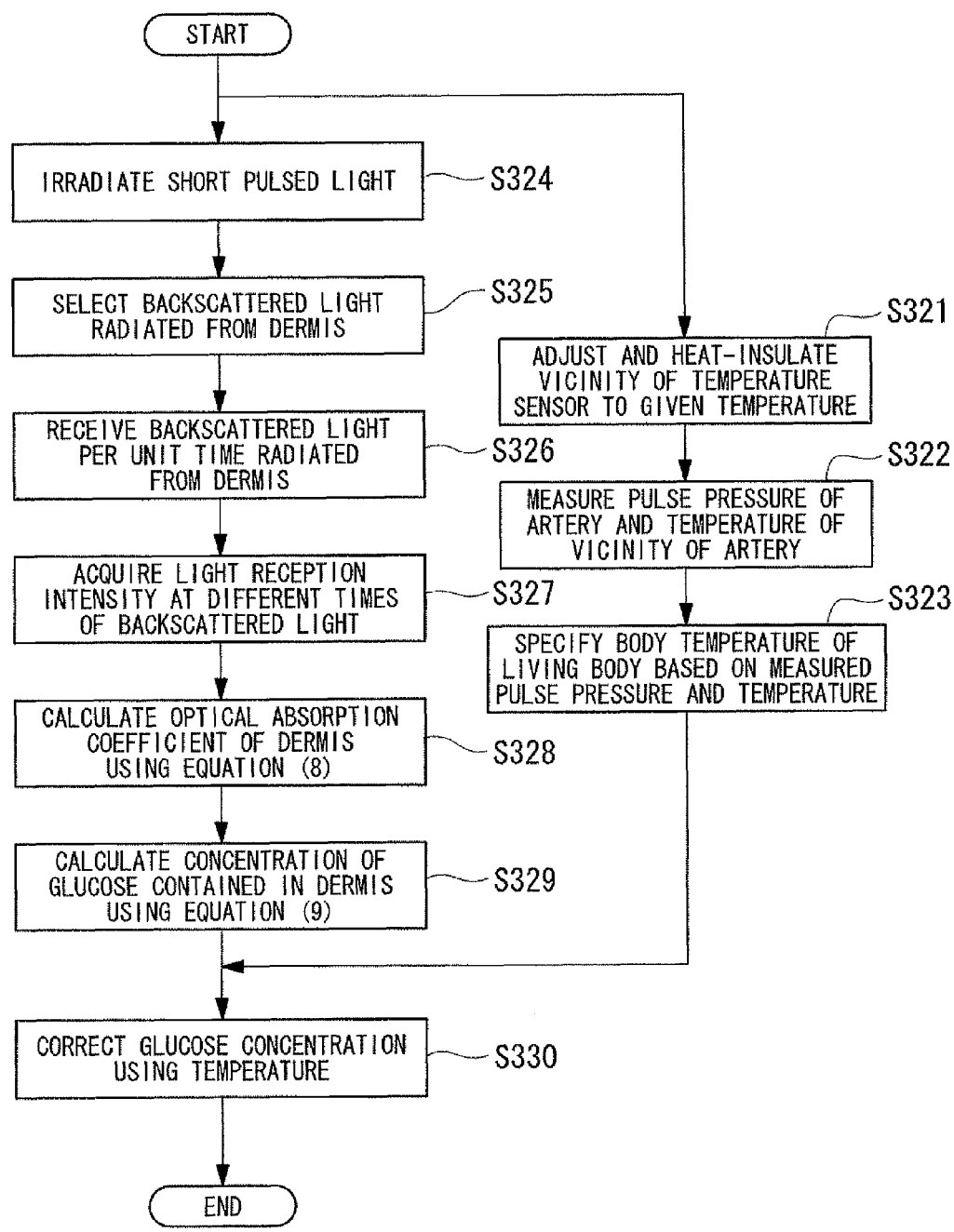
FIG. 38 is a flowchart showing a process of measuring a blood sugar value in a twelfth embodiment of the present invention.

A process of measuring a blood sugar value using the blood sugar value measurement apparatus 51 will be described based on FIG. 38.

First, a user operates the blood sugar value measurement apparatus 51 by putting the blood sugar value measurement apparatus 51 to skin of, for example, his or her wrist and pressing a measurement initiation switch (not shown).

Here, the internal heat insulation unit 53 adjusts and heat-insulates the vicinity of the temperature sensor 25 to a given temperature, for example, 36.0° C. (step S321).

Then, the light guide unit 52 is slid along the skin 210 in any direction in a state in which a leading end portion of the light guide unit 52 is put to the skin 210 of the living body, and pulse pressure of the vicinity of a portion having a beat in the living body, i.e., pulse pressure of the artery, is detected in a non-contact manner by the pulse wave sensor 24. Simultaneously, the temperature of the skin 210 on the artery detected by the pulse wave sensor 24 is measured by the temperature sensor 25 in a non-contact manner (step S322).

Then, the body temperature specifying unit 314 specifies a maximum pulse pressure from among the pulse pressures based on the pulse pressure data detected over the surface of the skin 210 including the artery in a non-contact manner by the pulse wave sensor 24 and the temperature data measured over the surface of the skin 210 including the artery in a non-contact manner by the temperature sensor 25, and specifies temperature of a portion corresponding to the specified maximum pulse pressure as body temperature similar to the deep-portion temperature of the living body (step S323).

Meanwhile, the irradiation unit 5 irradiates short pulsed light to the dermis 230 constituting the skin 210 (step S324). Then, processes from a process (step 5325) of selecting the backscattered light radiated by the dermis 230 from among the backscattered light radiated from the subcutaneous tissue 240, the dermis 230 and the epidermis 220 to a process (step S330) of correcting the glucose concentration of the dermis 230 calculated by the concentration calculation unit 13 using the temperature of the dermis 230 measured by the temperature sensor 24 are exactly the same as the process (step S303 to S309) shown in FIG. 35 of the tenth embodiment.

Even in the present embodiment, the same effects as those of the blood sugar value measurement apparatus 301 of the tenth embodiment can be achieved.

In addition, the vicinities of the pulse wave sensor 24 and the temperature sensor 25 are adjusted and heat-insulated to a given temperature by the internal heat insulation unit 53, the pulse pressure of the artery is detected in a non-contact manner by the pulse wave sensor 24, the temperature of the skin 210 near the artery is measured in a non-contact manner by the temperature sensor 25, and the glucose concentration in the dermis of the skin calculated based on the backscattered light radiated from the dermis is corrected based on the body temperature similar to the deep-portion temperature of the living body specified by the body temperature specifying unit 314, thereby suppressing a temperature change in the pulse wave sensor 24 and the temperature sensor 25 and improving measurement accuracy of the pulse wave sensor 24 and the temperature sensor 25 by adjusting and heat-insulating the vicinities of the pulse wave sensor 24 and the temperature sensor 25 to a given temperature.

(Thirteenth Embodiment)

Figure 39:
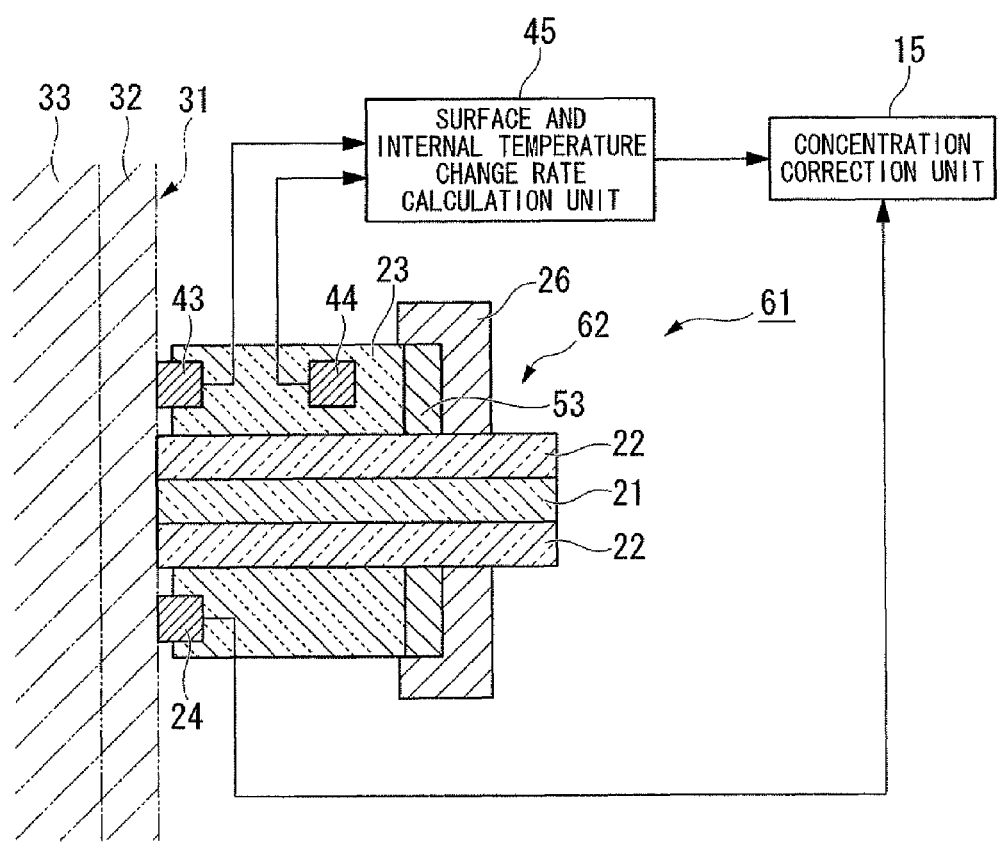
FIG. 39 is a cross-sectional view showing a configuration of a light guide unit of a blood sugar value measurement apparatus of a thirteenth embodiment of the present invention.

FIG. 39 is a cross-sectional view showing a schematic configuration of a light guide unit of a blood sugar value measurement apparatus (a concentration determination apparatus) of a thirteenth embodiment of the present invention. A difference between a light guide unit 62 of a blood sugar value measurement apparatus 61 of the present embodiment and the light guide unit 42 of the blood sugar value measurement apparatus 41 of the second embodiment is that the internal heat insulation unit (temperature adjustment means) 53 of the twelfth embodiment is provided in a surface of a heat insulating material 23 opposite to the pulse wave sensor 24 and the surface temperature sensor 43. Since, besides the light guide unit 62, a simulation unit 2 to a concentration correction unit 15 are exactly the same as the blood sugar value measurement apparatus 41 of the eleventh embodiment, a description thereof will be omitted.

A deep-portion thermometer using a heat flow compensation method is configured of the surface temperature sensor 43, the internal temperature sensor 44, and the internal heat insulation unit 53. In the deep-portion thermometer, when sufficient time lapses, tissues of the epidermis 220 and the dermis 230 reach thermal equilibrium, and the temperature of the epidermis 220 is coincident with the temperature of the dermis 230. Accordingly, it is possible to measure the temperature of the dermis 230.

Figure 40:
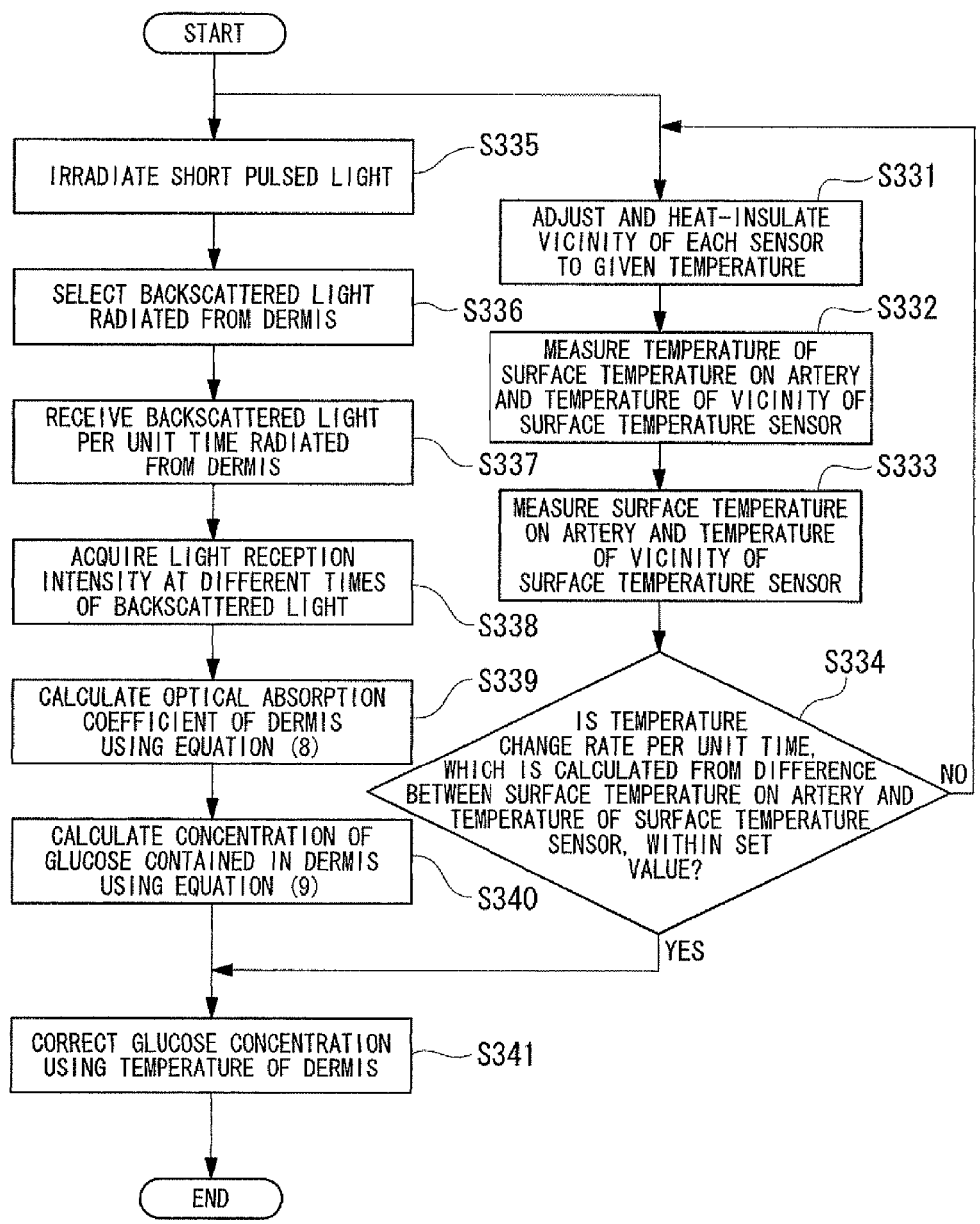
FIG. 40 is a flowchart showing a process of measuring a blood sugar value in the thirteenth embodiment of the present invention.

Next, a process of measuring a blood sugar value using the blood sugar value measurement apparatus 61 will be described based on FIG. 40.

First, a user operates the blood sugar value measurement apparatus 41 by putting the blood sugar value measurement apparatus 41 to skin of, for example, his or her wrist and pressing a measurement initiation switch (not shown).

Here, the internal heat insulation unit 53 adjusts and heat-insulates vicinities of the pulse wave sensor 24, the surface temperature sensor 43 and the internal temperature sensor 44 to a given temperature, for example, 36.0° C. (step S331).

Then, the light guide unit 62 is slid along the skin 210 in any direction in a state in which a leading end portion of the light guide unit 62 is put to the skin 210 of the living body, and pulse pressure of the vicinity of a portion having a beat in the living body, i.e., pulse pressure of the artery, is detected in a non-contact manner by the pulse wave sensor 24 (step S332).

The surface temperature sensor 43 then measures the temperature of the skin 210 on the artery and the sensor internal temperature measurement sensor 44 measures temperature of the vicinity of the surface temperature sensor 43 (step S333).

Then, the surface and internal temperature change rate calculation unit 45 calculates a difference between the surface temperature on the artery measured by the surface temperature sensor 43 and the temperature of the vicinity of the surface temperature sensor 43 measured by the sensor internal temperature measurement sensor 44, as a temperature change rate per unit time, and judges whether the temperature change rate per unit time is within a set value (step S334).

Here, when the temperature change rate per unit time is within the set value, the irradiation unit 5 irradiates short pulsed light to the dermis 230 constituting the skin 210 (step S335).

On the other hand, when the temperature change rate per unit time exceeds the set value, this is reported using a reporting means such as sound and the processes from the temperature adjustment and heat-insulation (step S331) are performed again.

Figure 37:
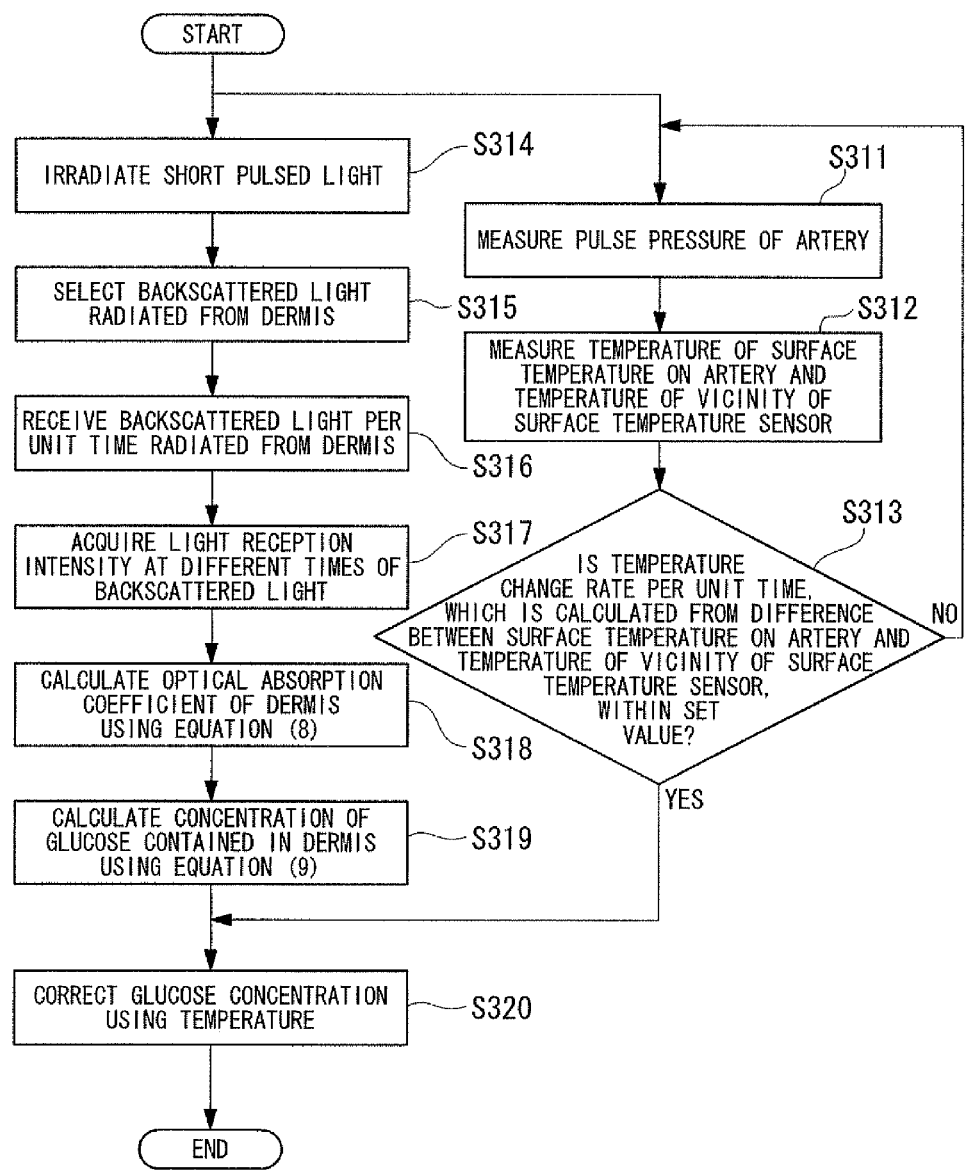
FIG. 37 is a flowchart showing a process of measuring a blood sugar value in an eleventh embodiment of the present invention.

After the short pulsed light is irradiated, processes of a process (step S336) of selecting the backscattered light radiated by the dermis 230 from among the backscattered light radiated from the subcutaneous tissue 240, the dermis 230 and the epidermis 220 to a process (step S340) in which the concentration calculation unit 13 calculates the concentration of the glucose contained in the dermis 230 are exactly the same as the process (step S315 to S319) shown in FIG. 37 of the eleventh embodiment.

The concentration correction unit 15 corrects the glucose concentration of the dermis 230 calculated by the concentration calculation unit 13 using the surface temperature on the artery measured by the surface temperature sensor 43, from the following correction equation (step S341):

measured value of glucose concentration-value corresponding to absorption coefficient of water.

For example, when the temperature of the dermis 230 (=a surface temperature on the artery) rises by T° C., a change amount of the absorption coefficient of the light is −0.004/mm×T. Accordingly, a reduction amount of the glucose concentration when the temperature of the dermis 230 rises by T° C. is 500 mg/dl×T.

Even in the present embodiment, the same effects as those of the blood sugar value measurement apparatus 41 of the eleventh embodiment can be achieved.

In addition, the vicinities of the pulse wave sensor 24, the surface temperature sensor 43 and the sensor internal temperature measurement sensor 44 are heat-insulated by the internal heat insulation unit 53, the pulse pressure of the artery is then detected in a non-contact manner by the pulse wave sensor 24 and then the surface temperature on the artery and the temperature of the vicinity of the surface temperature sensor 43 are measured. When the temperature change rate per unit time calculated from the difference between the surface temperature on the artery measured by the surface temperature sensor 43 and the temperature of the vicinity of the surface temperature sensor 43 measured by the sensor internal temperature measurement sensor 44 is within the set value, the glucose concentration of the dermis 230 is corrected using the surface temperature on the artery measured by the surface temperature sensor 43. Accordingly, a temperature change in each of the pulse wave sensor 24, the surface temperature sensor 43 and the sensor internal temperature measurement sensor 44 can be suppressed, and measurement accuracy of each of the pulse wave sensor 24, the surface temperature sensor 43 and the sensor internal temperature measurement sensor 44 can be improved by adjusting and heat-insulating the vicinities of the pulse wave sensor 24, the surface temperature sensor 43 and the internal temperature sensor 44 to a given temperature.

(Fourteenth Embodiment)

Figure 41:
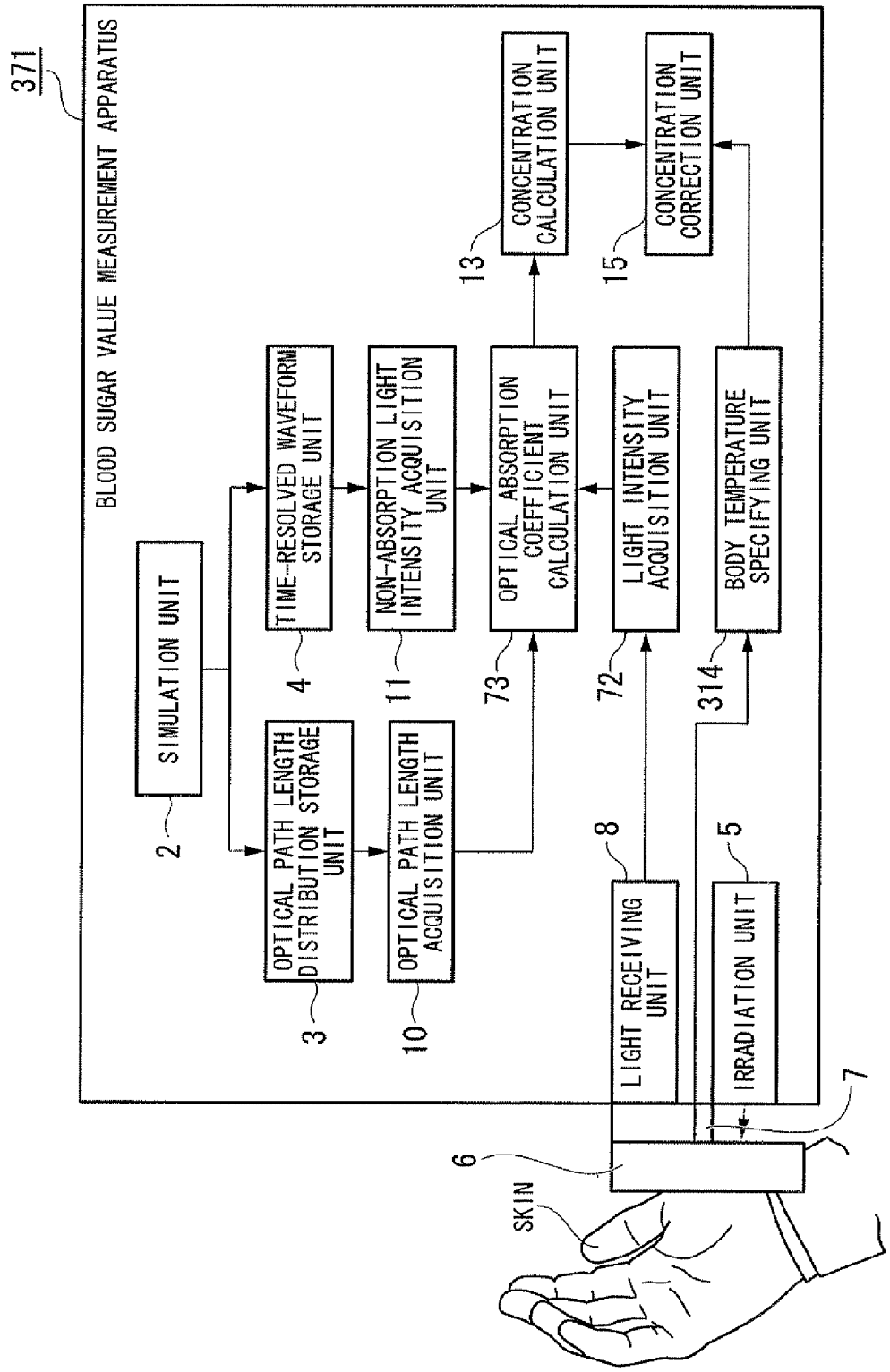
FIG. 41 is a schematic block diagram showing a configuration of a blood sugar value measurement apparatus in a fourteenth embodiment of the present invention.

FIG. 41 is a schematic block diagram showing a configuration of a blood sugar value measurement apparatus (a concentration determination apparatus) of a fourteenth embodiment of the present invention. A difference between a blood sugar value measurement apparatus 371 of the present embodiment and the blood sugar value measurement apparatus 301 of the tenth embodiment is that the light intensity acquisition unit 9 and the optical absorption coefficient calculation unit 12 are substituted with a light intensity acquisition unit (light intensity acquisition unit) 72 and an optical absorption coefficient calculation unit (optical absorption coefficient calculation unit) 73 having different functions from the light intensity acquisition unit 9 and the optical absorption coefficient calculation unit 12.

The light intensity acquisition unit 72 acquires light intensity, between a given time and at least a given time τ, of the backscattered light radiated from the dermis, which has been received by the light receiving unit 8.

The optical absorption coefficient calculation unit 73 calculates the optical absorption coefficient in the dermis of the skin to which the short pulsed light having a specific wavelength $\lambda_k$ has been irradiated, using Equation (10).

Figure 42:
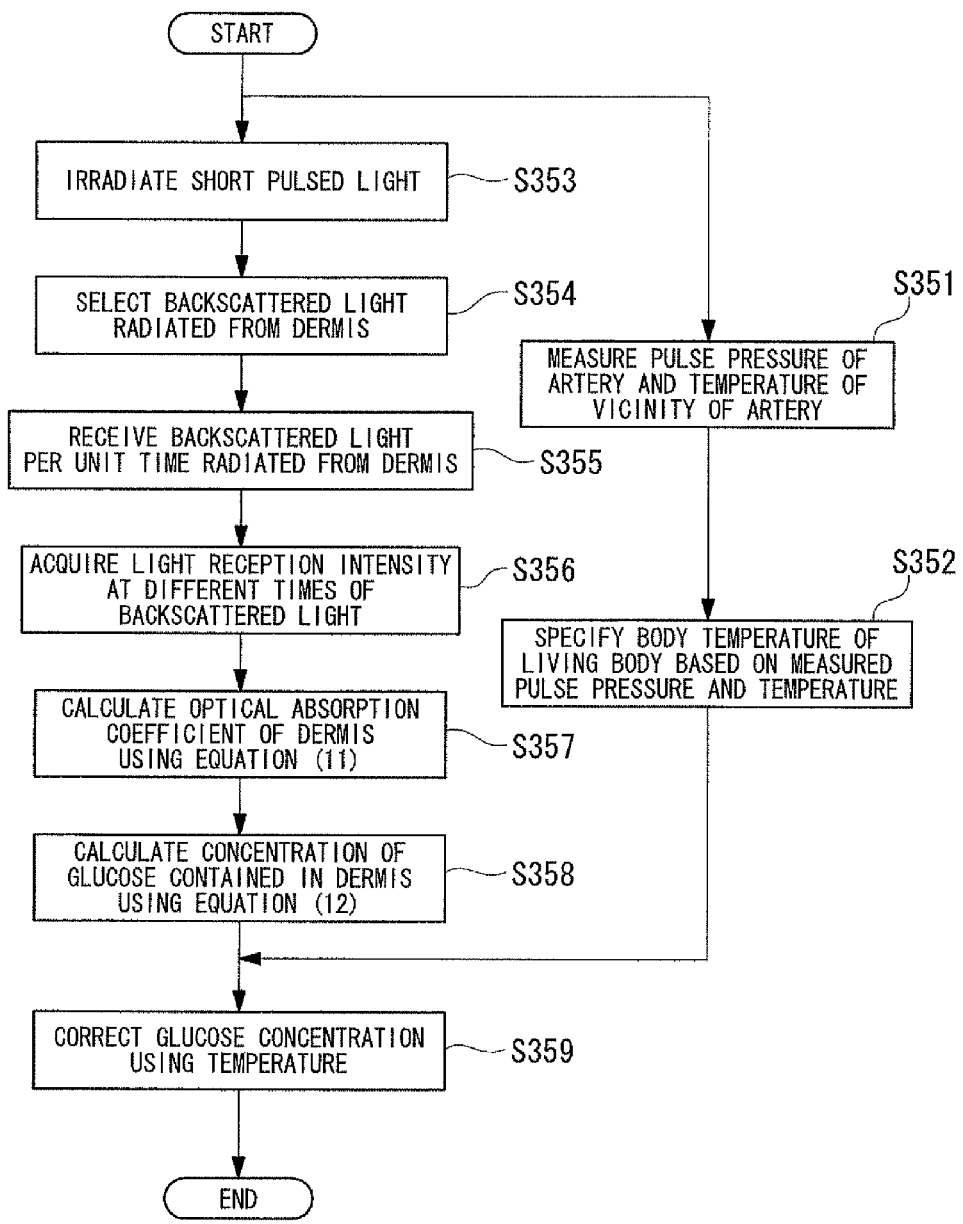
FIG. 42 is a flowchart showing a process of measuring a blood sugar value in the fourteenth embodiment of the present invention.

Next, a process of measuring a blood sugar value using the blood sugar value measurement apparatus 371 will be described based on FIG. 42.

In this process, since processes from a process (step S351) in which the pulse wave sensor 24 detects pulse pressure of the artery in a non-contact manner and the temperature sensor 25 measures the temperature of the skin 210 on the artery in a non-contact manner to a process (step S354) of selecting the backscattered light radiated by the dermis 230 are the same as the process (steps S301 to 304) shown in FIG. 35, a description thereof will be omitted.

After the backscattered light is selected, the light receiving unit 8 receives backscattered light up to given time τ radiated from the dermis 230 (step S355). In this case, the light receiving unit 8 records the light reception intensity between irradiation initiation and at least the given time τ in an internal memory.

Then, when the light intensity acquisition unit 72 is notified that the light receiving unit 8 has completed light reception, the light intensity acquisition unit 72 acquires the light reception intensity between the irradiation initiation and at least a given time t of the backscattered light radiated from the dermis 230 (step S356).

Then, the optical absorption coefficient calculation unit 73 calculates the optical absorption coefficient of the dermis 230 based on the light reception intensity, between the irradiation initiation and at least the given time T, of the backscattered light radiated from the dermis 230 acquired by the light intensity acquisition unit 72 using Equation (11) (step S357).

Then, the concentration calculation unit 13 calculates concentration of the glucose contained in the dermis 230 based on the optical absorption coefficient μ of the dermis 230 calculated by the optical absorption coefficient calculation unit 73, using Equation (12) (step S358).

Then, the concentration correction unit 15 corrects the glucose concentration of the dermis 230 calculated by the concentration calculation unit 13 based on the temperature of the skin 210 on the artery measured by the temperature sensor 25, using the following correction equation (step S359):

measured value of glucose concentration-value corresponding to absorption coefficient of water.

For example, when the temperature of the skin 210 on the artery rises by T° C., a change amount of the absorption coefficient of the light is −0.004/mm×T. Accordingly, a reduction amount of the glucose concentration when the temperature of the dermis 230 rises by T° C. is 500 mg/dl×T.

Even in the present embodiment, the same effects as those of the blood sugar value measurement apparatus 301 of the tenth embodiment can be achieved.

In addition, the light intensity acquisition unit 72 acquires the light intensity between a given time and at least a given time z and the optical absorption coefficient calculation unit 73 calculates the optical absorption coefficient of the dermis 230 using Equation (2). Since the calculated glucose concentration of the dermis 230 is corrected using the temperature of the skin 210 on the artery measured by the temperature sensor 25, it is possible to accurately detect the glucose concentration in the dermis calculated based on the back-scattered light according to the active state of the living body. Thus, it is possible to accurately measure the glucose concentration in the dermis according to the active state of the living body in a non-invasive manner and in a short time.

(Fifteenth Embodiment)

Figure 43:
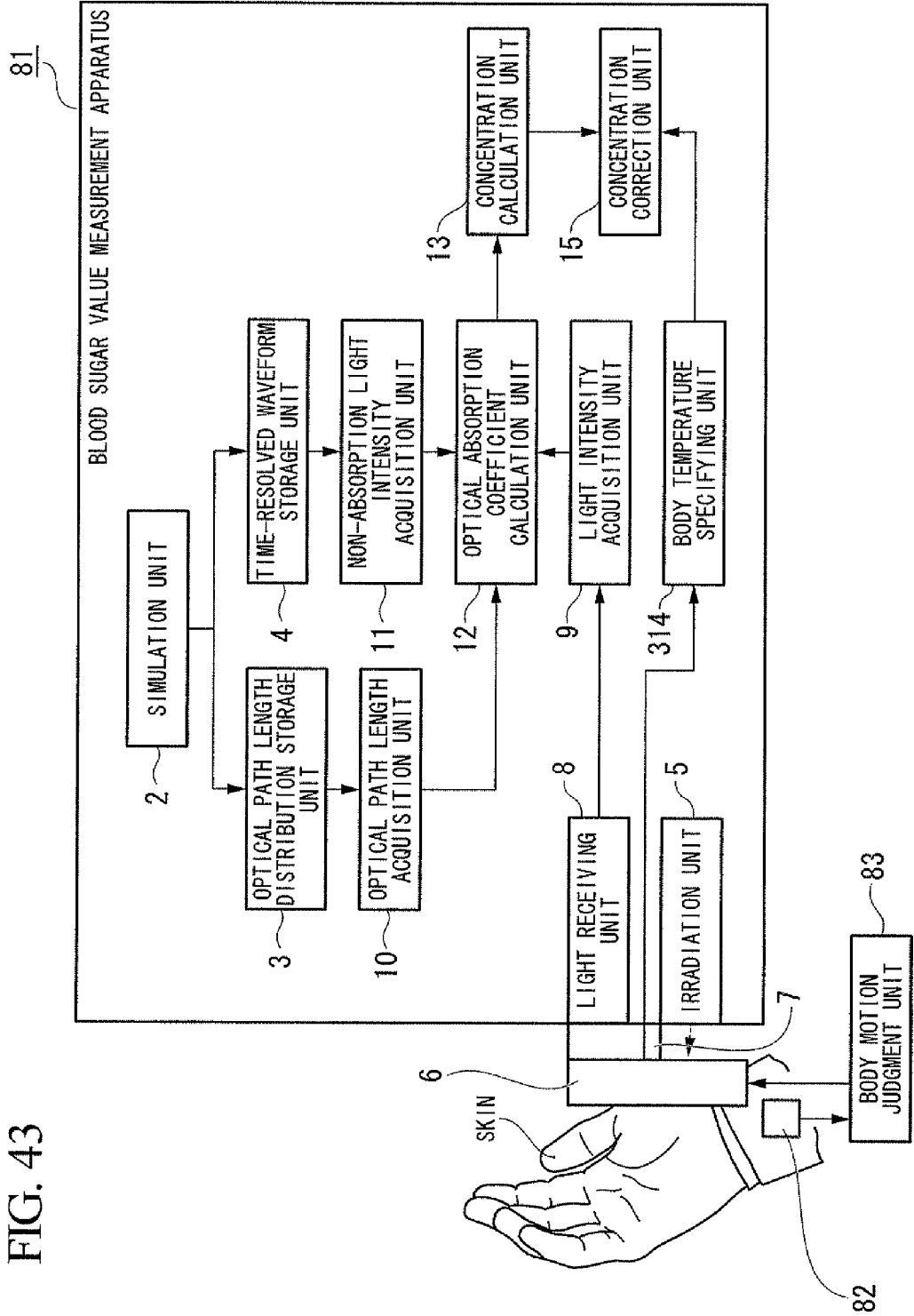
FIG. 43 is a schematic block diagram showing a configuration of a blood sugar value measurement apparatus in a fifteenth embodiment of the present invention.

FIG. 43 is a schematic block diagram showing a configuration of a blood sugar value measurement apparatus (a concentration determination apparatus) of a fifteenth embodiment of the present invention. A difference between a blood sugar value measurement apparatus 81 of the present embodiment and the blood sugar value measurement apparatus 301 of the tenth embodiment is that the former further includes a body motion detection unit (body motion detection unit) 82 for detecting a body motion of a living body, and a body motion judgment unit (body motion judgment means) 83 for judging whether the body motion of the living body detected by the body motion detection unit 82 is within a given range.

The body motion detection unit 82 includes a sensor, such as an acceleration sensor, for detecting a body's movement in a motion of the living body.

The body motion detection unit 82 converts a detected analog signal into a digital signal using an A/D conversion unit, and performs an FFT process on a body motion signal converted into the digital signal using an FFT processing unit.

The body motion judgment unit 83 judges whether the living body is in a static state or in an active (mobile) state based on the body motion signal subjected to the FFT process.

As the judgment method, for example, the body motion judgment unit 83 judges, for the body motion signal that has been subjected to the FFT process, whether the highest amplitude level of a frequency component is equal to or less than a threshold value, and judges that the living body is in a static state when the amplitude level is equal to or less than the threshold value and the living body is in an active state when the amplitude level exceeds the threshold value.

Figure 44:
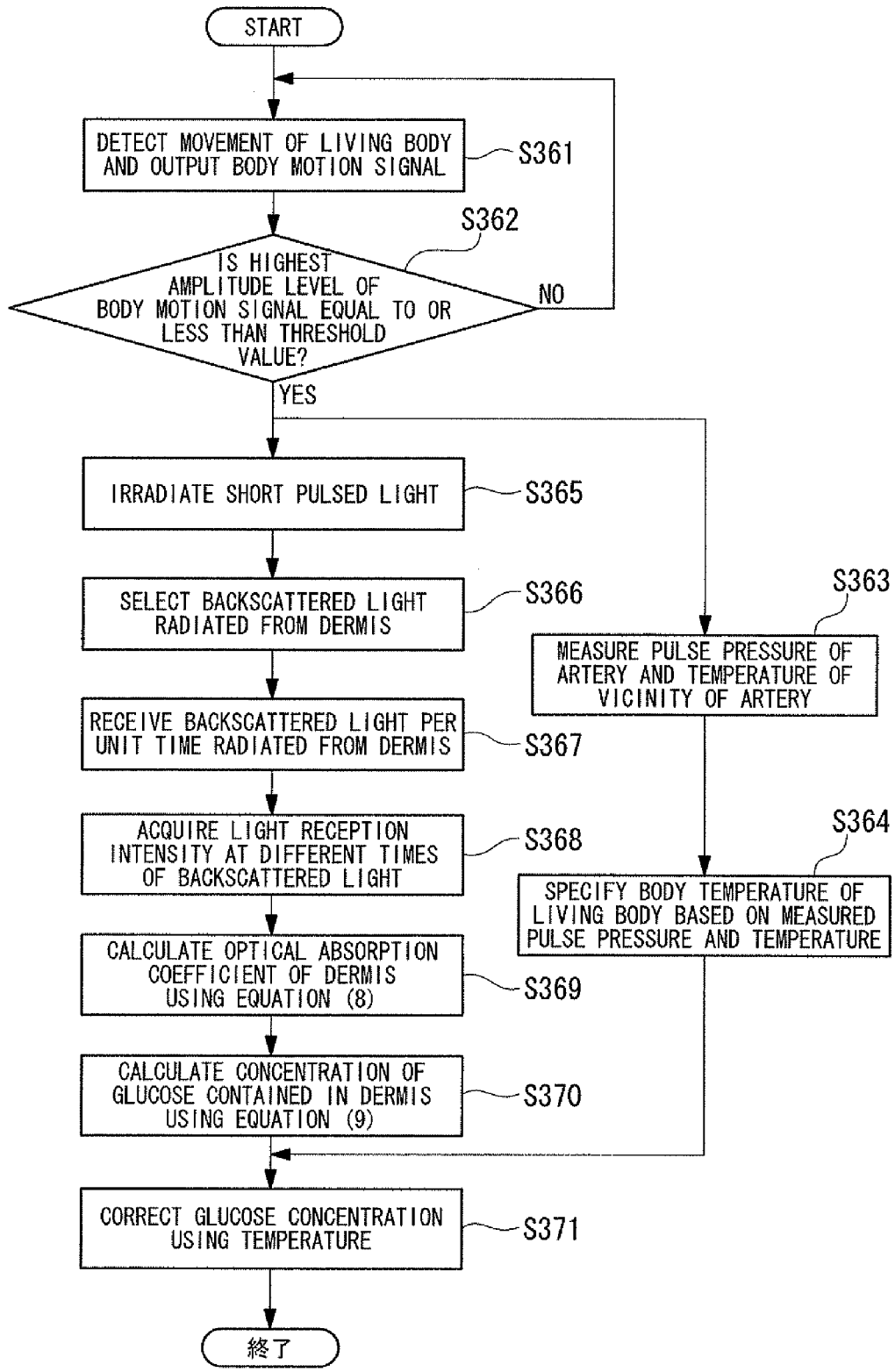
FIG. 44 is a flowchart showing a process of measuring a blood sugar value in the fifteenth embodiment of the present invention.

Next, a process of measuring a blood sugar value using the blood sugar value measurement apparatus 81 will be described based on FIG. 44.

First, a user operates the blood sugar value measurement apparatus 81 by putting the blood sugar value measurement apparatus 81 to skin of, for example, his or her wrist and pressing a measurement initiation switch (not shown).

Here, a movement of the living body is detected in a state in which the body motion detection unit 82 is put to the skin 210 of the living body (step 361).

Then, the body motion judgment unit 83 judges whether the highest amplitude level of a frequency component of the body motion signal detected by the body motion detection unit 82 is equal to or less than the threshold value (step S362).

Here, when the amplitude level is equal to or less than the threshold value, the body motion judgment unit 83 judges that the living body is in a static state. The light guide unit 6 is slid along the skin 210 in any direction in a state in which a leading end portion of the light guide unit 6 is put to the skin 210 of the living body, and pulse pressure of the vicinity of a portion having a beat in the living body, i.e., pulse pressure of the artery, is detected in a non-contact manner by the pulse wave sensor 24. Simultaneously, a temperature of the skin 210 near the artery detected by the pulse wave sensor 24 is measured in a non-contact manner by the temperature sensor 25 (step S363).

On the other hand, when the amplitude level exceeds the threshold value, it is judged that the living body is in an active state and a movement of the living body is detected again (step 361).

In the process, since processes from a process (step 5363) in which the pulse wave sensor 24 detects pulse pressure of the artery in a non-contact manner and the temperature sensor 25 measures the temperature of the skin 210 on the artery in a non-contact manner to a process (step S371) in which the concentration correction unit 14 corrects the glucose concentration are the same as the process shown in FIG. 35, a description thereof will be omitted.

As described above, according to the present embodiment, since the movement of the living body is detected by the body motion detection unit 82 and then the determination is made by the body motion judgment unit 83 as to whether the living body is in the static state, the static state of the living body can be accurately recognized. Accordingly, it is possible to accurately detect the concentration of the target component in any layer of the observed object in the static state of the living body.

Further, in each embodiment, the case of measuring the concentration of the glucose contained in the dermis of the skin in which a blood sugar value measurement apparatus is used as a concentration determination apparatus, skin of a person's palm is used as an observed object, the glucose is used as a target component, and the short pulsed light having a specific wavelength is used as light having a specific wavelength has been described, but the present invention is not limited thereto and the concentration determination method may be used for another apparatus for determining a concentration of a target component in any layer of an observed object formed of a plurality of light scattering medium layers.

Further, in each embodiment, only a set of the pulse wave sensor 24 and the temperature sensor 25, or only a set of the pulse wave sensor 24, the surface temperature sensor 43 and the internal temperature sensor 44 is provided, but two or more sets may be provided.

For example, plural sets of a pulse wave sensor 24 and the temperature sensor 25 or plural sets of the pulse wave sensor 24, the surface temperature sensor 43 and the internal temperature sensor 44, e.g., a structure in a 2×2 matrix, may be provided.

While preferred embodiments of the invention have been described and illustrated above, it should be understood that these are examples of the invention and are not to be considered as limiting. Additions, omissions, substitutions, and other modifications can be made without departing from the scope of the invention. Accordingly, the invention is not to be considered as being limited by the foregoing description, and is only limited by the scope of the appended claims.

What is claimed is:

1. A concentration determination apparatus that determines a concentration of a target component in a skin of an observed object including a plurality of light scattering medium layers, the concentration determination apparatus comprising:
   a light receiving unit configured to receive backscattered light radiated from the skin;
   a temperature sensor configured to measure a temperature of the skin a processor; and
   a memory, the memory storing a processor executable program, the processor executable program being configured to:
   calculate a wavelength wherein a temperature change of the absorption coefficient of water in the skin is small by comparing a difference between an absorption spectrum of water at a reference temperature and a temperature that is different from the reference temperature;
   correct the concentration of the target component in the skin using the temperature of the skin measured by the temperature sensor; store data relating to light emitted to the observed object having the wavelength at which the temperature change of the absorption coefficient of water in the skin is small;
   store data relating to selecting the backscattered light radiated from the skin from among plural types of backscattered light radiated from the observed object by irradiating the light;
   store data relating to receiving the backscattered light radiated from the skin;
   acquire light intensity received, at a given time, of a model of a time-resolved waveform of short pulsed light, the short pulsed light having a pulse width of about 10 psec or less, and acquire the light intensity of the skin at a plurality of times $t_1$ to $t_m$,
   calculate an optical absorption coefficient of the skin based on the light intensity acquired;
   calculate the concentration of the target component in the skin based on the optical absorption coefficient calculated;
   store a model of an optical propagation path length distribution in each of the plurality of light scattering medium layers, of the short pulsed light irradiated to the observed object;
   store the model of the time-resolved waveform of the short pulsed light irradiated to the observed object;
   acquire an optical path length of each of the plurality of light scattering medium layers, at the given time, of the model of the optical propagation path length distribution; and
   calculate the optical absorption coefficient of the skin using the following equation (1):

$$\begin{cases} N(t_1)\ln\left(\dfrac{N(t_1)}{I(t_1)}\right) = \sum_{i=1}^{n} \mu_i L_i(t_1) \\ \vdots \\ N(t_m)\ln\left(\dfrac{N(t_m)}{I(t_m)}\right) = \sum_{i=1}^{n} \mu_i L_i(t_m) \end{cases} \quad (1)$$

wherein $I(t)$ denotes the intensity of the light received at time t, $N(t)$ denotes the light intensity, at time t, of the model of the time-resolved waveform of the short pulsed light, $L_i(t)$ denotes an optical path length of an i-th layer, at time t, of the model of the optical propagation path length distribution in each of the plurality of light scattering medium layers, and $\mu_i$ denotes an optical absorption coefficient of the i-th layer;
   an irradiation unit configured to irradiate, to the observed object, light having the calculated wavelength wherein the temperature change of the absorption coefficient of water in the skin is small.

2. The concentration determination apparatus according to claim 1, wherein a plurality of times when the light intensity is acquired includes a peak time of the optical propagation path length distribution of each of the plurality of light scattering medium layers.

3. The concentration determination apparatus according to claim 1, the memory storing the processor executable program, the processor executable program being operable to calculate the concentration of the target component in the layer using the following equation (3):

$$\begin{cases} \mu_{a(1)} - \mu_{a(2)} = \sum_{j=1}^{p} g_j(\varepsilon_{j(1)} - \varepsilon_{j(2)}) \\ \vdots \\ \mu_{a(q-1)} - \mu_{a(q)} = \sum_{j=1}^{p} g_j(\varepsilon_{j(q-1)} - \varepsilon_{j(q)}) \end{cases} \quad (3)$$

where $\mu_a$ denotes an optical absorption coefficient in an a-th layer that is the layer, $g_j$ denotes a molar concentration of a j-th component constituting the observed object, $\epsilon_j$ denotes an optical absorption coefficient of the j-th component, p denotes the number of main components constituting the observed object, and q denotes the number of types of the specific wavelength.

4. The concentration determination apparatus according to claim 1, wherein the concentration determination apparatus determines the concentration of glucose in the skin of the observed object.

5. A concentration determination method of determining a concentration of a target component in any skin layer of an observed object including a plurality of light scattering medium layers using a processor and a memory, the concentration determination method comprising:
   measuring a temperature of the skin using a temperature sensor
   selecting, by a light scattering medium layer selection unit, backscattered light radiated from the skin from among plural types of backscattered light radiated from the observed object by irradiating the light;
   receiving, by a light receiving unit, the backscattered light radiated from the skin;
   acquiring, by a light intensity acquisition unit, intensity of the light received by the light receiving unit, at a given time, of a model of a time-resolved waveform of short pulsed light, the short pulsed light having a pulse width of about 10 psec or less, and acquiring the light intensity of the skin at a plurality of times $t_1$ to $t_m$,
   calculating, by an optical absorption coefficient calculation unit, an optical absorption coefficient of the skin based on the light intensity acquired by the light intensity acquisition unit; and
   calculating, by a concentration calculation unit, the concentration of the target component in the skin based on the optical absorption coefficient calculated by the optical absorption coefficient calculation unit, the memory storing a processor executable program, the processor executable program being configured to:

calculate a wavelength wherein the temperature change of the absorption coefficient of water in the skin is small by comparing a difference between an absorption spectrum of water at a reference temperature and a temperature that is different from the reference temperature;

correct the concentration of the target component in the skin using the temperature of the skin measured by the temperature sensor; store a model of an optical propagation path length distribution in each of the plurality of light scattering medium layers, of the short pulsed light irradiated to the observed object;

store the model of the time-resolved waveform of the short pulsed light irradiated to the observed object;

acquire an optical path length of each of the plurality of light scattering medium layers, at the given time, of the model of the optical propagation path length distribution; and calculate the optical absorption coefficient of the skin using the following equation (1):

$$\begin{cases} N(t_1)\ln\left(\frac{N(t_1)}{I(t_1)}\right) = \sum_{i=1}^{n} \mu_i L_i(t_1) \\ \vdots \\ N(t_m)\ln\left(\frac{N(t_m)}{I(t_m)}\right) = \sum_{i=1}^{n} \mu_i L_i(t_m) \end{cases} \quad (1)$$

where I(t) denotes the intensity of the light received at time t, N(t) denotes the light intensity, at time t, of the model of the time-resolved waveform of the short pulsed light, Li(t) denotes an optical path length of an i-th layer, at time t, of the model of the optical propagation path length distribution in each of the plurality of light scattering medium layers, and $\mu_i$ denotes an optical absorption coefficient of the i-th layer; and irradiating, by an irradiation unit, to the observed object, light having the calculated wavelength at which the temperature change of the absorption coefficient of water in the skin is small.

6. The method according to claim 5, wherein the determining the concentration of the target component in any layer of the observed object determines the concentration of glucose.

7. A non-transitory program that causes a computer of a concentration determination apparatus determining a concentration of a target component in any skin layer of an observed object including a plurality of light scattering medium layers to execute:

a temperature sensor that measures a temperature of the skin;

a light scattering medium layer selection process of selecting backscattered light radiated from the layer from among plural types of backscattered light radiated from the observed object by irradiating the light;

a light receiving process of receiving the backscattered light radiated from the skin using a light receiving unit;

a light intensity acquisition process of acquiring intensity of the light received in the light receiving process, at a given time, of a model of the time-resolved waveform of short pulsed light, the short pulsed light having a pulse width of about 10 psec or less, and acquire the light intensity of the skin at a plurality of times $t_1$ to $t_m$;

an optical absorption coefficient calculation process of calculating an optical absorption coefficient of the skin based on the light intensity acquired in the light intensity acquisition process; and a concentration calculation process of calculating the concentration of the target component in the skin based on the optical absorption coefficient calculated in the optical absorption coefficient calculation process, the concentration determination apparatus comprising a processor and a memory, the memory storing a processor executable program, the processor executable program being configured to:

calculate a wavelength wherein a temperature change of the absorption coefficient of water in the skin is small by comparing a difference between an absorption spectrum of water at a reference temperature and a temperature that is different from the reference temperature;

correct the concentration of the target component in the skin using the temperature of the skin measured by the temperature sensor; store a model of an optical propagation path length distribution in each of the plurality of light scattering medium layers, of the short pulsed light irradiated to the observed object;

store the model of the time-resolved waveform of the short pulsed light irradiated to the observed object;

acquire an optical path length of each of the plurality of light scattering medium layers, at the given time, of the model of the optical propagation path length distribution; and calculate the optical absorption coefficient of the skin using the following equation (1):

$$\begin{cases} N(t_1)\ln\left(\frac{N(t_1)}{I(t_1)}\right) = \sum_{i=1}^{n} \mu_i L_i(t_1) \\ \vdots \\ N(t_m)\ln\left(\frac{N(t_m)}{I(t_m)}\right) = \sum_{i=1}^{n} \mu_i L_i(t_m) \end{cases} \quad (1)$$

where I(t) denotes the intensity of the light received at time t, N(t) denotes the light intensity, at time t, of the model of the time-resolved waveform of the short pulsed light, Li(t) denotes an optical path length of an i-th layer, at time t, of the model of the optical propagation path length distribution in each of the plurality of light scattering medium layers, and $\mu_i$ denotes an optical absorption coefficient of the i-th layer; and an irradiation process of irradiating using an irradiation unit, to the observed object, light having the calculated wavelength at which the temperature change of an absorption coefficient of water in the skin is small.

8. The non-transitory program according to claim 7, wherein the concentration determination apparatus determines the concentration of glucose in any layer of the observed object.

* * * * *